US006414222B1

(12) United States Patent
Gengenbach et al.

(10) Patent No.: US 6,414,222 B1
(45) Date of Patent: Jul. 2, 2002

(54) GENE COMBINATIONS FOR HERBICIDE TOLERANCE IN CORN

(75) Inventors: Burle G. Gengenbach, St. Paul; David A. Somers; Margaret A. Egli, both of Roseville, all of MN (US); Lorelei C. Marshall, Iowa City, IA (US); Donald L. Wyse, Wyoming, MN (US); Shelia M. Lutz, St. Paul, MN (US); Kevin L. Van Dee, Iowa City, IA (US); William B. Parker, Boonville, MO (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 08/697,826

(22) Filed: Aug. 30, 1996

Related U.S. Application Data

(63) Continuation-in-part of application No. PCT/US96/04625, filed on Apr. 4, 1996, which is a continuation-in-part of application No. 08/417,089, filed on Apr. 5, 1995, which is a continuation-in-part of application No. 08/014,326, filed on Feb. 5, 1993, now Pat. No. 5,498,544.

(51) Int. Cl.$^7$ .......................... A01H 5/00; A01H 1/00; A01H 1/02; C12N 5/04

(52) U.S. Cl. .......................... 800/300.1; 800/300.1; 800/260; 800/266; 800/267; 800/268; 800/270; 800/275; 800/276; 800/320.1; 435/413; 435/424; 435/430; 435/430.1

(58) Field of Search .......................... 800/300.1, 260, 800/266, 267, 268, 270, 275, 276, 320.1; 435/413, 424, 430, 430.1

(56) References Cited

U.S. PATENT DOCUMENTS

| | | | |
|---|---|---|---|
| 4,326,358 A | 4/1982 | Lawrence, Jr. et al. | 47/58 |
| 4,731,499 A | 3/1988 | Puskaric et al. | 800/1 |
| 4,761,373 A | 8/1988 | Anderson et al. | 435/172.3 |
| 4,812,599 A | * 3/1989 | Segebart | 800/1 |
| 4,874,421 A | 10/1989 | Kleschick et al. | 71/9 H |
| 4,940,835 A | 7/1990 | Shah et al. | 800/205 |
| 5,107,065 A | 4/1992 | Shewmaker et al. | 800/205 |
| 5,162,602 A | 11/1992 | Somers et al. | 800/235 |
| 5,190,931 A | 3/1993 | Inouye | 435/91 |
| 5,290,696 A | * 3/1994 | Somers et al. | 436/240.5 |
| 5,498,544 A | 3/1996 | Gengenbach et al. | 435/320.1 |
| 5,500,361 A | 3/1996 | Kinney | 435/172.3 |
| 5,510,474 A | 4/1996 | Quail et al. | 536/24.1 |
| 5,530,186 A | 6/1996 | Hitz et al. | 800/205 |
| 5,539,092 A | 7/1996 | Haselkorn et al. | 536/23.2 |
| 5,559,220 A | 9/1996 | Roessler et al. | 536/23.6 |
| 5,608,152 A | 3/1997 | Kridl et al. | 800/205 |
| 5,689,045 A | 11/1997 | Logemann et al. | 800/205 |
| 5,767,362 A | 6/1998 | Best et al. | 800/205 |
| 5,767,363 A | 6/1998 | De Silva et al. | 800/205 |
| 5,792,627 A | 8/1998 | Haselkorn et al. | 435/69.1 |
| 5,801,233 A | 9/1998 | Haselkorn et al. | 536/23.6 |
| 5,854,420 A | 12/1998 | Ashton et al. | 800/205 |

FOREIGN PATENT DOCUMENTS

| | | | |
|---|---|---|---|
| DE | 4234131 | 4/1994 | |
| EP | 0 270 356 A2 | 6/1988 | ........... C12N/15/00 |
| EP | 0469810 | 2/1992 | |
| SU | 1 720 594 A1 | 3/1992 | ........... A01H/1/02 |
| WO | WO98/07647 | 8/1989 | |
| WO | 92/11243 | 6/1993 | |
| WO | 94/08016 | 4/1994 | |
| WO | 94/17188 | 8/1994 | |
| WO | 94/23027 | 10/1994 | |
| WO | 94/29467 | 12/1994 | |
| WO | 95/06128 | 3/1995 | ........... C12N/15/82 |
| WO | 95/29246 | 11/1995 | |

OTHER PUBLICATIONS

Fehr, Principles of Cultivar Development, McGraw–Hill, Inc., 1987, pp. 80–82.*
Falconer, Quantitative Genetics, Longman Scientific and Technical, 1989, pp. 112–117.*
Principles of Cultivar Development, Theory and Technique, Walter R. Fehr, Iowa State University, McGraw–Hill, Inc., pp. 110, 403–409, 428–445, 1987.*
Van Dee, Master of Science thesis, University of Minnesota, pp. 1–62, 1990.*
Parker et al., Proc. Natl. Acad. Sci., vol. 87, pp. 7175–7179, 1990.*
Marshall et al., Theor Appl Genet, 83:435–442, 1992.*
Caffrey et al., Maize Genetics Cooperation Newsletter, vol. 69, pp. 3–4, 1995.*
Egli et al., Plant Physiol., 101:499–506, 1993.*
Al–Feel, W., et al., "Cloning of the Yeast FAS3 Gene and Primary Structure of Yeast Acetyl–CoA Carboxylase", *Proc. Natl. Acad. Sci. USA*, 89, 4534–4538 (May 1992).
Anderson, P.C., et al., "Cell Culture Selection of Herbicide Tolerant Corn", Agronomy Abstract, Division C–1—Crop Breeding, Genetics and Cytology, ASA, Madison, WI, p. 56 (1985).
Anderson, P.C., et al., "Selection of an Imidazolinone Tolerant Mutant of Corn", Abstracts, Sixth International Congress on Plant Tissue Cell Culture, Minneapolis, MN, p. 437 (Aug. 4–8, 1986).
Bai, D.H., et al., "Molecular Cloning of cDNA for Acetyl–Coenzyme A Carboxylase", *Journal of Biological Chemistry*, 261, 12395–12399 (Sep. 15, 1986).
Bettey, M., et al., "Purification and Characterization of Acetyl CoA Carboxylase from Developing Pea Embryos", *J. Plant Physiol.*, 140, 513–520 (1992).

(List continued on next page.)

Primary Examiner—Bruce R. Campell
Assistant Examiner—Anne Marie Grunberg
(74) Attorney, Agent, or Firm—Schwegman, Lundberg, Woessner & Kluth, P.A.

(57) ABSTRACT

The present invention provides methods for preparing herbicide tolerant corn plants. Also provided are herbicide tolerant corn plants, as well as seeds and progeny derived from these plants.

31 Claims, 17 Drawing Sheets

OTHER PUBLICATIONS

Botterman, J., et al., "Engineering Herbicide Resistance in Plants", *Trends in Genetics*, 4, 219–222 (Aug. 1988).

Bowman, T.R., et al., "Selection for Resistance to Paraquat in Maize Embryogenic Cell Cultures", Abstracts, Sixth International Congress on Plant Tissue Cell Culture, Minneapolis, MN, Abstract No. 85, p. 73 (Aug. 4–8, 1986).

Charles, D.J., et al., "Characterization of Acetyl–CoA Carboxylase in the Seed of Two Soybean Genotypes", *Phytochemistry*, 25, 55–59 (1986).

Charles, D.J., et al., "Purification and Characterization of Acetyl–CoA Carboxylase from Developing Soybean Seeds", *Phytochemistry*, 25, 1067–1071 (1986).

D'Halluin, K., et al., "Transgenic Maize Plants by Tissue Electroporation", *The Plant Cell*, 4, 1495–1505 (Dec. 1992).

Darnell, J., et al., In: *Molecular Cell Biology, Revised*, Scientific American Books, Inc., New York, pp. 248–257 (1986).

Dimroth, P., et al., "Crystallization of Biotin Carboxylase, a Component Enzyme of the Acetyl–CoA Carboxylase System from *Escherichia coli*", Hoppe Seyler's *Z. Physiol. Chem.*, 352, 351–354 (Mar. 1971).

Egin–Buhler, B., et al., "Improved Purification and Further Characterization of Acetyl–CoA Carboxylase from Cultured Cells of Parsley (*Petroselinum hortense*)", *Eur. J. Biochem.*, 133, 335–339 (1983).

Egli, M., et al., "Biochemical and Genetic Characterization of Maize Acetyl–CoA Carboxylase", Abstracts, Maize Genetics Conference, Pacific Grove, CA (Mar. 19–22, 1992).

Egli, M., et al., "Cloning and Expression of Maize Acetyl–CoA Carboxylase", *Agronomy Abstracts*, 1992 Annual Meeting, Minneapolis, MN, p. 189 (1992).

Egli, M., et al., "Purification and Characterization of Maize Acetyl–CoA Carboxylase", *Plant Physiology*, 96S, p. 92 (1991).

Egli, M.A., et al., "A 233–kD Subunit of Acetyl–CoA Carboxylase is Encoded by the Maize Acc–1 Gene", *Maize Genetics Cooperation Newsletter*, 66, 94 (1992).

Egli, M.A., et al., "A Maize Acetyl–CoA Carboxylase cDNA Maps to Chromosome 2S", *Plant Physiology*, 105S, Abstract No. 311, p. 64 (1994).

Egli, M.A., et al., "Identification and Mapping of Maize Acetyl–CoA Carboxylase Genes", *Maize Genetics Cooperation Newsletter*, 68, 92–93 (Mar. 15, 1994).

Egli, M.A., et al., "Purification of Maize Leaf Acetyl CoA Carboxylase", *Maize Genetics Cooperation Newsletter*, 65, p. 95 (1991).

Elborough, K.M., et al., "Isolation of cDNAs from *Brassica napus* Encoding the Biotin–Binding and Transcarboxylase Domains of Acetyl–CoA Carboxylase: Assignment of the Domain Structure in a Full–Length *Arabidopsis thaliana* Genomic Clone", *Biochem. J.*, 301, 599–605 (1994).

Fawcett, J.A., et al., "Influence of Environment on Corn (*Zea mays*) Tolerance to Sethoxydim", *Week Science*, 35, 568–575 (1987).

Finlayson, S.A., et al., "Acetyl–Coenzyme A Carboxylase from the Developing Endosperm of *Ricinus communis*", *Archives of Biochemistry and Biophysics*, 225, 576–585 (1983).

Gornicki, P., et al., "Genes for Two Subunits of Acetyl Coenzyme A Carboxylase of Anabaena sp. Strain PCC 7120: Biotin Carboxylase and Biotin Carboxyl Carrier Protein", *Journal of Bacteriology*, 175, 5268–5272 (Aug. 1993).

Gornicki, P., et al., "Wheat Acetyl–CoA Carboxylase", *Plant Molecular Biology*, 22, 547–552 (1993).

Green, C.E., et al., "Plant Regeneration in Tissue Culture of Maize", In: *Maize for Biological Research*, Sheridan, W.F., (ed.), Plant Mol. Biol. Assoc., Charlottesville, VA, pp. 367–372 (1982).

Kannangra, C.G., et al., "Fat Metabolism in Higher Plants— LIV. A Procaryotic Type Acetyl CoA Carboxylase in Spinach Chloroplasts", *Archives of Biochemistry and Biophysics*, 152, 83–91 (1972).

Klein, T.M., et al., "High–Velocity Microprojectiles for Delivering Nucleic Acids into Living Cells", *Nature*, 327, 70–73 (1987).

Kondo, H., et al., "Acetyl–CoA Carboxylase from *Escherichia coli*: Gene Organization and Nucleotide Sequence of the Biotin Carboxylase Subunit", *Proc. Natl. Acad. Sci. USA*, 88, 9730–9733 (Nov. 1991).

Koziel, M.G., et al., "Optimizing Expression of Transgenes with an Emphasis on Post–Transcriptional Events", *Plant Molecular Biology*, 32, 398–405 (1996).

Laing, W.A., et al., "Activation of Spinach Chloroplast Acetyl–Coenzyme A Carboxylase by Coenzyme A", *FEBS Letters*, 144, 341–344 (Aug. 1982).

Lamhonwah, A.M., et al., "Sequence Homology around the Biotin–Binding Site of Human Propionyl–CoA Carboxylase and Pyruvate Carboxylase", *Archives of Biochemistry and Biophysics*, 254, 631–636 (May 1, 1987).

Li, S.J., et al., "The Genes Encoding the Biotin Carboxylase Subunit of *Escherichia coli* Acetyl–CoA Carboxylase", *Journal of Biological Chemistry*, 267, 855–863 (Jan. 15, 1992).

Li, S.J., et al., "The Genes Encoding the Two Carboxyltransferase Subunits of *Escherichia coli* Acetyl–CoA Carboxylase", *Journal of Biological Chemistry*, 267, 16841–16847 (Aug. 25, 1992).

Lopez–Casillas, F., et al., "Structure of the Coding Sequence and Primary Amino Acid Sequence of Acetyl–Coenzyme A Carboxylase", *Proc. Natl. Acad. Sci. USA*, 85, 5784–5788 (Aug. 1988).

Lutz, S., et al., "Characterization of Two Acetyl–CoA Carboxylase Genes from Maize", Abstracts, International Congress of Plant Molecular Biology, Amsterdam, The Netherlands (Jun. 1994).

Lutz, S., et al., "Characterization of Two Acetyl–CoA Carboxylase Genes from Maize", Abstracts, International Meeting on Plant Lipids, Paris, France, 1 p. (Jun. 1994).

Lutz, S., et al., "Intron Sequence Divergence in Type A and B Maize ACCase Genes", Abstracts, 37th Annual Maize Genetics Conference, Pacific Grove, CA, Poster No. 34, p. 38 (Mar. 16–19, 1995).

Lutz, S.M., et al., "Genomic Mapping of Acetyl–CoA Carboxylase Clones and Herbicide Resistance in Maize", Proceedings of the 1993 Plant Lipid Symposium, Minneapolis, MN, p. 10 (Jul. 29–31, 1993).

Marshall, L., et al ., "Chromosome Number and Fatty Acid Levels in Sethoxydim–Tolerant Corn Cell Lines", *Agronomy Abstracts*, 170 (1988).

McCabe, D.E., et al., "Stable Transformation of Soybean (*Glycine max*) by Particle Acceleration", *Bio/Technology*, 6, 923–926 (Aug. 1988).

Meredith, C.P., et al., "Herbicide Resistance in Plant Cell Cultures", In: *Herbicide Resistance in Plants*, LeBaron, H.M., et al., (eds.), John Wiley and Sons, New York, p. 275–291 (1982).

Metzler, D.E., In: *Biochemistry—The Chemical Reactions of Living Cells,* Academic Press, New York, p. 303 (1977).

Nikolau, B.J., et al., "Purification and Characterization of Maize Leaf Acetyl–Coenzyme A Carboxylase", *Archives of Biochemistry and Biophysics,* 288, 86–96 (Jan. 1984).

Parker, W.B., et al., "Dominant Mutations Causing Alterations in Acetyl–Coenzyme A Carboxylase Confer Tolerance to Cyclohexanedione and Aryloxyphenoxypropionate Herbicides in Maize", *Proc. Natl. Acad. Sci. USA,* 87, 7175–7170 (Sep. 1990).

Parker, W.B., et al., "Selection and Characterization of Corn Cell Lines Tolerant to Sethoxydim", Abstract No. 180, p. 64 (Feb. 3, 1988).

Parker, W.B., et al., "Selection and Characterization of Corn Cell Lines Tolerant to Sethoxydim", Proceedings of the North Central Weed Control Conference, 42, Kansas City, MO, p. 56 (Dec. 8–10, 1987).

Parker, W.B., et al., "Selection and Characterization of Sethoxyim Tolerant Corn Cell Lines", Third University of Minnesota Research Poster Session: Basic and Applied Bio–Medical Research in Academia and Industry (May 25, 1988).

Parker, W.B., et al., "Selection for Tolerance to Sethoxydim in Corn Tissue Culture", Proceedings of the North Central Weed Control Conference, 41, Milwaukee, WI, p. 93 (Dec. 2–4, 1986).

Phillips, R.L., et al., "Cell/Tissue Culture and In Vitro Manipulation", In: *Corn and Corn Improvement,* Sprague, G.F., et al., (eds.), American Society of Agronomy, Madison, WI, p. 345–387 (1988).

Post–Beittenmiller, D., et al., "Regulation of Plant Fatty Acid Biosynthesis", *Plant Physiology,* 100, 923–930 (1992).

Rhodes, C.A., et al,. "Genetically Transformed Maize Plants from Protoplasts", *Science,* 240, 204–207 (Apr. 1988).

Roessler, P.G., "Purification and Characterization of Acetyl–CoA Carboxylase from the Diatom *Cyclotella cryptica",* *Plant Physiology,* 92, 73–78 (1990).

Roessler, P.G., et al., "Cloning and Characterization of the Gene that Encodes Acetyl–Coenzyme A Carboxylase in the Alga *Cyclotella cryptica",* *Journal of Biological Chemistry,* 268, 19254–19259 (Sep. 15, 1993).

Schulte, W., et al., "A Gene Encoding Acetyl–Coenzyme A Carboxylase from *Brassica napus",* *Plant Physiology,* 106, 793–794 (1994).

Shorrosh, B.S., et al., "Molecular Cloning, Characterization, and Elicitation of Acetyl–CoA Carboxylase from Alfalfa", *Proc. Natl. Acad. Sci. USA,* 91, 4323–4327 (May 1994).

Slabas, A.R., et al., "Rapid Purification of a High Molecular Weight Subunit Polypeptide Form of Rape Seed Acetyl CoA Carboxylase", *Plant Science,* 39, 177–182 (1985).

Smith, C.J., et al., "Antisense RNA Inhibition of Polygalacturonase Gene Expression in Transgenic Tomatoes", *Nature,* 334, 724–726 (Aug. 25, 1988).

Stam, M., et al., "The Silence of Genes in Transgenic Plants", *Annals of Botany,* 79, 3–12 (1997).

Takai, T., et al., "Primary Structure of Chicken Liver Acetyl–CoA Carboxylase Deduced from cDNA Sequence", *Journal of Biological Chemistry,* 263, 2651–2657 (1988).

Turnham, E., et al., "Changes in the Activity of Acetyl–CoA Carboxylase During Rape–Seed Formation", *Biochem. J.,* 212, 223–229 (1983).

Vasil, I.K., "Progress in the Regeneration and Genetic Manipulation of Cereal Crops", *Bio/Technology,* 6, 398–402 (Apr. 1988).

Von Heijne, G., et al., "Domain Structure of Mitochondrial and Chloroplast Targeting Peptides", *Eur. J. Biochem.,* 180, 535–545 (1989).

Yamada, Y., "Tissue Culture Studies on Cereals", In: *Plant Cell, Tissue and Organ Culture,* Springer–Verlag, Berlin, 144–159 (1997).

L.C. Marshall et al., "Allelic Mutations in Acetyl–Coenzyme A Carblase Confer Herbicide Tolerance in Maize," *Theor. Appl. Genet.,* 83, 435–442 (1992.).

K.L. Van Dee Master's Thesis entitled "Evidence for Two Independently Segregating Loci Encoding Acetyl–CoA Carboxylase in *Zea Mays,"* 62 pages (Feb. 1, 1994).

"Mold Vegetables Growing Res Inst", Database WPI, Section Ch., Week 9307, Derwent Publications Ltd., London, GB, Class C06, AN 93–057074, (Mar. 23, 1992).

Caffrey, J.J., et al., "Genetic Mapping of Two Acatyl–COA Carboxylase Genes", *Maize Genetic Cooperation Newsletter,* vol. 69, Columbia US, pp. 3–4, (1995).

Vahlensieck, H.F., et al., "Identification of the yeast ACC1 gene product (acetyl–CoA carboxylase) as the target of the polyketide fungicide soraphen A", *Current Genetics,* vol. 25, pp. 95–100, (1994).

Van Dee, K., et al., "RFLP mapping of Accl in *Zea mays* L.", *Agronomy Abstracts,* Madison US—XP002051061, 198, (1992).

Marshall, L.C. et al., "Allelic Mutations in Acetyl–Coenzyme A Carboxylase Confer Herbicide Tolerance in Maize", *Theoretical and Applied Genetics,* vol. 83, No. 4, Berlin Germany, pp. 435–442, (1992).

Alrefai, R., et al., "Quantitative Trait Locus Analysis of Fatty Acid Concentrations in Maize", *Genome,* 38, 894–901 (1995).

Egli, M.A., et al., "Characterization of Maize Acetyl–Coenzyme A Carboxylase", *Plant Physiology,* 101, 499–506 (1993).

Elborough, K.M., et al., "Studies on Wheat Acetyl CoA Carboxylase and the Cloning of a Partial cDNA", *Plant Molecular Biology,* 24, 21–34 (1994).

A R Ashton, et al., "Molecular cloning of two different cDNAs for maize acetyl CoA carboxylase", *Plant Molecular Biology,* 24, 35–49 (1994).

M. A. Egli, et al., "A Maize Acetyl–Coenzyme A Carboxylase cDNA Sequence", *Plant Physiology,* 108, 1299–1300 (Jul. 1995).

M. A. Egli, et al., "A Maize Acetyl–CoA Carboxylase cDNA Maps to Chromosome 2S", *Plant Physiology,* 105 (1 suppl.), 64, (1994).

M. A. Egli, et al., "Characterization of Maize Acetyl–Coenzyme A Carboxylase", *Plant Physiol.,* 101, 499–506, (1993).

M. A. Egli, et al., "Cloning and Sequence Analysis of a Maize Acetyl–CoA Carboxylase Gene", *Plant Physiol.,* 102 (1 suppl.), 70, (1993).

B Gengenbach, et al., "Maize acetyl–coenzyme A carboxlyalse genes", In: *Plant Lipid Metabolism,* Kader, J.–C., et al (eds.), Kluwer Academic Press, Boston, pp. 43–45, (1995).

P Gornicki, et al., "Wheat acetyl–coenzyme A carboxylase: cDNA and protein structure", *Proc. Natl. Acad. Sci. USA,* 91, 6860–6864, (Jul. 1994).

K.R. Roesler, et al., "Structure and Expression of An Arabidopsis Acetyl–Coenzyme A Carboxylase Gene", *Plant Physiology*, 105, 611–617, (Jun. 1994).

Y. Sasaki, et al., "Chloroplast–Encoded Protein as a Subunit of Acetyl–CoA Carboxylase in Pea Plant", *J. of Biological Chemistry*, 268, 33, 25118–25123, (Nov. 25, 1993).

D. A. Somers, et al., "Expression of the ACC1 Gene–Encoded Acetyl–Coenzyme A Carboxylase in Developing Maize *Zea–Mays* L. Kernels", *Plant Physiol.*, 101, 1097–1101, (1993).

\* cited by examiner

```
   1  GGTCTTCAAT TGTGCTGTCT GGGCCACGGA ACGACAATGT CACAGCTTGG
  51  ATTAGCCGCA GCTGCCTCAA AGGCCTTGCC ACTACTCCCT AATCGCCAGA
 101  GAAGTTCAGC TGGGACTACA TTCTCATCAT CTTCATTATC GAGGCCCTTA
 151  AACAGAAGGA AAAGCCATAC TCGTTCACTC CGTGATGGCG GAGATGGGGT
 201  ATCAGATGCC AAAAAGCACA GCCAGTCTGT TCGTCAAGGT CTTGCTGGCA
 251  TTATCGACCT CCCAAGTGAG GCACCTTCCG AAGTGGATAT TTCACATGGA
 301  TCTGAGGATC CTAGGGGCC AACAGATTCT TATCAAATGA ATGGGATTAT
 351  CAATGAAACA CATAATGGAA GACATGCCTC AGTGTCCAAG GTTGTTGAAT
 401  TTTGTGCGGC ACTAGGTGGC AAAACACCAA TTCACAGTAT ATTAGTGGCC
 451  AACAATGGAA TGGCAGCAGC AAAATTTATG AGGAGTGTCC GGACATGGGC
 501  TAATGATACT TTTGGATCTG AGAAGGCAAT TCAACTCATA GCTATGGCAA
 551  CTCCGGAAGA CATGAGGATA AATGCAGAAC ACATTAGAAT TGCTGACCAA
 601  TTCGTAGAGG TGCCTGGTGG AACAAACAAT AATAACTACG CCAATGTTCA
 651  ACTCATAGTG GGGATGGCAC AAAAACTAGG TGTTTCTGCT GTTTGGCCTG
 701  GTTGGGGTCA TGCTTCTGAG AATCCTGAAC TGCCAGATGC ATTGACCGCA
 751  AAAGGGATCG TTTTTCTTGG CCCACCTGCA TCATCAATGA ATGCTTTGGG
 801  AGATAAGGTC GGCTCAGCTC TCATTGCTCA AGCAGCCGGG GTCCCAACTC
 851  TTGCTTGGAG TGGATCACAT GTTGAAGTTC CATTAGAGTG CTGCTTAGAC
 901  GCGATACCTG AGGAGATGTA TAGAAAAGCT TGCGTTACTA CCACAGAGGA
 951  AGCAGTTGCA AGTTGTCAAG TGGTTGGTTA TCCTGCCATG ATTAAGGCAT
1001  CCTGGGGAGG TGGTGGTAAA GGAATAAGAA AGGTTCATAA TGATGATGAG
1051  GTTAGAGCGC TGTTTAAGCA AGTACAAGGT GAAGTCCCTG CTCCCCAAT
1101  ATTTGTCATG AGGCTTGCAT CCCAGAGTCG GCATCTTGAA GTTCAGTTGC
1151  TTTGTGATCA ATATGGTAAT GTAGCAGCAC TTCACAGTCG TGATTGCAGT
1201  GTGCAACGGC GACACCAGAA GATTATTGAA GAAGGTCCAG TTACTGTTGC
1251  TCCTCGTGAG ACAGTTAAAG CACTTGAGCA GGCAGCAAGG AGGCTTGCTA
1301  AGGCTGTGGG TTATGTTGGT GCTGCTACTG TTGAGTATCT TTACAGCATG
1351  GAAACTGGAG ACTACTATTT TCTGGAACTT AATCCCCGAC TACAGGTTGA
1401  GCATCCAGTC ACTGAGTGGA TAGCTGAAGT GAATCTGCCT GCAGCTCAAG
1451  TTGCTGTTGG AATGGGCATA CCTCTTTGGC AGATTCCAGA AATCAGACGT
1501  TTCTATGGAA TGGACTATGG AGGAGGGTAT GACATTTGGA GGAAAACAGC
1551  AGCTCTTGCT ACACCATTTA ATTTTGATGA AGTAGATTCT CAATGGCCAA
1601  AGGGCCATTG TGTAGCAGTT AGAATTACTA GTGAGGACCC AGATGATGGT
1651  TTCAAACCTA CTGGTGGGAA AGTGAAGGAG ATAAGTTTTA AAAGCAAGCC
1701  TAATGTTTGG GCCTACTTCT CAGTAAAGTC TGGTGGAGGC ATTCATGAAT
1751  TTGCTGATTC TCAGTTTGGA CATGCTTTTG CATATGGACT CTCTAGACCA
```

FIG. 3A

1801 GCAGCTATAA CAAACATGTC TCTTGCATTA AAAGAGATTC AGATTCGTGG
1851 AGAAATTCAT TCAAATGTTG ATTACACAGT TGACCTCTTA AACGCTTCAG
1901 ACTTCAGAGA AAACAAGATC CACACTGGTT GGCTGGATAC AAGAATAGCT
1951 ATGCGTGTTC AAGCTGAGAG GCCCCCATGG TATATCTCAG TGGTTGGAGG
2001 TGCTTTATAT AAAACAGTAA CCACCAATGC AGCCACTGTT TCTGAATATG
2051 TTAGTTATCT CACCAAGGGC CATATTCCAC CAAAGCATAT ATCCCTTGTC
2101 AATTCTACAG TTAATTTGAA TATAGAAGGG AGCAAATACA CAATTGAAAC
2151 TGTAAGGACT GGACATGGTA GCTACAGGTT GAGAATGAAT GATTCAACAG
2201 TTGAAGCGAA TGTACAATCT TTATGTGATG GTGGCCTCTT AATGCAGTTG
2251 GATGGAAACA GCCATGTAAT TTATGCAGAA GAAGAAGCTG GTGGTACACG
2301 GCTTCAGATT GATGGAAAGA CATGTTTATT GCAGAATGAC CATGATCCAT
2351 CGAAGTTATT AGCTGAGACA CCCTGCAAAC TTCTTCGTTT CTTGGTTGCT
2401 GATGGTGCTC ATGTTGATGC GGATGTACCA TACGCGGAAG TTGAGGTTAT
2451 GAAGATGTGC ATGCCTCTCT TGTCACCTGC TTCTGGTGTC ATTCATTGTA
2501 TGATGTCTGA GGGCCAGGCA TTGCAGGCTG GTGATCTTAT AGCAAGGTTG
2551 GATCTTGATG ACCCTTCTGC TGTGAAAAGA GCTGAGCCAT TGATGGAAT
2601 ATTTCCACAA ATGGAGCTCC CTGTTGCTGT CTCTAGTCAA GTACACAAAA
2651 GATATGCTGC AAGTTTGAAT GCTGCTCGAA TGGTCCTTGC AGGATATGAG
2701 CACAATATTA ATGAAGTCGT TCAAGATTTG GTATGCTGCC TGGACAACCC
2751 TGAGCTTCCT TTCCTACAGT GGGATGAACT TATGTCTGTT CTAGCAACGA
2801 GGCTTCCAAG AAATCTCAAG AGTGAGTTAG AGGATAAATA CAAGGAATAC
2851 AAGTTGAATT TTTACCATGG AAAAAACGAG GACTTTCCAT CCAAGTTGCT
2901 AAGAGACATC ATTGAGGAAA ATCTTTCTTA TGGTTCAGAG AAGGAAAAGG
2951 CTACAAATGA GAGGCTTGTT GAGCCTCTTA TGAACCTACT GAAGTCATAT
3001 GAGGGTGGGA GAGAGAGCCA TGCACATTTT GTTGTCAAGT CTCTTTTCGA
3051 GGAGTATCTT ACAGTGGAAG AACTTTTTAG TGATGGCATT CAGTCTGACG
3101 TGATTGAAAC ATTGCGGCAT CAGCACAGTA AAGACCTGCA GAAGGTTGTA
3151 GACATTGTGT TGTCTCACCA GGGTGTGAGG AACAAAGCTA AGCTTGTAAC
3201 GGCACTTATG GAAAAGCTGG TTTATCCAAA TCCTGGTGGT TACAGGGATC
3251 TGTTAGTTCG CTTTTCTTCC CTCAATCATA AAAGATATTA TAAGTTGGCC
3301 CTTAAAGCAA GTGAACTTCT TGAACAAACC AAACTAAGTG AACTCCGTGC
3351 AAGCGTTGCA AGAAGCCTTT CGGATCTGGG GATGCATAAG GGAGAAATGA
3401 GTATTAAGGA TAACATGGAA GATTTAGTCT CTGCCCCATT ACCTGTTGAA
3451 GATGCTCTGA TTTCTTTGTT TGATTACAGT GATCGAACTG TTCAGCAGAA
3501 AGTGATTGAG ACATACATAT CACGATTGTA CCAGCCTCAT CTTGTAAAGG
3551 ATAGCATCCA AATGAAATTC AAGGAATCTG GTGCTATTAC TTTTTGGGAA

FIG. 3B

```
3601  TTTTATGAAG GGCATGTTGA TACTAGAAAT GGACATGGGG CTATTATTGG
3651  TGGGAAGCGA TGGGGTGCCA TGGTCGTTCT CAAATCACTT GAATCTGCGT
3701  CAACAGCCAT TGTGGCTGCA TTAAAGGATT CGGCACAGTT CAACAGCTCT
3751  GAGGGCAACA TGATGCACAT TGCATTATTG AGTGCTGAAA ATGAAAGTAA
3801  TATAAGTGGA ATAAGCAGTG ATGATCAAGC TCAACATAAG ATGGAAAAGC
3851  TTAGCAAGAT ACTGAAGGAT ACTAGCGTTG CAAGTGATCT CCAAGCTGCT
3901  GGTTTGAAGG TTATAAGTTG CATTGTTCAA AGAGATGAAG CTCGCATGCC
3951  AATGCGCCAC ACATTCCTCT GGTTGGATGA CAAGAGTTGT TATGAAGAAG
4001  AGCAGATTCT CCGGCATGTG GAGCCTCCCC TCTCTACACT TCTTGAATTG
4051  GATAAGTTGA AGGTGAAAGG ATACAATGAA ATGAAGTATA CTCCTTCGCG
4101  TGACCGCCAA TGGCATATCT ACACACTAAG AAATACTGAA AACCCCAAAA
4151  TGTTGCATAG GGTGTTTTC CGAACTATTG TCAGGCAACC CAATGCAGGC
4201  AACAAGTTTA GATCGGCTCA GATCAGCGAC GCTGAGGTAG GATGTCCCGA
4251  AGAATCTCTT TCATTTACAT CAAATAGCAT CTTAAGATCA TTGATGACTG
4301  CTATTGAAGA ATTAGAGCTT CATGCAATTA GGACAGGTCA TTCTCACATG
4351  TATTTGTGCA TACTGAAAGA GCAAAAGCTT CTTGACCTCA TTCCATTTTC
4401  AGGGAGTACA ATTGTTGATG TTGGCCAAGA TGAAGCTACC GCTTGTTCAC
4451  TTTTAAAATC AATGGCTTTG AAGATACATG AGCTTGTTGG TGCAAGGATG
4501  CATCATCTGT CTGTATGCCA GTGGGAGGTG AAACTCAAGT TGGACTGTGA
4551  TGGCCCTGCA AGTGGTACCT GGAGAGTTGT AACTACAAAT GTTACTGGTC
4601  ACACCTGCAC CATTGATATA TACCGAGAAG TGGAGGAAAT AGAATCACAG
4651  AAGTTAGTGT ACCATTCAGC CAGTTCGTCA GCTGGACCAT TGCATGGTGT
4701  TGCACTGAAT AATCCATATC AACCTTTGAG TGTGATTGAT CTAAAGCGCT
4751  GCTCTGCTAG GAACAACAGA ACAACATATT GCTATGATTT TCCGCTGGCC
4801  TTTGAAACTG CACTGCAGAA GTCATGGCAG TCCAATGGCT CTACTGTTTC
4851  TGAAGGCAAT GAAAATAGTA AATCCTACGT GAAGGCAACT GAGCTAGTGT
4901  TTGCTGAAAA ACATGGGTCC TGGGGCACTC CTATAATTCC GATGGAACGC
4951  CCTGCTGGGC TCAACGACAT TGGTATGGTC GCTTGGATCA TGGAGATGTC
5001  AACACCTGAA TTTCCCAATG GCAGGCAGAT TATTGTTGTA GCAAATGATA
5051  TCACTTTCAG AGCTGGATCA TTTGGCCCAA GGGAAGATGC ATTTTTTGAA
5101  ACTGTCACTA ACCTGGCTTG CGAAAGGAAA CTTCCTCTTA TATACTTGGC
5151  AGCAAACTCT GGTGCTAGGA TTGGCATAGC TGATGAAGTA AAATCTTGCT
5201  TCCGTGTTGG ATGGTCTGAC GAAGGCAGTC CTGAACGAGG GTTTCAGTAC
5251  ATCTATCTGA CTGAAGAAGA CTATGCTCGC ATTAGCTCTT CTGTTATAGC
5301  ACATAAGCTG GAGCTAGATA GTGGTGAAAT TAGGTGGATT ATTGACTCTG
5351  TTGTGGGCAA GGAGGATGGG CTTGGTGTCG AGAACATACA TGGAAGTGCT
```

FIG. 3C

```
5401  GCTATTGCCA GTGCTTATTC TAGGGCATAT GAGGAGACAT TTACACTTAC
5451  ATTTGTGACT GGGCGGACTG TAGGAATAGG AGCTTATCTT GCTCGACTTG
5501  GTATACGGTG CATACAGCGT CTTGACCAGC CTATTATTTT AACAGGGTTT
5551  TCTGCCCTGA ACAAGCTCCT TGGGCGGGAA GTGTACAGCT CCCACATGCA
5601  GCTTGGTGGT CCTAAGATCA TGGCGACCAA TGGTGTTGTC CACCTCACTG
5651  TTCCAGATGT CCTTGAAGGT GTTCCAATA TATTGAGGTG GCTCAGCTAT
5701  GTTCCTGCAA ACATTGGTGG ACCTCTTCCT ATTACCAAAC CTCTGGACCC
5751  TCCAGACAGA CCTGTTGCTT ACATCCCTGA GAACACATGC GATCCACGTG
5801  CAGCTATCTG TGGTGTAGAT GACAGCCAAG GGAAATGGTT GGGTGGTATG
5851  TTTGACAAAG ACAGCTTTGT GGAGACATTT GAAGGATGGG CAAAAACAGT
5901  GGTTACTGGC AGAGCAAAGC TTGGAGGAAT TCCTGTGGGC GTCATAGCTG
5951  TGGAGACACA GACCATGATG CAGATCATCC CTGCTGATCC AGGTCAGCTT
6001  GATTCCCATG AGCGATCTGT CCCTCGTGCT GGACAAGTGT GGTTCCCAGA
6051  TTCTGCAACC AAGACCGCTC AGGCATTATT AGACTTCAAC CGTGAAGGAT
6101  TGCCTCTGTT CATCCTGGCT AATTGGAGAG GCTTCTCTGG TGGACAAAGA
6151  GATCTCTTTG AAGGAATTCT TCAGGCTGGG TCAACAATTG TCGAGAACCT
6201  TAGGACATAT AATCAGCCTG CTTTTGTGTA CATTCCTATG GCTGGAGAGC
6251  TTCGTGGAGG AGCTTGGGTT GTGGTCGATA GCAAATAAA TCCAGACCGC
6301  ATTGAGTGTT ATGCTGAAAG GACTGCCAAA GGTAATGTTC TCGAACCTCA
6351  AGGGTTAATT GAAATCAAGT TCAGGTCAGA GGAACTCCAA GACTGTATGG
6401  GTAGGCTTGA CCCAGAGTTG ATAAATCTGA AAGCAAAACT CCAAGATGTA
6451  AATCATGGAA ATGGAAGTCT ACCAGACATA GAAGGGATTC GGAAGAGTAT
6501  AGAAGCACGT ACGAAACAGT TGCTGCCTTT ATATACCCAG ATTGCAATAC
6551  GGTTTGCTGA ATTGCATGAT ACTTCCCTAA GAATGGCAGC TAAAGGTGTG
6601  ATTAAGAAAG TTGTAGACTG GAAGAATCA CGCTCGTTCT TCTATAAAAG
6651  GCTACGGAGG AGGATCGCAG AAGATGTTCT TGCAAAAGAA ATAAGGCAGA
6701  TAGTCGGTGA TAAATTTACG CACCAATTAG CAATGGAGCT CATCAAGGAA
6751  TGGTACCTTG CTTCTCAGGC CACAACAGGA AGCACTGGAT GGGATGACGA
6801  TGATGCTTTT GTTGCCTGGA AGGACAGTCC TGAAAACTAC AAGGGGCATA
6851  TCCAAAAGCT TAGGGCTCAA AAAGTGTCTC ATTCGCTCTC TGATCTTGCT
6901  GACTCCAGTT CAGATCTGCA AGCATTCTCG CAGGGTCTTT CTACGCTATT
6951  AGATAAGATG GATCCCTCTC AGAGAGCGAA GTTTGTTCAG GAAGTCAAGA
7001  AGGTCCTTGA TTGATGATAC CAACACATCC AACACAATGT GTGCATGTCA
7051  CATCTTTTTG TTCTAGTACA TACATAGAAG GATATTGCTT GGTCTTGATT
7101  GATCATGTCT GATTTAAGTC GACTATTATT TCTTGGAATT TTCTTTTGGA
7151  CCTGGTGCTA TGGTTGATGG ATGTATATTG GATATGTGCG TTCTGCCAGG
```

FIG. 3D

```
7201  TGTAAGCACA AAGGTTTAGA CARAMMRARA RCAAGAGCGA GTGAACCTGT
7251  TCTGGTTTTG CAGTGGTTCA GTAAGGCAGA AAGTTGTTAA ACCGTAGTTC
7301  TGAGATGTAT TACCAGTGNC GCCATGCTGT ACTTTTAGGG TGTATAATGC
7351  GGATACAAAT AAACAATTTA GCGGTTCATT AAAGTTTGAA CTCAAATAAC
7401  ATGTTCTTTG TAAGCATATG TACCGTACCT CTACGTGAAA TAAAGTTGTT
7451  GAATTAGCAT TCGAAAAAAA
```

FIG. 3E

```
   1  MSQLGLAAAA  SKALPLLPNR  QRSSAGTTFS  SSSLSRPLNR  RKSHTRSLRD
  51  GGDGVSDAKK  HSQSVRQGLA  GIIDLPSEAP  SEVDISHGSE  DPRGPTDSYQ
 101  MNGIINETHN  GRHASVSKVV  EFCAALGGKT  PIHSILVANN  GMAAAKFMRS
 151  VRTWANDTFG  SEKAIQLIAM  ATPEDMRINA  EHIRIADQFV  EVPGGTNNNN
 201  YANVQLIVGM  AQKLGVSAVW  PGWGHASENP  ELPDALTAKG  IVFLGPPASS
 251  MNALGDKVGS  ALIAQAAGVP  TLAWSGSHVE  VPLECCLDAI  PEEMYRKACV
 301  TTTEEAVASC  QVVGYPAMIK  ASWGGGGKGI  RKVHNDDEVR  ALFKQVQGEV
 351  PGSPIFVMRL  ASQSRHLEVQ  LLCDQYGNVA  ALHSRDCSVQ  RRHQKIIEEG
 401  PVTVAPRETV  KALEQAARRL  AKAVGYVGAA  TVEYLYSMET  GDYYFLELNP
 451  RLQVEHPVTE  WIAEVNLPAA  QVAVGMGIPL  WQIPEIRRFY  GMDYGGGYDI
 501  WRKTAALATP  FNFDEVDSQW  PKGHCVAVRI  TSEDPDDGFK  PTGGKVKEIS
 551  FKSKPNVWAY  FSVKSGGGIH  EFADSQFGHA  FAYGLSRPAA  ITNMSLALKE
 601  IQIRGEIHSN  VDYTVDLLNA  SDFRENKIHT  GWLDTRIAMR  VQAERPPWYI
 651  SVVGGALYKT  VTTNAATVSE  YVSYLTKGHI  PPKHISLVNS  TVNLNIEGSK
 701  YTIETVRTGH  GSYRLMNDS   TVEANVQSLC  DGGLLMQLDG  NSHVIYAEEE
 751  AGGTRLQIDG  KTCLLQNDHD  PSKLLAETPC  KLLRFLVADG  AHVDADVPYA
 801  EVEVMKMCMP  LLSPASGVIH  CMMSEGQALQ  AGDLIARLDL  DDPSAVKRAE
 851  PFDGIFPQME  LPVAVSSQVH  KRYAASLNAA  RMVLAGYEHN  INEVVQDLVC
 901  CLDNPELPFL  QWDELMSVLA  TRLPRNLKSE  LEDKYKEYKL  NFYHGKNEDF
 951  PSKLLRDIIE  ENLSYGSEKE  KATNERLVEP  LMNLLKSYEG  GRESHAHFVV
1001  KSLFEEYLTV  EELFSDGIQS  DVIETLRHQH  SKDLQKVVDI  VLSHQGVRNK
1051  AKLVTALMEK  LVYPNPGGYR  DLLVRFSSLN  HKRYYKLALK  ASELLEQTKL
1101  SELRASVARS  LSDLGMHKGE  MSIKDNMEDL  VSAPLPVEDA  LISLFDYSDR
1151  TVQQKVIETY  ISRLYQPHLV  KDSIQMKFKE  SGAITFWEFY  EGHVDTRNGH
1201  GAIIGGKRWG  AMVVLKSLES  ASTAIVAALK  DSAQFNSSEG  NMMHIALLSA
1251  ENESNISGIS  SDDQAHKME   KLSKILKDTS  VASDLQAAGL  KVISCIVQRD
1301  EARMPMRHTF  LWLDDKSCYE  EEQILRHVEP  PLSTLLELDK  LKVKGYNEMK
1351  YTPSRDRQWH  IYTLRNTENP  KMLHRVFFRT  IVRQPNAGNK  FRSAQISDAE
1401  VGCPEESLSF  TSNSILRSLM  TAIEELELHA  IRTGHSHMYL  CILKEQKLLD
1451  LIPFSGSTIV  DVGQDEATAC  SLLKSMALKI  HELVGARMHH  LSVCQWEVKL
1501  KLDCDGPASG  TWRVVTTNVT  GHTCTIDIYR  EVEEIESQKL  VYHSASSSAG
1551  PLHGVALNNP  YQPLSVIDLK  RCSARNNRTT  YCYDFPLAFE  TALQKSWQSN
1601  GSTVSEGNEN  SKSYVKATEL  VFAEKHGSWG  TPIIPMERPA  GLNDIGMVAW
1651  IMEMSTPEFP  NGRQIIVVAN  DITFRAGSFG  PREDAFFETV  TNLACERKLP
1701  LIYLAANSGA  RIGIADEVKS  CFRVGWSDEG  SPERGFQYIY  LTEEDYARIS
1751  SSVIAHKLEL  DSGEIRWIID  SVVGKEDGLG  VENIHGSAAI  ASAYSRAYEE
```

FIG. 4A

```
1801  TFTLTFVTGR  TVGIGAYLAR  LGIRCIQRLD  QPIILTGFSA  LNKLLGREVY
1851  SSHMQLGGPK  IMATNGVVHL  TVPDVLEGVS  NILRWLSYVP  ANIGGPLPIT
1901  KPLDPPDRPV  AYIPENTCDP  RAAICGVDDS  QGKWLGGMFD  KDSFVETFEG
1951  WAKTVVTGRA  KLGGIPVGVI  AVETQTMMQI  IPADPGQLDS  HERSVPRAGQ
2001  VWFPDSATKT  AQALLDFNRE  GLPLFILANW  RGFSGGQRDL  FEGILQAGST
2051  IVENLRTYNQ  PAFVYIPMAG  ELRGGAWVVV  DSKINPDRIE  CYAERTAKGN
2101  VLEPQGLIEI  KFRSEELQDC  MGRLDPELIN  LKAKLQDVNH  GNGSLPDIEG
2151  IRKSIEARTK  QLLPLYTQIA  IRFAELHDTS  LRMAAKGVIK  KVVDWEESRS
2201  FFYKRLRRRI  AEDVLAKEIR  QIVGDKFTHQ  LAMELIKEWY  LASQATTGST
2251  GWDDDDAFVA  WKDSPENYKG  HIQKLRAQKV  SHSLSDLADS  SSDLQAFSQG
2301  LSTLLDKMDP  SQRAKFVQEV  KKVLD
```

FIG. 4B

```
   1  AAGCTTGGTA  TGGATTCgTC  AGCGCCAAgC  CGGGGTTTTG  CATGCGCCCg
  51  ACTGGaArCs  GAATTCCgTg  AgCCCtGTaC  rrCaATGGCA  ACCCCAsGGT
 101  TACTggGGTG  GCTGAATGGT  CTCsGCTTAC  GCAATTGTTT  GTGGCAgCwG
 151  CGTGGGCTAA  ATGTArGTTG  TCTCTTGTTG  CACTGCArGA  TGGATGGGTA
 201  gCCTCTGGGC  CGCCTCTGCT  ArTGTCTArC  GtTTGCTGAC  TGTGGTTTA.
 251  tCAgGGATGc  CCATgcCCAT  GcTAgATTGA  tAgCTgCCAt  TCtAATgGTA
 301  gGTGgcgGTA  AGGTTTATTA  AgCTGtAgtA  TCagTAgGTA  ACCTCATGAA
 351  tCAgGGTTTA  aGCACACCtT  TTCCTTTGTg  TgGGTgCATA  AgGAAtGCAC
 401  TTGGCtTCgT  TCCCtGAtAg  TCtTTGCtCA  TgTgTCATTC  TACCAAgTgG
 451  GTTACtgTAA  CAtTGCACTC  TATGATGGTT  GGTGGTtGTG  CATCTTTtTG
 501  CTtCCCCTGG  tTGTCTAATA  CCTGCATGTa  ACTGATGACC  ttCtTTTATG
 551  TATCATATAg  ATTACATCCT  TTTGTTGTAC  ATCTCAATTC  TGAAAAAACA
 601  ATGTTTTGCA  TTCTTAGCGc  TCTGTGCaCA  AgGaAAagGa  gGTTTTACCT
 651  gCAAcTtTTT  TTTTCgAGAA  AAAACAAACC  TTTCTGAAag  GCAGTGATCA
 701  TTTAGtATAA  AGAAAATTTG  ATTTACTTTC  TTCAGAGAGA  AtATkCCAAr
 751  CAAACAATTT  TCTTACTGTC  TGAGCCACGA  AATTTGATCT  TGATCtTACT
 801  TTCACAAGCC  ACATGAAGCC  tTATCATCGC  TcTGATAAaA  AAgCcaaaTa
 851  GGtGAttcAt  aGaAtGaGag  aAaGAacCTg  TTgCCaTTTG  GGGrCCtTGT
 901  TGTGTACTCA  ttAtCCCCCC  TGCtCAGGTT  GaGGtTTTcC  TTGccaCTGC
 951  CACCCCtTGG  CCCCTtCTTA  tACAAcCATC  TCcAttGaaA  aAGAtTTTgC
1001  aCtACAtTTG  GGCtcGtATG  aCaaaaaAGG  aAAAtaAAaC  TaaaCAGCAG
1051  AAACATAGTA  TaATTATAgG  TAAAAGGTTc  TGGCAAGTTT  GAGTGGaAGA
1101  GACCTTTGTA  TATTTGGACA  TATTTCACTA  GTAAATAGTT  TTCTAAAATc
1151  TTCATGAATG  GTGGCCAATA  AACTTGATAA  GATCTCAACA  TGGCAGGTTC
1201  CTTCmAAATG  AGAGGAAAAC  TGGAAACATC  ACAAATATTT  TTTAGCGAGT
1251  GGCCTATAAA  TTATAATGTT  GCTttcAttt  CttTGAtaTt  caAaACtTCc
1301  taAgAGtatt  ctgcTAGAGC  TCTGATGGTG  TCTTTTGCCT  CTGTCAGATT
1351  TTCCAGGaGT  TTTCTTCCCT  TTTtATGGca  CTGTGCGtTT  GaGaaGgTct
1401  TCAATTgTgC  TGtCTGGgCC  acGGaaCGAC  AAtgtcAcAg  ctTGGATTAg
1451  ccgcAgctgC  ctCAaaGGcc  TTgcCaCTAC  tCccTAATCG  ccAGAGaAGt
1501  TCAgCTGGGa  CtAcATTCTc  ATCAtcttCA  ttAtcGAGGC  CCtTAaAcAG
1551  aagCaAAagC  CaTAcTCGtT  CACtCcGTGA  TGgCGgAgaT  GGgGTATcAG
1601  ATgCCaAAAA  GCACAgCCAG  TCTGTTCgTC  aAGGTactGt  GAATATCTtt
1651  tgatACAAgc  taaAATtttg  ctaCAgaAtA  tatatTaAAG  AGttCttTCt
1701  TGGctgGtgt  tGtttAttT.  GttttaA.cA  tgcgaaagGg  CctctAgttg
1751  agttggttAg  gtggCCTGAa  tACCACTCCt  TAagGTCTTG  AgtttG..at
1801  TTtCCgtCGG  AgCGAaTttt  AGGCTAgGGt  TACCcCccCA  CCcCCAcCcG
1851  AAtCTGCACA  gtccggtcgt  ggtcgtcctc  atataggcta  cGatgtcatt
1901  GtgTATCGGC  GGgcCAggGG  TTTAAGAgTT  TTCTTGAcCT  TTGTTAGAAg
1951  ATCTTAATAA  TACAAtgTCC  AAGGGCTGTC  TTACCCTGTA  GGTCGAGTTT
2001  TTAGTTGTTT  TAACATGGTA  ATGTTTGAAG  CCTCATTCTA  GgtaCCAATA
2051  TAGATATCGt  cactgctcag  tttcaaatgt  ttgtctgcat  gtaggtcttg
2101  ctGGcattat  CGaCctcCca  AGtgaggCaC  CttcCGaaGT  GGAtAtTTCa
2151  CAGtaAgGac  taCAatatt   TGCGtacgTT  TG.TTtTGGa  aaaaGaAaAT
2201  AtTCtCAgct  tAtttatact  AgCttcgCtA  A.TacTGaaA  ..TgCtGtCt
2251  TaATGtCCTG  GT.GCTGtAT  GCTCaAtCTT  TCATAGtAAA  TgCTgCaaaa
2301  taTGTGAtGT  AaCTGTTGCA  ACACAGCCAG  GGaCCTGTTA  TTTAGAGCAT
```

FIG. 5A

| | | | | | |
|---|---|---|---|---|---|
| 2351 | GGTGAATGcT | CTGGTTCAGt | tAtATGATGT | AGTTATAGCT | CATGtTGaAG |
| 2401 | aAtTAGttGc | AgtGttTGCt | ggacaatggt | cacttatTat | aaatcataTc |
| 2451 | tgcatacaCa | TTtgTGacTt | CTgttgctGt | AAAtgCCCgc | atTttTTGAG |
| 2501 | aaaAaTTTaa | ATGctTGgcC | taaaTTGGac | ATAtATGAtA | GACaccaAgC |
| 2551 | TGatTTGaAC | TtTGttTatt | tttgacatcC | atgCAtAtTg | tcAgtgTtGT |
| 2601 | GAAAacaata | cTAatCctttT | tTtttTGtCt | ttTtCcaGTg | gAtctgaGGA |
| 2651 | TCcTAGGGGg | CCAACAGATT | CTTATCAAAt | GaatGGGaTT | ATCaAtGaAA |
| 2701 | CaCaTaaTgg | aagAcatgCc | TCaGTGTCCa | aGGttGTtga | aTTTTgtgcg |
| 2751 | gcaCtAGgtg | gcaaAaCACC | AATTCACaGT | ATATTAGTGG | CCaACAATGG |
| 2801 | aATgGCAgca | gcaaAattta | TGagGaGTGT | cCgGACATgG | GCtAaTgATA |
| 2851 | ctTTtgGAtC | TGagaAgGCA | AttCAActCA | TAgCTATgGC | AACTCCGgaA |
| 2901 | gACATGAgGA | TAaAtgCAGa | ACACAttAGA | ATTGCTGACC | AATT.CGTAG |
| 2951 | AGGTGCCTGG | TGGAACaAAC | AATAATAACT | ACG.CCAATG | TTCAACTCAT |
| 3001 | AGTGGAGGTT | AGCCTTGCTA | ATCTGTTAGT | TTACTACTGG | TCTGCTGTTT |
| 3051 | CCTTTATTTG | TTGTATAATG | ATTGACATAT | TTAAGTAGAG | AAATTTATAT |
| 3101 | TTCTCCTCTG | CTGTTGTGGA | AGTCCAATTG | TCATCATTAA | CTGTGAAATA |
| 3151 | TTGCAGATGG | CACAAAAACT | AGGTGTTTCT | GCTGtTTGGC | CTGGTTGGGG |
| 3201 | TCATGCTTCT | GAGAATCCTG | AACTGCCAGA | TGCATTGACC | GCAAAAGGGA |
| 3251 | TCGTTTTTCT | TGGCCCACCT | GcATCATCAA | TGAATGCTTT | GGGAGaTAAG |
| 3301 | gTCgGCTCAG | CTCTCaTTgC | TCAAgCagcC | GGggtCCCaA | CTCT.TgCTT |
| 3351 | gGAgTgGATC | ACATGTGAgT | CTCACTCTTT | gAtTACTAtC | CgCCTGTCTC |
| 3401 | AtTgCTCTCt | CtttCAtATT | CTAATgACaC | taAATtTAGG | TTGaaGTtcC |
| 3451 | AtTAGagtgc | TGCTtAGacG | cGATAcCTGA | GGAGATGtAt | AGAaAAgcTT |
| 3501 | ATCGATaCCk | TcgACctCGA | GGGgGGgccc | gGTaCyAgCT | GsTG |

FIG. 5B

```
   1  GAATTCCGTG  AGCCCTGTAC  GGCAATGGCA  ACCCCAGGGT  TACTGGGGTG
  51  GCTGAATGGT  CTCGGCTTAC  GCAATTGTTT  GTGGCAGCTG  CGTGGGCTAA
 101  ATGTAGGTTG  TCTCTTGTTG  CACTGCAGGA  TGGATGGGTA  GCCTCTGGGC
 151  CGCCTCTGCT  AGTGTCTAGC  GTTGCTGACT  GTGGTTTATT  CAGGGATGCC
 201  ATGcCCATGC  TAGATTGATA  GGTCATAGGT  GCCATTCTAA  TGGTAGGTGG
 251  CGGTAAGGTT  TATTAAGCTG  TCGTATCAGT  AGGTAACCTC  ATGAATCAGG
 301  GTTTAAGCCC  ACCTTCTCCT  TTGTGTGGGT  GCATAAGGAA  TGCACTTGGC
 351  TTCGTTCCCT  GCTAGTCTTT  GCTCATGTGT  CATTCTACCA  AGTGGGTTAC
 401  TGTAACATTG  CACTCTATGA  TGGTTGGTGG  TTGTGCATCT  TTTTGCTTCC
 451  CCTGGTTGTC  TAATACCTGc  ATGTAAcTGA  TGACcTTCTT  TTATGTATCA
 501  TATAGATtAc  ATcCTTTTGT  TGtACATcTC  AATTCTGAAA  AaCAATGTTT
 551  TGCATTCTTA  GCGcTCTGTG  CACAAGGAAA  AGGAgGTTTT  ACCTGCAAcT
 601  TTTTTTTTCg  AgAAAAAACA  AACCTTTCTG  AAAgGCAGTG  ATCATTTAgT
 651  ATAAAgAAAA  TTTGAtTTAC  TTtCTtCAga  ArAgAATAtT  CCAAACAAAC
 701  aATTTTCTTA  CAgTcTGAGC  CACGAAATTT  GATCTTGATC  TTACtTTCaC
 751  AAGCCACATG  AAGCCTTATC  ATCGCTCTGA  TAAAAAAACC  AAATAGGTGA
 801  TTCATAGAAT  GAGAAAAAGA  ACCTGTTGCC  ATTTGGGGAC  CTTGTTGTGT
 851  ACTCATTATC  CCCCCTGCTC  AGGTTGAGGT  TT.CCTTGCC  ACTGCCACCC
 901  CTTGGCCCCT  TCTTATACAA  CCATCTCCAT  TGAAAAAGAT  TTTGCACTAC
 951  ATTTGGGcTT  cGTAtAaCaA  AAAAGGaAAA  TaAAAcTAAA  CAGCAGaAAC
1001  ATAGTATAAT  TATAGgTAAA  AGGTTcTGGC  AAGTTTGAGT  GGTAGAGACC
1051  TTTGTATATT  TGGACATATT  TCACTAGTAA  ATAGTTTTCT  AAAATgTTCA
1101  TGAATGGTGG  CCAATAAACT  TGATAAGATC  TCAACATGGC  AGGTTCCTTC
1151  AAAATGAGAG  GaAAACTGGA  AACATCACAA  ATATTTTTTA  GCGAGTGGCC
1201  TATAAATTAT  AATGTTGCTT  TCATTTCTTT  GATATTCAAA  AcTTCCTAAG
1251  AGTATTcTGC  TAGAGCtTCT  GATGGTGTCT  TTtGCcTCTG  TCAGATTTTC
1301  CAGGaG.TTT  TcTTCCCTTT  TTATGGCACT  GTGGTTTGAG  AAGGTTTCAA
1351  TTGTGCTGTC  TGGGCCACGG  AACGACAATG  TCACAGCTTG  GATTAGCCGC
1401  AGCTGCCTCA  AAGGCCTTGC  CACTACTCCC  TAATCGCCAG  AGAAGTTCAG
1451  CTGGGACTAC  ATTCTCATCA  TcTTCATTAT  CGAGGCCCTT  AAACAGAAGG
1501  AAAAGCCGTA  CTCGTTCACT  CCGTGATGGC  GGAGATGGGG  TATCAGATGC
1551  CAAAAAGCAC  AGCCAGTCTG  TTcGTCAAGG  TACTGTGAAT  AtCTTTTGAT
1601  ACAAGCTAAA  ATTTGCTAC  AGAATATATA  TTAAAGAGTT  CTTTCTTGGc
1651  TGGtGTTGTT  TATTTGTTTT  AACATGCGAA  AgGGCcTCTA  gTTGAGTTGG
1701  TTAGGTGGCC  TGAGTACCAc  TCCTTAAGGT  CTTGAGTTTG  ATTTTCCGTC
1751  AgAGCGAATT  TTAGGcTAGG  GTtaCCCCCC  ACCCCCCCAC  CCCTACCCGA
1801  ATcTGCACAg  TCCGGTCGTG  GTCGTCCTCA  TATAgGCTAC  gATGTCATTG
1851  TGTATCGGCG  GGCCAGGGGT  TTAAgAgTTT  tCTTGACCTT  TGTGAgAAgA
1901  TcTTAATAAT  ACAATGTCCA  AgAgCTGTCt  TACCCTGTAG  GTCrAgTTTT
1951  TTAgTTGTTT  TAACATGGTT  ATgTTTGAAg  CCTCAtTCtA  gGTAcCAATA
2001  TArATATgCt  CaCTGCTCAg  TTTCmAATGt  TTGTCTGCAT  kTAgGTCtTG
2051  CTGGCATTAT  CGACCTCCCA  AGTGAGGCAC  CTTCCGAAGT  GGATATTTCA
2101  CAGTAAGGAn  TACAGTATTT  TGCGTACGTT  TGTTTTGGAA  AAAGAAATAT
2151  TCTCAGCTTA  TTTAAT
```

FIG. 6

```
  1  GAATTCCTGT  GGGTGTCATA  GCTGTGGAGA  CACAGACCAT  GATGCAGATC
 51  CTGTAATACT  TCAAAATCTT  AAGCCACAAA  ACTTGATTAA  TTGTTAGCAC
101  AGTAATTTGC  CAAGTGGCTA  GAGAAgGATC  TCAACACAAC  ACAATAACCA
151  AGAGATATCA  ATCACAGAGA  TGGCACGGTG  GTTATCCCGT  GGTTCGGCCA
201  AGACCAACGC  TTGCCTACTC  CACGTTGTGG  CGTCCCAACG  GACGAGGGTT
251  GCAATCAACC  CCTCTCAAGC  GGTCCAAAGA  CCAACTTGAA  TACCACGGTG
301  TTGCTTTGCT  TTTCTTAATC  CCACTTGCGA  GGAATCTCCA  CAGCTTGGAG
351  CCTCTCGCCC  TTTCAAAAGA  TTTCACAAAG  AATCACGGAg  CAAGGGAAGG
401  ATCAACAACT  CACACACgAC  ACAAAGATCA  CAGTGAATAC  GCACACATAA
451  AACCAAGACT  TGAgCTCAAg  TGACTAGCAC  ACTT
```

FIG. 7A

```
  1  ATGGAaGTGT  GTATTGCCAG  TGcTTaTTyT  rGGGATATGA  GGGAATTwAm
 51  ATTAcATTTG  TGAcTGGGCG  GACTGTAGGA  TAGGAGTTAT  CTTGyTcGAT
101  TGGTATACGG  TGCATACAGs  kyTTGACCAG  CTATTATTTT  AACAGGgTTT
151  TCTGCCCTGA  ACAAGTCCTT  GGGCGGGAAG  TGTACAGcTC  CCACATGCAG
201  CTTGGTGGTC  CTAAGATCAT  GGCGACCAAT  GGTGTTGTCC  ACCTCACTGT
251  TCCAGATGAC  CTTGAAGGTG  TTTCCAATAT  ATTGAGGTGG  CTCAGCTATG
301  TTCCTGCAAA  CATTGGTGGA  CCTcTTCCTA  TTACCAAACC  TCTGGACCCT
351  CCAGACAGAC  CTGTTGCTTA  CATCCCTGAG  AACACATGCG  ATCCACGTGC
401  AGCTATCTGT  GGTGTAGATG  ACAGCCAAGG  GAAATGGTTG  GGTGGTATGT
451  TTGACAAAGA  CAGCTTTGTG  GAGACATTTG  AAGGATGGGC  AAAAACAGTG
501  GTTACTGGCA  GAGCAAAGCT  TGGAGGAATT  C
```

FIG. 7B

```
  1  CTCCCAATAT  TGTCATGAGG  CTTGCATCCC  AGGTTAGTTT  TTTTTCCTTT
 51  CTGAAATTTA  TATTCCATAC  CTTTTCACCT  TTAGTTATCC  TTGTATTTTC
101  TGGAAGCTTC  ATCTGATGCA  TTATTGACAA  ATGCACTAAT  GGTCATCATA
151  TTTGsAkAgw  yAAsATAtkT  mTCTTaattg  aTGGkwACtm  TTgamwATGA
201  srATgsTkrA  GCAkrTrryk  wAyAstTTTT  TaATAAAAAA  AcatGCaTTT
251  cTAgGAGtTG  GAcTaAGctT  TTCTTAGtAT  GAaGtGcCAT  GtTTTAcATg
301  GTCCATTTGt  GTCAATTTAC  AGTCgGTATC  ATGGaAAGGt  TGTCATAATG
351  GcTGGAGAga  AACAACAcAT  CTTGtTTCTC  AACAcTTGTg  GGAGAAGAtG
401  TTTTAcCTTT  TTTcCTAAAA  TTACTTTTTG  TACTAAATTG  TATAAkTTTT
451  cCAATATTCT  cCATGATTAT  TGAACTCTGC  TGTGtTCAAA  CAGCCAAAAC
501  ATGTTTcCAT  ACTTTACACC  TTTATTTTTT  AGATGGAAgC  CTGGAATTGT
551  GCTCTGTTAT  CTGTAgTCAT  GCAtTATAtT  TGATCTTAAA  tCyTAtTCTC
601  TATTGTAGAr  TCsGCAtCTT  GAAgTTCAGT  TGCtTTGTGA  TCAATATGGT
651  AATGTAGCAG  CACTTCACAG  TCGTGATTGC  AGTGTGCAAC  GGCGACACCA
701  GAAGGTCTGC  CCCTCACCCA  CCCAGCCATA  AACACGAAGT  TTATAGAACC
751  ATGTATTTTG  TTATGCAATA  TATTTCTCAA  TTGTAGCTCC  ATTCACATTT
801  TGCTACAACA  GATTATTGAA  GAAGGTCCAG  TTACTGTTGC  TnCCTCGTGA
851  GACAGTTAAA  GCACTTGAGC  AGCAGCAAGG  AG
```

FIG. 7C

| | | | | | |
|---|---|---|---|---|---|
| 1 | GTcGACCTGC | AGGTCAACGG | ATCCTAgGGG | GCCAACAGAT | TcTTATcaaA |
| 51 | TgAATGggat | TATCaATGAA | AcacATaATG | GaAGACAtGC | cTCAGtGTCC |
| 101 | AAgGTTGtTG | aATTTTGTGC | GGCAcTAgGT | GGCaAAACAC | CaATTCACAG |
| 151 | TATATTAGTG | GCCAACAATG | GaATGGCAgC | AGCaAAAtTT | ATGagGaGTG |
| 201 | TCCGGACATG | GGCTAATGAT | AcTTTTGGAT | CTGAGAAgGC | AATTCAACTC |
| 251 | ATAGCTATGG | CAACTCCGGA | AGACATGAGG | aTAAATGCAG | AACACATTAG |
| 301 | AATTGCTGAC | CAATTCGTAg | ArgTGcctgG | TGgaacaaAC | AAtAATAAct |
| 351 | AcgCCAaTGT | TCAAcTcATA | gTGGAgGTTA | GCCTTGcTAA | TCTGTTAgTT |
| 401 | TACTACTGgT | CtGCtGtTTC | CtTTAtTTGt | tGTaTAATGA | ttGACaTATT |
| 451 | taAgTagAgA | AAtTTATAtT | TCtCctCtgC | tGTTGTGgAa | gTCCAatTGT |
| 501 | CaCCAtTAAC | tGTgaAATAt | TGCagATgGc | aCaAAAACtA | gGtGtTTcTg |
| 551 | CTgTTTGGCC | TgGTTGGGGT | CATGCTTCTG | AgAAtCcTGA | ACTGCCAgAT |
| 601 | GCATTGACCG | CAAAAgGGaT | CgTTTTTCTT | GGcCcacCTG | CATCAtCAAT |
| 651 | GaATGCtTTG | GGAGATAAGk | TCgGcTCAgC | TCTCATTGCT | CAAGCAgCCG |
| 701 | GGGtCCCaAC | tCtTGCTTGG | AgTgGATCAC | aTGTGAgTCt | CACtCtTTGA |
| 751 | tTACTAtCCG | cCTGTCtCAt | TGCtCTcTCt | TTCATATTCT | AATGACACTA |
| 801 | AATTTAGGTT | GAAGTTCCAT | TAGAGTGCTG | CTTAGACGCG | ATACCTGAGG |
| 851 | AGATGTATAG | AAAAGCT | | | |

FIG. 7D

| | | | | | |
|---|---|---|---|---|---|
| 1 | GAATAATCTG | CCTGCAGCTC | AAGTTGCTGT | TGGAATGGGC | ATACCTCTTT |
| 51 | GGCAGATTCC | AGGTAATTAC | CAATTTACCA | ACTTATTTAG | TTCCTTATTG |
| 101 | TTTTATTCTC | TAATTTTCTA | CTTATGTAgA | AATCAGAcGT | TtCTATGGAa |
| 151 | TGgAcTATGG | AGGagGGTAt | GAcATTTGGa | GGAAAaCAGC | AGcTCTTGCT |
| 201 | ACACCATTtA | ATTTTGATGA | AgTAgaTTcT | CAATGGCCAA | AGGGCCATTG |
| 251 | TGTAgCAGTT | AGAATTAcTA | GTGAGGACCC | AGATGATGGT | TTCAAACcTA |
| 301 | CTGGTGGGAA | AGTGAAGGTA | AGTTTTCTAG | ATGACATGTA | TTATATATCG |
| 351 | TTCAAAgAgA | TTAAGTTTGG | TTAAATGAcT | AGGTCTTGAT | TTTTTATCTT |
| 401 | TCAGGAGATA | AGTTTTAAAA | GCAAGCCTAA | TGTTTGGGCC | TaCTTCTCAG |
| 451 | TAAAGGTaAC | TTGTTAACTT | TAGTACGCTG | TCACATTATt | ctTCgTTGTG |
| 501 | AAAATAAtTT | GAACGGTtCT | CTTTGTATTT | TaACCAtCCA | tCgTcTCATT |
| 551 | TAgCAgAgCA | CACAAATATT | tGCACTGACC | CCCcTcCCCt | TATCtGctTT |
| 601 | CAgTCTGGTG | GAgGCATtCA | tGAATTtGCT | GATTCTCAGT | TCGGTATGTG |
| 651 | TAAACCAAGA | GTATTCTTTG | TAATTTATAT | TGGTCCTCAA | TTTTGAAATA |
| 701 | TTGTCTTTCC | GTTACAGGAC | AdG | | |

FIG. 7E

```
  1  AATTCCTGTG  GGTGTTATAG  CTGTGGAGAC  ACAGACCATG  ATGCAGCTCA
 51  TCCCTGCTGA  TCCAGGTCAA  CTTGATTCCC  ATGAGCGATG  TGTTCCTCGG
101  GCTGGACAAG  TGTGGTTCCC  AGATNCTGCA  ACCAAGACAG  CTCAGGCATT
151  ATTAGACTTC  AACCGTGAAG  GATTGCCTCT  GTTCATCCTG  GCTAACTGGA
201  GAGGCTtCTC  TGGGGgACAG  AGAGATCTCT  T
```

FIG. 8A

```
  1  AATTCATGCA  TCTTAATAAA  CACAGTTGGC  CCTTAAAGCA  AGTGAACTTC
 51  TTGAACAAAC  CAAACTAAGT  GAACTCTGTT  CCAGCATTGC  AAGAAGCCTT
101  TCAGATCTGG  GGATGCATAA  GGGAGAAATG  ACTATTAAGG  ATAGCATGGA
151  AGATTTAGTC  TCTGNCCCAT  TGCCTGTTGA  AGATGCTCTT  ATTTCTTTGT
201  TTGATTA
```

FIG. 8B

```
  1  ATAGACCTGT  CGCATACATC  CCTGAGAACA  CATGCGATCC  GCGTGCAGCC
 51  ATCCGTGGnG  TAGATGACAG  CCAAGGGAAA  TGGTTGGGTG  GTATGTTTGA
101  CAAAGACAGC  TTTGTGGAGA  CATTTGAAGG  ATGGGCAAAA  ACAGTGGTTA
151  CTGGTAGAGC  AAAGCTTGGA  GGAAGGAATT
```

FIG. 8C

GENE COMBINATIONS FOR HERBICIDE TOLERANCE IN CORN

CROSS-REFERENCE TO RELATED APPLICATIONS

This application is a continuation-in-part of international application No. PCT/US96/04625, filed Apr. 4, 1996 which is a continuation-in-part of U.S. application Ser. No. 08/417,089, filed Apr. 5, 1995 which is a continuation-in-part of U.S. application Ser. No. 08/014,326, filed Feb. 5, 1993 now U.S. Pat. No. 5,498,544 which issued Mar. 12, 1996, the disclosures of which are incorporated by reference herein.

STATEMENT OF GOVERNMENT RIGHTS

The present invention was made with the support of the United States Government via a grant from the United States Department of Agriculture (92-37301-7852). The Government has certain rights in the invention.

BACKGROUND OF THE INVENTION

The use of selective herbicides for controlling specific weeds or plants in crops has become almost a universal practice. The market for these herbicides approaches a billion dollars annually. Even with this extensive use, weed control remains a significant and costly problem for the farmer.

Present day herbicides used singly or in so-called tank mixes require careful management to be effective. Time and method of application and stage of weed plant development are critical to getting good weed control with herbicides. Application of large amounts of preemergence herbicides can result in a commitment to grow the same crop in subsequent years because of chemical persistence in the soil which prevents rotation with a crop sensitive to that herbicide. Furthermore, some weed species are simply resistant to the available herbicides. Therefore, the development of effective herbicides increases in importance every year, especially as other weeds are controlled and thus reduce interplant competition.

Weed control in maize is currently accomplished by soil application of herbicides that are applied before the crop emerges and prior to the observation of a weed problem. The preemergence herbicides currently used adequately control most dicot and monocot (grass) weeds in maize. However, annual grass weeds such as wild proso millet and wooly cupgrass and perennial grass weeds commonly escape preemergence weed control. Preemergence herbicides require rainfall for activation, and under low rainfall conditions they fail to control grass weeds in maize. Furthermore, some preemergence herbicides persist in the soil and several have been detected as groundwater contaminants. The options for controlling these escape grass weeds are very limited.

A postemergence herbicide for grass weed control in maize would be very beneficial. An attractive alternative to developing new herbicides to combat this weed control problem in maize and/or to decrease the amount of herbicide carryover and groundwater contamination in maize fields from the existing herbicides is to develop maize hybrids or varieties that are tolerant to other existing herbicides that normally kill all monocot (grass) species. The herbicide POAST™ (BASF Corp., Parsippany, N.J.), the active ingredient of which is sethoxydim, kills most grasses, and is applied at lower rates than many preemergence herbicides. POAST™ is nonpersistent in the environment and therefore does not represent a groundwater contamination threat. POAST™ tolerant maize would provide the producer with increased weed management flexibility because POAST™ could be applied when a grass weed problem was detected without risk of damage to the crop and only to the areas with a weed problem. Therefore, postemergence control of local weed problems would further decrease the amount of herbicide applied compared to existing preemergence weed control strategies.

The sensitivity of maize to some herbicides is the result of the presence of herbicide sensitive forms of acetyl CoA carboxylase (ACCase) in those plants. ACCase is an enzyme involved in many important metabolic pathways in plant, animal and bacterial cells. Structurally, ACCases are biotinylated and are quite large enzymes consisting of one or more subunits. For example, most ACCases of animals, higher plants, and yeast are dimers of 420 to 700 kD native MW and contain subunits of 200 to 280 kD.

Two forms of ACCase, termed ACCase I and ACCase II, can be isolated from maize. These forms differ in their size, charge, cellular location, immunoreactivity with ACCase I antiserum, and sensitivity to herbicide inhibition. The predominate form, ACCase I, is plastid localized and is sensitive to herbicide inhibition.

Four ACCase genes have been identified in maize by Southern blot analyses (Lutz et al., Maize Genetics Conference (1995)). Restriction fragment length polymorphism (RFLP) analyses mapped one ACCase gene, termed Acc1, to chromosome 2 between umc131 and umc2b (FIG. 1) in recombinant inbred lines from Tx303×C059 (Egli et al., *Maize Genetics Coop. Newsletter*, 68, 92 (1994)). Mutations in the Acc1 gene can result in ACCase that is resistant or tolerant to herbicide inactivation ((Marshall et al., *Theor. Appl. Genet.*, 83,435 (1992); Egli et al., *Plant Physiol.*, 101, 499 (1993); Egli et al., *MNL*, 66, 94 (1992)). However, the R0 plants which were regenerated from tissue cultures selected for resistance (or tolerance) to herbicides, by virtue of mutations in Acc1, exhibit only partial herbicide resistance, i.e., the symptoms induced by herbicide exposure are not prevented (see U.S. Pat. No. 5,162,202).

Caffrey et al. (*Maize Genetics Coop. Newsletter*, 69, 3 (1995)) disclose that RFLP analyses of recombinant inbreds derived from the crosses Tx303×CO159 and T232×CM37 showed that one ACCase gene maps to chromosome 2 between umc131 and uox while another ACCase gene maps to chromosome 10 between ncsu2 and umc155 (FIG. 2). Caffrey et al. further disclose that the ACCase gene on chromosome 10 appears to correspond to an herbicide resistance locus described by Van Dee et al. (*Agro. Abs.*, page 198 (1992)). The authors propose that the ACCase gene on chromosome 10 encodes an herbicide sensitive ACCase that is localized to the plastid while the ACCase gene on chromosome 2 encodes an herbicide resistant ACCase that is non-plastid localized.

Thus, there is a need for a method to prepare a maize plant with resistance or tolerance to herbicides.

SUMMARY OF THE INVENTION

The invention provides a method to prepare maize ("corn" or *Zea mays L.*) plants with resistance or tolerance to cyclohexanedione or aryloxyphenoxypropionate herbicides, i.e., maize plants with high tolerance to field application rates of herbicide. The herbicide resistance or tolerance is the result of the plants having at least one copy of each of two herbicide resistant or tolerant acetyl CoA carboxylase (ACCase) genes, one of which is encoded on chromosome 2 (Acc1) and the other of which is encoded on chromosome 10 (Acc2), i.e., the plant is a double heterozygous mutant (e.g., Acc1-S2/+;+/Acc2-S5). In contrast, when a plant has only one copy of either of the herbicide resistant ACCase genes, e.g., Acc1-S2/+;+/+ or +/+;Acc2-S5/+, the plant exhibits only partial tolerance to the herbicide, i.e., the expression of the herbicide resistant ACCase gene does not prevent symptoms of herbicide damage under standard field-application rates of herbicides.

In commercial corn breeding practices, the double heterozygous genotype can be a hybrid variety planted by farmers. To prepare the double heterozygote, a homozygous double mutant parent line (e.g., Acc1-S2/Acc1-S2;Acc2-S5/Acc2-S5) is crossed to a normal (nonmutant) susceptible parent line. Thus, corn breeders can maintain fewer homozygous double mutant parent lines than would be needed with a system in which both parents must be homozygous for a single mutant gene to obtain a fully herbicide resistant maize plant.

Thus, the invention provides a method of imparting cyclohexanedione or aryloxyphenoxypropanoic acid herbicide tolerance to a corn plant. The method comprises crossing a first corn plant with a second corn plant so as to yield progeny plants. The first plant is homozygous for an allele of Acc1 which imparts cyclohexanedione or aryloxyphenoxypropanoic acid herbicide tolerance. The second plant is homozygous for an allele of Acc2 which imparts cyclohexanedione or aryloxyphenoxypropanoic acid herbicide tolerance. The progeny plant is heterozygous for the Acc1 allele which imparts cyclohexanedione or aryloxyphenoxypropanoic acid herbicide tolerance and heterozygous for the Acc2 allele which imparts cyclohexanedione or aryloxyphenoxypropanoic acid herbicide tolerance. A preferred embodiment of the invention is a method of imparting herbicide tolerance to a hybrid plant.

The invention also provides a method of imparting tolerance to a corn plant to an agent which inhibits acetyl CoA carboxylase, wherein the agent is selected from the group consisting of 3-(2,4-dichlorophenyl)-perhydroindolizine-2,4-dione (Babczinski et al., *Pesti. Sci.*, 33, 455 (1991)), 3-isopropyl-6-(N-[2,2-dimethylpropyl]-acetamido-1,3,5-triazine-2,4-(1H,3H)dione (Walker et al., *Phytochem.*, 29, 3743 (1990)), soraphen A (Vahlenesiock et al., *Curr. Genet.*, 25 93 (1994)), and structural and/or functional analogs thereof. The method comprises crossing a first corn plant, which is homozygous for an allele of Acc1 which imparts tolerance to the agent, with a second corn plant, which is homozygous for an allele of Acc2 which imparts tolerance to the agent, so as to yield progeny plants. The progeny plant is heterozygous for the Acc1 allele which imparts agent tolerance and heterozygous for the Acc2 allele which imparts agent tolerance.

Also provided is a method to prepare an herbicide resistant or tolerant corn plant. The method comprises crossing a first corn plant which comprises at least one herbicide resistant allele with a second corn plant which comprises at least one herbicide resistant allele which is not allelic to the herbicide resistant allele in the first plant, to yield a progeny plant which is a heterozygote for each allele.

The invention further provides a method of imparting cyclohexanedione or aryloxyphenoxypropanoic acid herbicide tolerance to a corn plant. The method comprises self pollinating a corn plant which comprises (i) an allele of Acc1 which imparts cyclohexanedione or aryloxyphenoxypropanoic acid herbicide tolerance and (ii) an allele of Acc2 which imparts cyclohexanedione or aryloxyphenoxypropanoic acid herbicide tolerance, so as to yield a progeny plant. Then a progeny plant is identified that is homozygous for the allele of Acc1 which imparts cyclohexanedione or aryloxyphenoxypropanoic acid herbicide tolerance and is homozygous for the allele of Acc2 which imparts cyclohexanedione or aryloxyphenoxypropanoic acid herbicide tolerance.

Also provided is a method of preparing a plant which is a double heterozygote for alleles of Acc1 and Acc2 which impart cyclohexanedione or aryloxyphenoxypropanoic acid herbicide tolerance. The method comprises crossing a first corn plant with a second corn plant so as to yield progeny plants. The first plant is homozygous for an allele of Acc1 which imparts cyclohexanedione or aryloxyphenoxypropanoic acid herbicide tolerance and the second plant is homozygous for an allele of Acc2 which imparts cyclohexanedione or aryloxyphenoxypropanoic acid herbicide tolerance. The progeny plant is heterozygous for the Acc1 allele which imparts cyclohexanedione or aryloxyphenoxypropanoic acid herbicide tolerance and heterozygous for the Acc2 allele which imparts cyclohexanedione or aryloxyphenoxypropanoic acid herbicide tolerance.

The invention also provides a method of preparing a plant which is a double homozygote for alleles of Acc1 and Acc2 which impart cyclohexanedione or aryloxyphenoxypropanoic acid herbicide tolerance. The method comprises self pollinating a corn plant which comprises (i) an allele of Acc1 which imparts cyclohexanedione or aryloxyphenoxypropanoic acid herbicide tolerance and (ii) an allele of Acc2 which imparts cyclohexanedione or aryloxyphenoxypropanoic acid herbicide tolerance, so as to yield a progeny plant. A progeny plant is identified that is homozygous for the allele of Acc1 which imparts cyclohexanedione or aryloxyphenoxypropanoic acid herbicide tolerance and is homozygous for the allele of Acc2 which imparts cyclohexanedione or aryloxyphenoxypropanoic acid herbicide tolerance.

Also provided are progeny and seed derived from the plants prepared by the methods described herein.

Yet another embodiment of the invention is an inbred or hybrid cyclohexanedione or aryloxyphenoxypropanoic acid herbicide tolerant *Zea mays* plant. The genome of the inbred or hybrid plant of the invention is homozygous for an allele of Acc1 which imparts cyclohexanedione or aryloxyphenoxypropanoic acid herbicide tolerance, and is homozygous for an allele of Acc2 which imparts cyclohexanedione or aryloxyphenoxypropanoic acid herbicide tolerance.

A further embodiment of the invention is an inbred or hybrid cyclohexanedione or aryloxyphenoxypropanoic acid herbicide tolerant *Zea mays* plant, the genome of which is heterozygous for an allele of Acc1 which imparts cyclohexanedione or aryloxyphenoxypropanoic acid herbicide tolerance, and is heterozygous for an allele of Acc2 which imparts cyclohexanedione or aryloxyphenoxypropanoic acid herbicide tolerance.

Progeny and seed derived from the inbred plants of the invention are also provided.

As used herein, the term "cyclohexanedione herbicide" includes, but is not limited to, 1,3-cyclohexanediones which exhibit general and selective herbicidal activity against plants. One such cyclohexanedione is sethoxydim {2-[1-(ethoxyimino)-butyl]-5-[2-(ethylthio)propyl]-3-hydroxy-2-cyclohexen-1-one}. Sethoxydim is commercially available from BASF (Parsippany, N.J.) under the designation POAST™.

Other herbicidal cyclohexanediones falling with in the scope of the invention include clethodim, (E,E)-(±)-2-[1-[[(3-chloro-2-propenyl)oxy]imino]propyl]-5-[2-(ethylthio)

propyl]-3-hydroxy-2-cyclohexen-1-one; available as SELECT™ from Chevron Chemical (Valent) (Fresno, Calif.); cloproxydim, (E,E)-2-[1-[[(3-chloro-2-propenyl)oxy]imino]butyl]-5-[2-(ethylthio)propyl]-3-hydroxy-2-cyclohexen-1-one; available as SELECTONE™ from Chevron Chemical (Valent) (Fresno, Calif.); and tralkoxydim, 2-[1-(ethoxyimino)propyl]-3-hydroxy-5-mesitylcyclohex-2-enone, available as GRASP™ from Dow Chemical USA (Midland, Mich.), as well as other cyclohexanedione herbicides that are structurally related to the compounds described hereinabove.

As used herein, the term "aryloxyphenoxypropanoic acid herbicide" includes aryloxyphenoxypropanoic acids which exhibit general and selective herbicidal activity against plants. Such herbicides include, but are not limited to compounds wherein the aryloxy group may be phenoxy, pyridinyloxy or quinoxalinyl. One such herbicidal aryloxyphenoxypropanoic acid is haloxyfop, {2-[4-[[3-chloro-5-(trifluoromethyl)-2-pyridinyl]oxy]phenoxy]-propanoic acid}, which is available as VERDICT™ from Dow Chemical USA (Midland, Mich.). Another is diclofop, {(±)-2-[4-(2,4-dichlorophenoxy)-phenoxy]propanoic acid}, available as HOELON™ from Hoechst-Roussel Agri-Vet Company (Somerville, N.J.). Other aryloxyphenoxypropanoic acid herbicides within the scope of the invention include fenoxyaprop, (±)-2-[4-[(6-chloro-2-benzoxazolyl)oxy]phenoxy]propanoic acid; available as WHIP™ from Hoechst-Roussel Agri-Vet Company (Somerville, N.J.); fluazifop, (±)-2-[4-[[5-(trifluoromethyl)-2-pyridinyl]oxy]phenoxy]propanoic acid; available as FUSILADE™ from ICI Americas (Wilmington, Del.); fluazifop-P, (R)-2-[4-[[5-(trifluoromethyl)-2-pyridinyl]oxy]phenoxy]propanoic acid; available as FUSILADE 2000™ from ICI Americas (Wilmington, Del.); and quizalofop, (±)-2-[4[(6-chloro-2-quinoxalinyl)-oxy]phenoxy]propanoic acid; available as ASSURE™ from E. I. DuPont de Nemours (Wilmington, Del.), as well as other herbicidal compounds which are structurally related to the compounds described hereinabove.

As used herein, a plant that is "resistant or tolerant to inhibition by a herbicide or agent" is a plant that grows in an amount of herbicide or agent that normally inhibits growth of a corresponding susceptible plant, as determined by methodologies known to the art. For example, a maize plant of the invention (e.g., Acc1-S2/Acc1-S2;Acc2-S5/Acc2-S5 or Acc1-S2/+;Acc2-S5/+) grows in an amount of cyclohexanedione that inhibits the growth of a corresponding susceptible maize plant (e.g., +/+;+/+, Acc1-S2/+;+/+ or +/+;Acc2-S5/+). In the alternative, the herbicide resistance of a homozygous backcross converted inbred plant of the invention (Inbred A (Acc1-S2/Acc1-S2;Acc2-S5/Acc2-S5) is compared to the herbicide resistance of a recurrent inbred susceptible plant (Inbred A (+/+;+/+)). A homozygous backcross converted inbred plant of the invention is a plant which has been repeatedly crossed to the recurrent inbred parent until the backcross converted inbred plant is substantially isogenic with the recurrent inbred parent except at Acc1 and Acc2 loci, and is then self-pollinated (selfed) at least once.

As used herein, "substantially isogenic" means that the genomic DNA content of a homozygous backcross converted inbred plant is at least about 92%, preferably at least about 98%, and most preferably at least about 99%, identical to the genomic DNA content of a recurrent inbred parent of the backcross converted inbred plant.

Exemplary susceptible maize lines, e.g., lines which are sensitive to growth inhibition by cyclohexanedione or aryloxyphenoxypropanoic acid herbicides include, but are not limited to, A188, A641, A619, B73 and *Zea mays*, var. PI 3140. Exemplary maize lines which are a source of either Acc1 or Acc2 herbicide resistance alleles include, but are not limited to, *Zea mays*, var. DK 592$_{SR}$, *Zea mays*, var. DK 404$_{SR}$, 4400$_{SR}$ and 7800$_{SR}$.

BRIEF DESCRIPTION OF THE FIGURES

FIG. 3 depicts the DNA sequence (SEQ ID NO:9) of a 7470 base pair cDNA of a maize ACCase gene.

FIG. 4 depicts the predicted amino acid sequence of a complete ACCase gene of maize (SEQ ID NO:10).

FIG. 5 depicts the partial nucleotide sequence of a Type A$_1$ ACCase genomic clone (SEQ ID NO:11).

FIG. 6 depicts the partial nucleotide sequence of clone 5A, a Type A ACCase genomic clone (SEQ ID NO:12).

FIG. 7 depicts the partial nucleotide sequence of five Type A$_2$ ACCase genomic clones (A–E) (SEQ ID NOs 13, 14, 15, 16 and 17).

FIG. 8 depicts the partial nucleotide sequence of three Type B ACCase clones (A–C) (SEQ ID NOs 18, 19 and 20).

DETAILED DESCRIPTION OF THE INVENTION

Figure 1A:
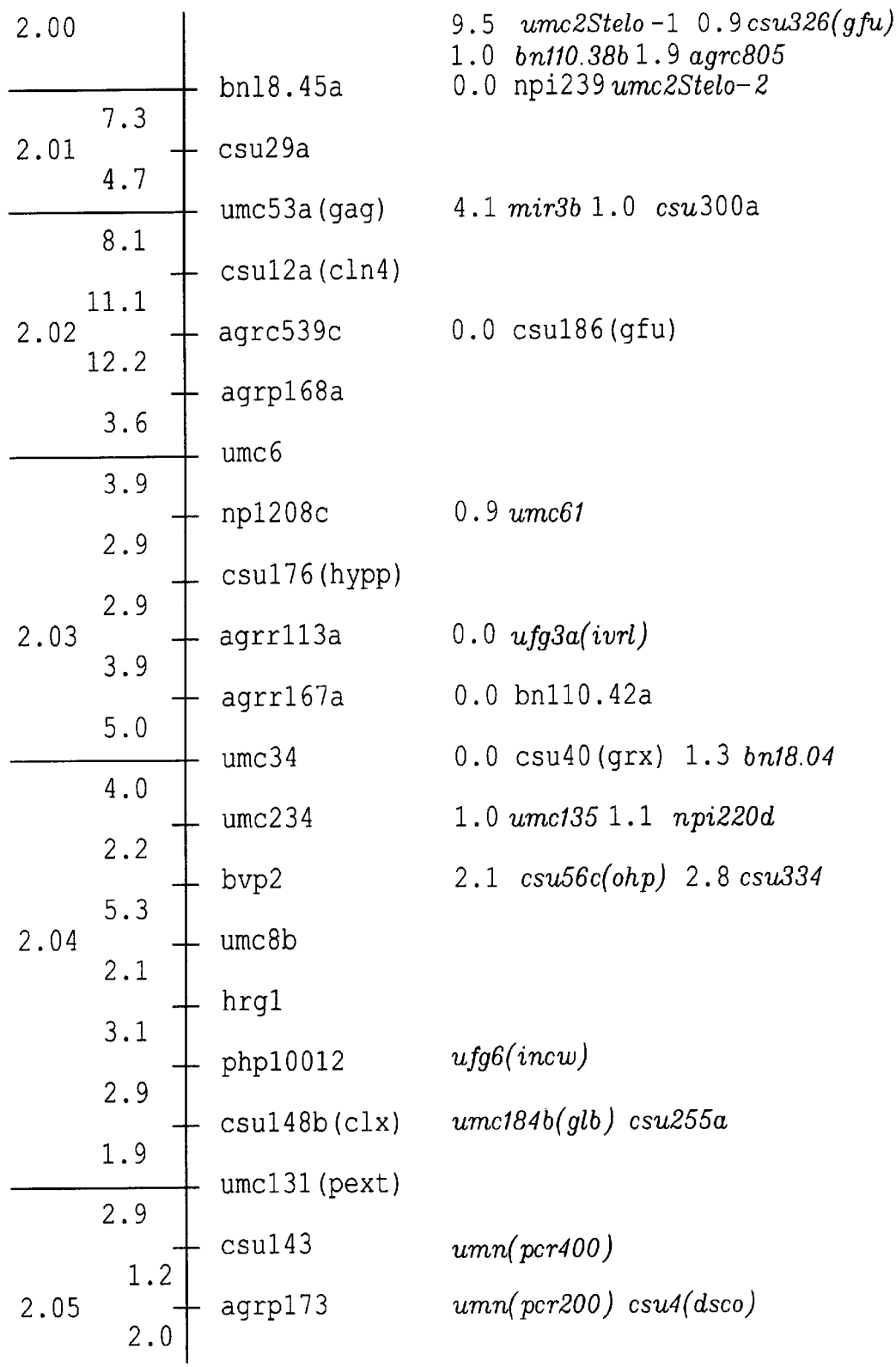
FIG. 1 depicts the genetic map of maize chromosome 2.
Figure 1B:
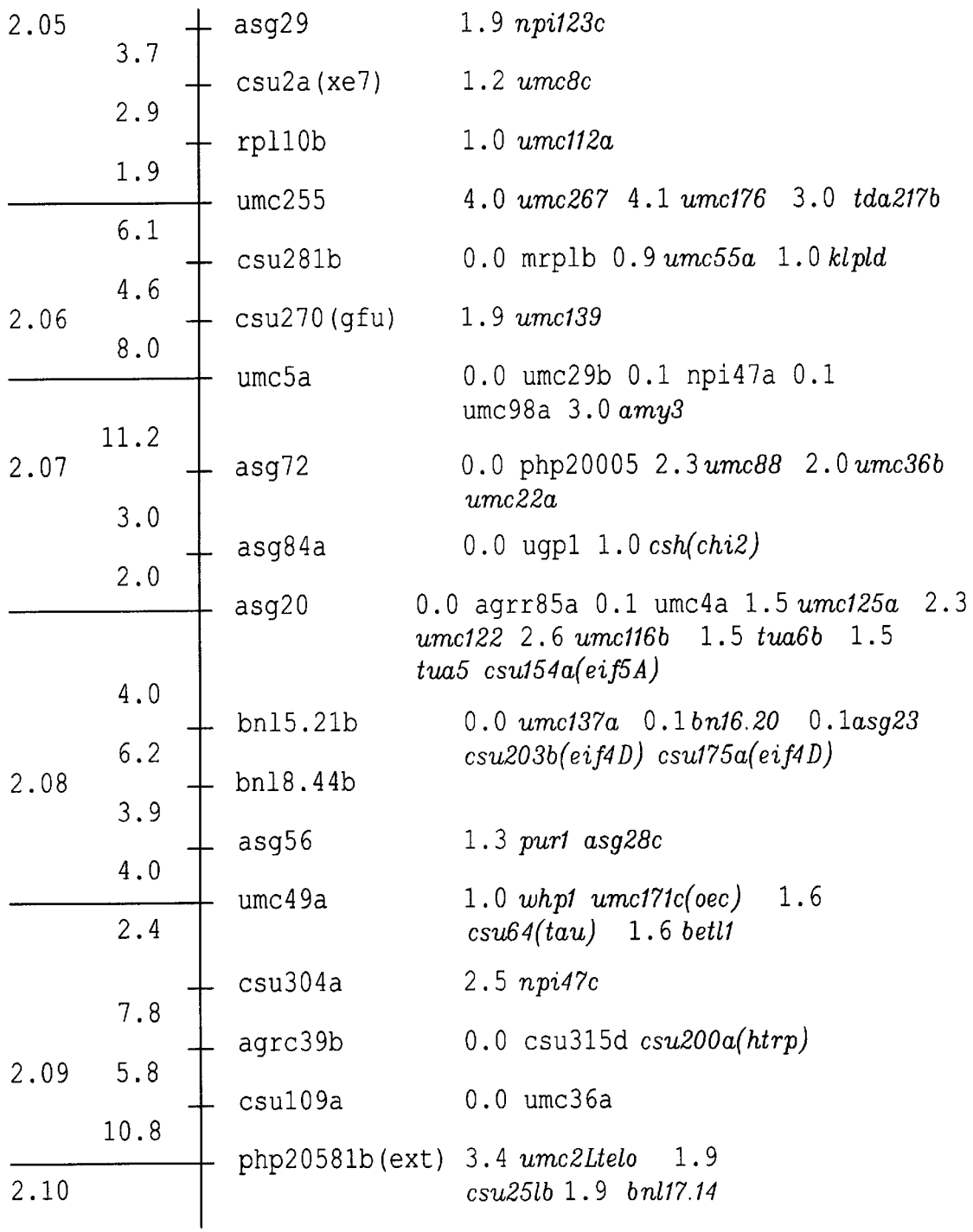
Figure 2A:
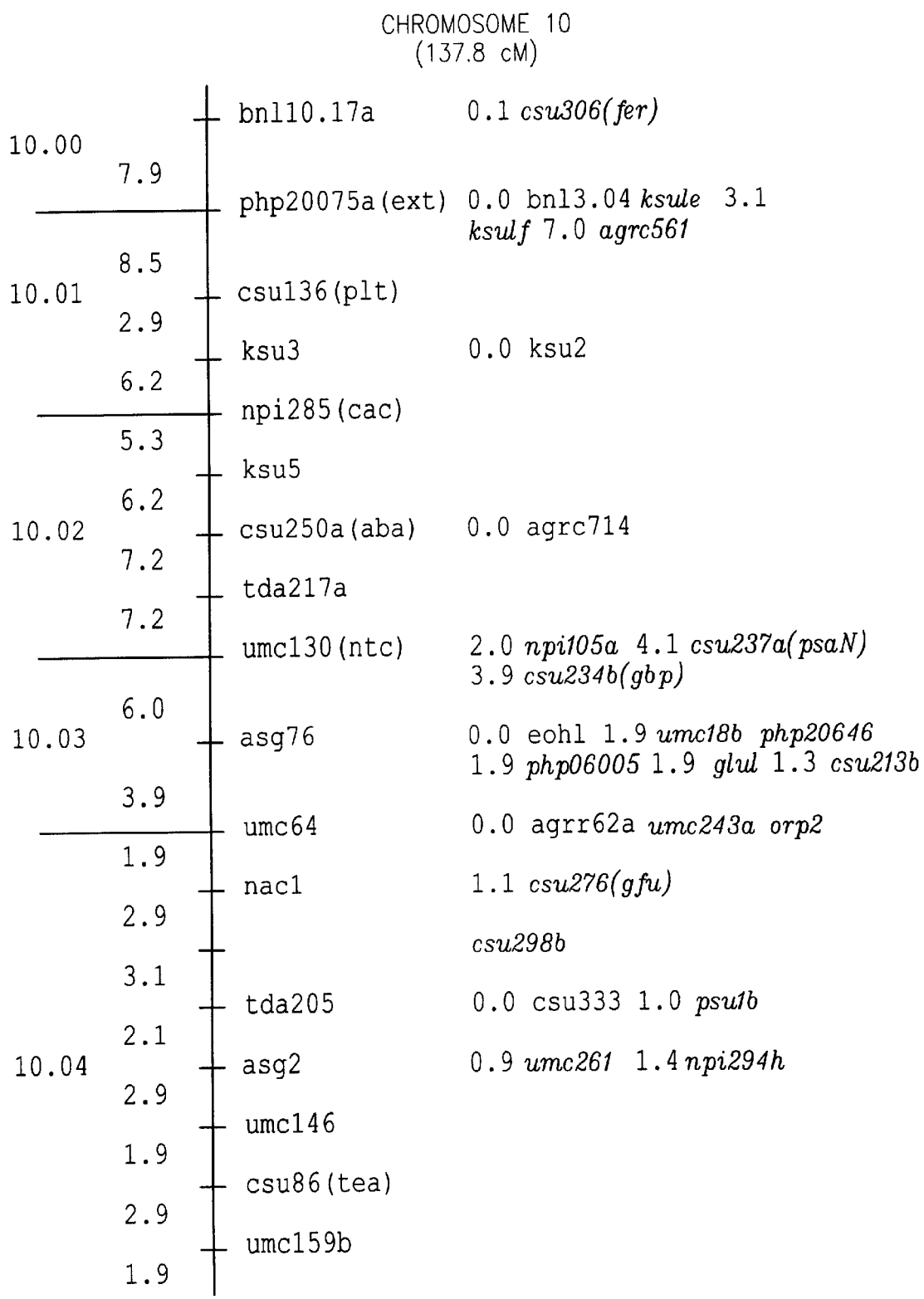
FIG. 2 depicts the genetic map of maize chromosome 10.
Figure 2B:
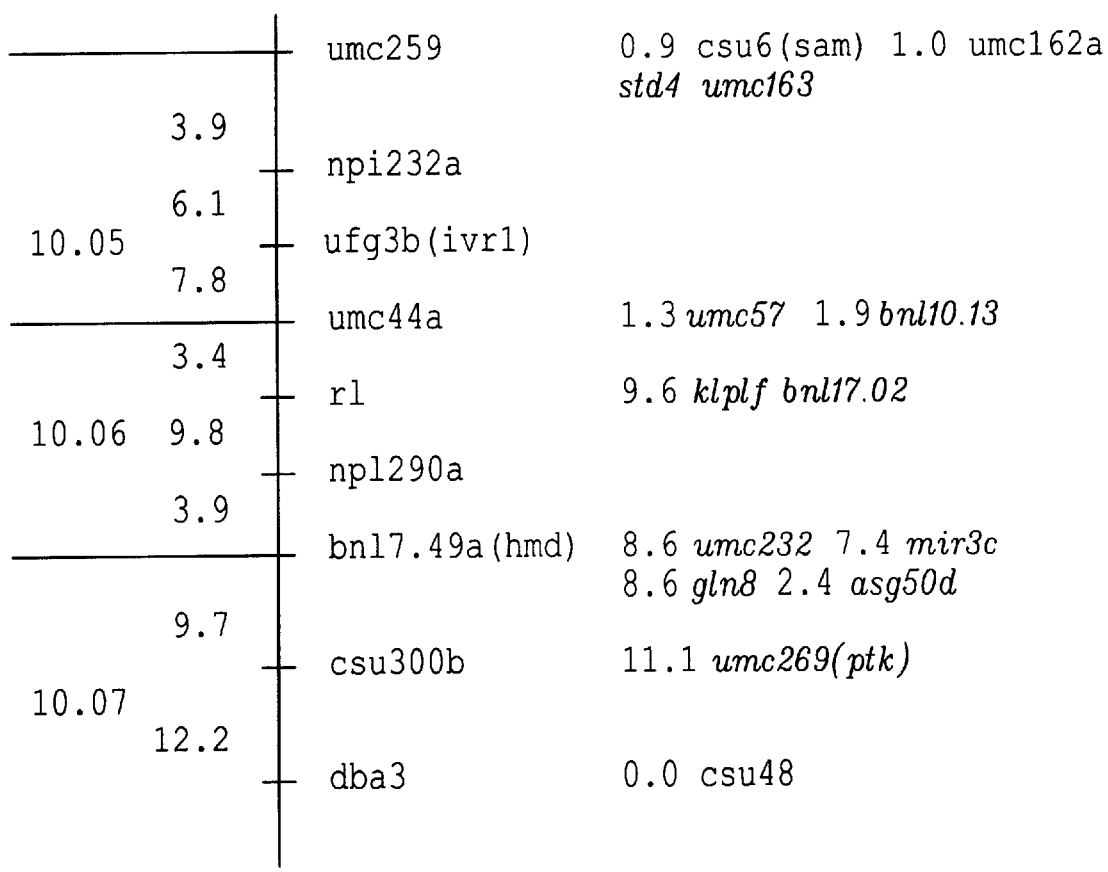

It is envisioned that a variety of corn breeding programs may be employed to introduce an herbicide tolerant gene or allele into a particular genetic background. Field crops are bred through techniques that take advantage of the plant's method of pollination. A plant is self-pollinating if pollen from one flower is transferred to the same or another flower of the same plant. A plant is cross pollinated if the pollen comes from a flower on a different plant.

Plants that have been self pollinated and selected for type for many generations become homozygous at almost all gene loci and produce a uniform populations of true breeding progeny. A cross between two homozygous plants from differing backgrounds or two homozygous lines produce a uniform population of hybrid plants that may be heterozygous for many gene loci. A cross of two plants that are each heterozygous at a number of gene loci will produce a population of hybrid plants that differ genetically and will not be uniform.

Corn plants can be bred by both self-pollination and cross pollination techniques. Corn has male flowers, located on the tassel, and female flowers, located on the ear, on the same plant. Natural pollination occurs in corn when wind blows pollen from the tassels to the silks that protrude from the tops of incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations, the heterozygous condition gives way to homogenous lines as a result of self-pollination and selection. Typically, in the pedigree method of breeding, five or more generations of selfing and selection is practiced.

Backcrossing can be used to improve an inbred line. Backcrossing transfers a specific desirable trait from one inbred or other source to an inbred that lacks that trait (see below).

A hybrid corn variety is the cross of two inbred lines, each of which may have one or more desirable characteristics lacked by the other or which complement the other. The hybrid progeny of the first generation is designated $F_1$. In the development of hybrids, only the $F_1$ hybrid plants are sought. The $F_1$ is more vigorous than its inbred parents.

The development of a hybrid corn variety involves three steps: (1) the selection of superior plants from various germplasm pools; (2) the selfing of the superior plants for several generations to produce a series of inbred lines which, although different from each other, each breed true and are highly uniform; (3) crossing the selected inbred lines with unrelated inbred lines to produce hybrid progeny ($F_1$). During the inbreeding process, the vigor of the lines decreases. Vigor is restored in the $F_1$. Once the best hybrid is identified, the hybrid seed can be reproduced indefinitely as long as the homogeneity of the inbred parent is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again. Because the vigor exhiblited by $F_1$ hybrids is lost in the next generation, seed from hybrid varieties is not used for planting stock.

Hybrid corn seed can be produced by manual detasseling. Alternative strips of two inbred varieties of corn are planted in a field, and the pollen-bearing tassels are removed from one of the inbreds. Providing that there is sufficient isolation from sources of foreign corn pollen, the ears of the detassels inbred (female) will be fertilized only by the other inbred (male), and the resulting seed is therefore hybrid and will form hybrid plants.

The laborious detasseling process can be avoided by using cytoplasmic male sterile (CMS) inbreds. Plants of a CMS inbred are fertilized with pollen from another inbred that is not male sterile. Pollen from the second inbred can contribute genes that make the hybrid plants male fertile. Such breeding methods are well known to the art. See, for example, Hallauer et al., In: *Corn and Corn Improvement*, pp. 463–564 (1988).

Herbicide resistant or tolerant plant variants can be obtained by several methods including, but not limited to, spontaneous variation and direct mutant selection in cultures, direct or indirect mutagenesis procedures on tissue cultures of all cell types, seeds or plants, and mutation of cloned ACCase genes by methods such as site directed mutagenesis. For example, the preparation of herbicide tolerant maize from herbicide tolerant cell lines is described in U.S. Pat. No. 5,162,602, issued Nov. 10, 1992, the disclosure of which is incorporated by reference herein, and in Examples I–III. Briefly, partially differentiated cell cultures are grown and subcultured with continuous exposures to low herbicide levels. Herbicide concentrations are then gradually increased over several subculture intervals. Maize cells or tissues growing in the presence of normally toxic herbicide levels are repeatedly subcultured in the presence of the herbicide and characterized. Stability of the herbicide tolerance trait of the cultured cells may be evaluated by growing the selected cell lines in the absence of herbicides for various periods of time and then analyzing growth after exposing the tissue to normally toxic amounts of herbicide. Mature maize plants are then obtained from maize cell lines that are known to express the trait. Thus, this method is useful to isolate heterozygous dominant, or partially dominant, herbicide resistant mutants.

If possible, the regenerated plants are self-pollinated. Otherwise, pollen obtained from the regenerated plants is crossed to seed-grown plants of agronomically important inbred lines. Conversely, pollen from plants of these inbred lines is used to pollinate regenerated plants. The genetics of the trait are then characterized by evaluating the segregation of the trait in the first and later generation progeny. Stable inheritance of the herbicide tolerance trait is achieved if the plants maintain herbicide tolerance for at least about three to six generations.

Seed from maize plants regenerated from transformed tissue cultures is grown in the field and self-pollinated to generate true breeding plants. Progenies from these plants become true breeding lines which are evaluated for herbicide tolerance in the field under a range of environmental conditions. Herbicide tolerance must be sufficient to protect the monocot plants at the maximum labeled delivery rate under field conditions which cause herbicides to be most active. Appropriate herbicide concentrations and methods of application are those which are known and have been developed for the cyclohexanedione and/or aryloxyphenoxypropanoic acid herbicides disclosed herein.

The commercial value of herbicide resistant corn is greatest if many different hybrid combinations are available for sale. The farmer typically grows more than one kind of hybrid based on such differences as maturity, standability or other agronomic traits. Additionally, hybrids adapted to one part of the corn belt are not adapted to another part because of differences in such traits as maturity, disease, and insect resistance. Because of this, it is necessary to breed herbicide tolerance into a large number of parental lines so that many hybrid combinations can be produced.

To introduce a particular herbicide resistance allele into an inbred background, a conversion process (backcrossing) is carried out by crossing the original herbicide resistant line to normal elite lines and crossing the progeny back to the normal parent. The progeny from this cross will segregate such that some plants carry the gene responsible for tolerance whereas some do not. Plants carrying such genes will be crossed again to the normal parent resulting in progeny which segregate for herbicide resistance and sensitivity once more. This is repeated until the original normal parent has been converted to an herbicide resistant line, yet possesses all other important attributes as originally found in the normal parent. A separate backcrossing program is implemented for every elite line that is to be converted to herbicide resistant line.

Subsequent to the backcrossing, the new resistant lines and the appropriate combinations of lines which make good commercial hybrids are evaluated for herbicide resistance as well as a battery of important agronomic traits. Resistant lines and hybrids are produced which are true to type of the original normal lines and hybrids. This requires evaluation under a range of environmental conditions where the lines or hybrids will generally be grown commercially. Parental lines of hybrids that perform satisfactorily are increased and used for hybrid production using standard hybrid seed corn production practices.

The plants of the invention are expected to be useful for a variety of commercial and research purposes. The plants can be created for use in traditional agriculture to possess traits beneficial to the consumer of the grain harvested from the plant (e.g., improved nutritive content in human food or animal feed). In such uses, the plants are generally grown for the use of their grain in human or animal foods. However, other parts of the plants, including stalks, husks, vegetative parts, and the like, may also have utility, including use as part of animal silage or for ornamental purposes.

The plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The plants may also be used in commercial breeding programs, or may be crossed or bred to plants of related crop species.

The invention will be further described by the following examples.

EXAMPLE I
Identification of Herbicide Mechanism and Site of Action

The objective of this Example was to identify the mechanism whereby sethoxydim and/or haloxyfop inhibit fatty acid synthesis in maize. The results, reported in J. D. Burton et al., *Biochem. Biophys. Res. Comm.*, 148, 1039 (Nov. 13, 1987), show that both sethoxydim and haloxyfop inhibit acetyl-coenzyme A carboxylase (ACCase) (EC 6.4.1.2) in maize chloroplasts.

A. Chemicals

Buffers and cofactors were purchased from Sigma Chemical Company (St. Louis, Mo.); [2-$^{14}$C]acetate was purchased from Research Products International; [2-$^{14}$C]pyruvate and [$^{14}$C]NHCO$_3$ were purchased from New England Nuclear; and [2-$^{14}$C]malonyl coenzyme A was purchased from Amersham. Sethoxydim was a gift from BASF (Parsippany, N.J.), and haloxyfop was provided by Dow Chemical USA (Midland, Mich.).

B. Plant Growth Conditions

Corn (*Z. mays L.*, 'B37×Oh43') seeds were germinated in darkness for 96 hours in vermiculite in an incubation chamber maintained at 30° C., 80% RH. Seedlings were then transferred to a growth chamber with a 16 hour light (25° C.) and an 8 hour dark (20° C.) cycle, 90% relative humidity (RH). After greening 48 hours, seedlings were returned to the dark incubation chamber for 12 hours to deplete chloroplast starch reserves. Seedlings were harvested 6 days after planting. Pea (*P. sativum L.*, 'PI 9901-C') seedlings were grown in vermiculite in a growth chamber with a 16 hour light (21° C.) and 8 hour dark (16° C.) cycle, 80% RH. Peas were harvested 10 to 13 days after planting. Black Mexican Sweet (BMS) corn suspension cultures were maintained in a supplemented Murashige-Skoog (MS) medium (C. E. Green, *Hort. Sci.*, 12, 7–10 (1977)), and subcultured weekly by 20-fold dilution of the suspension culture into fresh medium.

C. Chloroplast Isolation

Chloroplasts from corn and pea seedlings were isolated at 4° C. (K. Cline et al., *J. Biol. Chem.*, 260, 3691–3696 (1985)). Seedlings (50 g of shoots) were homogenized in 200 ml buffer A (50 mM HEPES-NaOH pH 7.5, 330 mM sorbitol, 0.1% w/v BSA, 1 mM MgCl$_2$, 1 mM MnCl$_2$, 2 mM EDTA, 5 mM isoascorbate, 1.3 mM glutathione) in an omnimixer (five, 3-second bursts at full speed). The homogenate was filtered through six layers of cheesecloth and two layers of miracloth, and then centrifuged at 3000 g for 3 minutes with hand-braking. The pellet was gently resuspended in buffer A and layered onto a preformed linear Percoll gradient (50 mM HEPES-NaOH pH 7.5, 330 mM sorbitol, 1.9 mM isoascorbate, 1.08 mM glutathione, 0.1% w/v BSA, 50% Percoll) which was centrifuged at 3000 g for 20 minutes in a Sorvall HB-4 rotor. The lower band in the gradient, containing intact chloroplasts, was washed twice by gently resuspending it in 20 ml of buffer B (50 mM HEPES-NaOH, pH 7.5, and 330 mM sorbitol) followed by repelleting (3000 g, 5 minutes). The final pellet, consisting of intact chloroplasts, was resuspended in 2 to 3 ml of buffer B and stored on ice in the dark until use.

D. Fatty Acid Synthesis

[$^{14}$C]acetate and [$^{14}$C]pyruvate were used as precursors to measure fatty acid biosynthesis in isolated chloroplasts (B. Liedvogel et al., *Planta*, 169, 481–489 (1986)). [$^{14}$C]acetate incorporation was assayed in a 0.5 ml-volume containing: 50 mM HEPES-NaOH (pH 7.5), 330 mM sorbitol, 5 mM KH$_2$PO$_4$, 10 mM NaHCO$_3$, 1 mM MgCl$_2$, 1 mM ATP, 0.1 mM CoA, 0.15 mM [$^{14}$C]acetate (3.33 mCi/mmol), and chloroplasts (20 to 50 µg chlorophyll). [$^{14}$C]pyruvate incorporation into fatty acids was assayed in the same medium except that it included 2 mM TPP, 1 mM NAD$^+$, 0.15 mM [$^{14}$C]-pyruvate (1.33 mCi/mmol), but no acetate. Assay suspensions were illuminated with 1400 µE/m$^2$.second PAR at 25° C. Assays were initiated by the addition of the labelled substrate and stopped by the addition of 0.5 ml of 40% KOH. To determine the incorporation of radiolabel into a non-polar (fatty acid) fraction, each treatment was saponified at 90° C. for 30 minutes in capped vials (P. B. Hoj et al., *Carlsberg Res. Commun.*, 47, 119–141 (1982)). The vials were acidified with 0.5 ml 40% H$_2$SO$_4$, and carrier fatty acids (20 µg each of C 14:0, C 16:0, and C 18:0) were added. The assay mixture was extracted twice with 4 ml hexane. The extracts were combined, dried under N$_2$, and redissolved in 0.3 ml hexane. Aliquots (50 µl) were counted for radioactivity by liquid scintillation spectrometry.

Incorporation of [$^{14}$C]malonyl-Coenzyme A into fatty acids (P. B. Hoj et al., supra; and J. B. Ohlrogge et al., *Proc. Natl. Acad. Sci. USA*, 76, 1194–1198 (1979)) was assayed using cell-free preparations from BMS tissue culture. Cells harvested during logarithmic growth phase were frozen in liquid nitrogen, ground with a mortar and pestle, and thawed in a medium containing: 0.1 M HEPES-KOH, pH 7.5; 0.3 M glycerol, and 5 mM DTT (buffer:tissue, 2:1, v/w). The homogenate was centrifuged at 12,000 g for 20 minutes. The supernatant was filtered through miracloth and centrifuged (125,000 g) for 60 minutes and then filtered through miracloth and assayed. Assays were conducted at 25° C. in a 0.4 ml volume containing: 1.0 mM ATP, 0.32 mM NADPH, 0.38 mM NADH, 25 µM CoA, 10 µM acetyl-CoA, 25 µg acyl-carrier protein, and 12 µM malonyl-CoA (11.54 µCi/µmol). Reactions were initiated by addition of [$^{14}$C]malonyl CoA and stopped by addition of 0.4 ml 40% KOH. Label incorporation into fatty acids was determined as above. Chlorophyll (D. I. Arnon, *Plant Physiol.*, 24, 1–15 (1949)) and protein (P. K. Smith et al., *Anal. Biochem.*, 150, 76–85 (1985)) were determined as described therein.

F. Acetyl-Coenzyme A Carboxylase (ACCase) Activity

Maize chloroplasts, isolated as described above, were suspended in buffer C (0.1 M Tricine-KOH, pH 8.0; 0.3 M glycerol, and 1 mM DTT) and homogenized in a glass tissue homogenizer. The disrupted chloroplast fraction was centrifuged at 16,000 g for 15 minutes. The supernatant was desalted on a Sephadex G-25 column (1.5×5 cm equilibrated with 0.1 M Tricine-KOH, pH 8.0; and 0.3 M glycerol) and assayed directly. ACCase activity (B. J. Nikolau et al., *Arch. Biochem. Biophys.*, 211, 605–612 (1981)) was assayed at 30° C. in a 0.2 ml volume which contained 1 mM ATP, 3 mM acetyl coenzyme A, 2.5 mM $MgCl_2$, 50 mM KCl, 0.5 mM DTT, and 15 mM [$^{14}C$]$NaHCO_3$ (0.17 mCi/mmol). Reactions were initiated by addition of acetyl coenzyme A and stopped by addition of 25 μl of 12 N HCl. Product formation was determined by the radioactivity found in an acid stable fraction by liquid scintillation spectrometry. Enzyme activity was linear for 15 minutes.

G. Results

To probe for the site of herbicidal activity of sethoxydim and haloxyfop, labelled acetate, pyruvate, and malonyl-CoA were used individually as precursors for fatty acid synthesis. Isolated chloroplasts from corn seedlings incorporated [$^{14}C$] acetate and [$^{14}C$]pyruvate into a non-polar fraction (fatty acids). Acetate incorporation was linear for 30 min after a 5 min lag period, and dependent upon the addition of free acetyl coenzyme A. Addition of either 10 μM sethoxydim or 1 μM haloxyfop inhibited [$^{14}C$]acetate incorporation into fatty acids by 90% and 89%, respectively, as shown in Table I, below. Sethoxydim (10 μM) and haloxyfop (1 μM) also inhibited the incorporation of [$^{14}C$]pyruvate into fatty acids by 98% and 99%, respectively.

TABLE I

Inhibition of [$^{14}C$]acetate and [$^{14}C$]pyruvate
Incorporation into Fatty Acids in
Corn Seedling Chloroplasts by
Sethoxydim (10 μM) and Haloxyfop (1 μM),
10 minute assay time

|  | Acetate | Pyruvate |
| --- | --- | --- |
|  | Activity (nmol/mg chl · min) | |
| Control | 4.4 ± 0.4[1] | 10.8 ± 2.3 |
|  | % Inhibition | |
| Sethoxydim | 90 ± 2.5 | 98 ± 1.1 |
| Haloxyfop | 89 ± 3.1 | 99 ± 0.3 |

[1]Results are expressed as mean of two experiments ± standard error.

The effect of 10 μM sethoxydim and 1 μM haloxyfop on [$^{14}C$]malonyl-CoA incorporation into fatty acids was determined using cell-free extracts from corn suspension cultures. Neither sethoxydim (10 μM) nor haloxyfop (1 μM) inhibited fatty acid synthetase activity. Thus, both herbicides inhibited fatty acid synthesis in intact chloroplasts from corn seedlings with either acetate or pyruvate as a precursor, but did not inhibit incorporation of malonyl-CoA into fatty acids. This suggests that ACCase which catalyzes the formation of malonyl-CoA is the site of action of these herbicides.

EXAMPLE II

Selection and Characterization of Herbicide-tolerant Cell Lines

A selection protocol to identify and isolate herbicide-tolerant maize cells was developed to minimize the adverse effects of high herbicide concentrations on somatic embryo development and plant regeneration capacity. The procedure involved exposing tissue to gradually increasing concentrations of herbicide beginning with a sethoxydim concentration representing 1/20th of lethal dose and doubling the herbicide concentration at approximately two-week intervals until the lethal dose (10 μM sethoxydim) was reached. In this way, the herbicide was allowed to take effect slowly with continuous selection pressure, thus permitting herbicide-tolerant cells to accumulate over time while not affecting the potential for plant regeneration.

A. Selection of a Sethoxydim-Tolerant Cell Line

Many selections were carried out utilizing the selection protocol described in the preceding paragraph. The selection of one such sethoxydim-tolerant cell line that was identified and characterized is described below in detail.

Approximately 100 grams of vigorously growing, regenerable, friable, embryogenic maize callus tissue established from an $F_1$ immature embryo resulting from the cross A188×B73 were transferred to agar-solidified maintenance medium (Armstrong and Green, *Planta*, 164, 207 (1985)) in petri plates containing 0.5 μM sethoxydim (BASF) (Parsippany, N.J.). This callus line was designated 2167-9/2160-154. Forty plates were prepared and five clumps of callus tissue weighing about 0.5 grams each were placed on each plate. The 0.5 μM sethoxydim concentration was chosen from growth inhibition studies to provide less than 10–20% growth inhibition during the first two weeks of herbicide exposure. After 14 days, 0.25–0.5 gram pieces of tissue showing vigorous growth rate and retention of embryogenic morphology (i.e., presence of somatic embryos) were subcultured on fresh medium containing 1.0 μM sethoxydim. Eighty plates containing five pieces of tissue per plate were prepared. For each subsequent transfer, all callus tissue showing growth and somatic embryo forming ability was placed on fresh media containing a two-fold increased sethoxydim concentration. Therefore, callus was transferred at two-week intervals to petri plates containing 0.5, 1.0, 2.0, 5.0 and 10.0 μM sethoxydim. During the course of the selection process, the total number of lines decreased as the herbicide-mediated growth inhibition became more intense. Cell lines exhibiting growth on 10 μM sethoxydim were designated as herbicide-tolerant and given an identification number. Two sethoxydim-tolerant lines were recovered that exhibited uninhibited growth at 10 μM sethoxydim. These lines were designated 2167-9/2160-154 S-1 and 2167-9/2160-154 S-2.

B. Characterization of Herbicide-Tolerant Maize Cell Line 2167-9/2160-154 S-2

Tolerant cell line 2167-9/2160-154 S-2 ("S-2") was characterized to evaluate: (1) the magnitude of sethoxydim tolerance; (2) cross-tolerance of haloxyfop; and (3) the biochemical basis for the tolerance. Callus tissue from S-2 that had been maintained on 10 μM sethoxydim was transferred to media containing up to 100 μM sethoxydim. One-half gram of S-2 tissue was plated on a 7 cm filter paper as a lawn overlaying 50 ml agar-solidified culture medium containing 0, 0.5, 1.0, 2.0, 5.0, 10.0, 50.0 and 100 μM sethoxydim, and cultured for two weeks. Control cell line 2167-9/2160-154 was plated similarly on medium containing the same levels of sethoxydim. The control cell line growth after two weeks was inhibited 50% at 1 μM sethoxydim. Growth of S-2 was not inhibited at 100 μM sethoxydim, indicating that S-2 was at least 100-fold more tolerant than the control callus line.

Growth of S-2 was inhibited with 0.65 μM haloxyfop, whereas the control cell line was inhibited 50% with 0.02 μM, indicating approximately a 30-fold increase in tolerance.

C. Acetyl-Coenzyme A Carboxylase (ACCase) Activity of Maize Cell Line S-2

Assays were conducted to determine if ACCase extracted from cell line S-2 was altered with respect to herbicide activity. ACCase activity of control tissue was 50% inhibited either by 1.5 µM sethoxydim, or by 0.25 µM haloxyfop. ACCase activity of S-2 tissue was inhibited 50% either by 70 µM sethoxydim, or by 1.8 µM haloxyfop, indicating at least 40-fold and 7-fold decreases in herbicide sensitivity on concentration basis, respectively.

EXAMPLE III
Plant Regeneration and Production of Herbicide-Tolerant Seed

A. Plant Regeneration Protocol

Sixteen ca. 150 mg clumps of S-2 callus were transferred per 25×100 mm petri plate containing agar-solidified N6 basal salts and 6% sucrose and incubated 7–14 days in low light (20 µE m$^{-2}$ s$^{-1}$). Several plates containing callus on plant regeneration medium were prepared. Callus was transferred to agar-solidified Murashige-Skoog (MS) medium without hormones and incubated in high intensity light (200 µE m-2 s$^{-1}$) for shoot elongation. Developing plants (1–3 cm long) were isolated from the callus surface and transferred to magenta boxes containing agar-solidified MS salts, 2% sucrose with no hormones for two weeks of further growth. When plants reached the 2–3 leaf stage, they were transplanted to peat pots containing potting soil, and were incubated in the growth room until growing stably. Surviving plants were transferred to soil in 4" diameter plastic pots and grown in the greenhouse.

B. Expression of Herbicide Tolerance in Plants Regenerated from S-2 Callus Tissue Groups of eight control (2167-9/2160-154 unselected) and eight S-2 plants were sprayed with either 0.0, 0.01, 0.05, 0.11, 0.22 or 0.44 kg/ha sethoxydim to determine whole plant sethoxydim-tolerance of greenhouse-grown plants. Control plants were killed by 0.05 kg/ha or more sethoxydim. Plants regenerated from the S-2 cell line survived the 0.44 kg/ha sethoxydim treatment, indicating that S-2 plants exhibit at least 20-fold more tolerance of sethoxydim than control. Shoot height of regenerated S-2 plants was only slightly reduced 14 days after treatment with 0.44 kg/ha sethoxydim.

C. Seed Production from S-2 Plants

Plants surviving sethoxydim treatments of up to 0.44 kg/ha were transplanted to the genetics plot on the University of Minnesota campus, St. Paul, Minn. Additional S-2 plants were transplanted to the field that had not been sprayed. Sixty-five 2167-9/2160-154 control plants and ninety-five S-2 plants were grown to maturity in the field. Plants were either self-pollinated or cross-pollinated to inbred maize lines A188, A619, A641, A661, A665, B37, B73, R806, and W153R. Control seed were produced by selfing 2167-9/2160-154 regenerated plants, or by crossing them with the inbreds listed above.

D. Expression of Herbicide Tolerance in Progeny of Regenerated Plants

Seeds obtained by the crossing procedure described above were viable and germinated normally. Seeds from thirty S-2 selfed plants and fifteen 2167-9/2160-154 control plants were planted in 25×50 cm trays of soil (28 seeds from each plant in one tray) and grown in the greenhouse. Seedlings at the 3–4 leaf stage were treated with 0.1, 0.44, and 1.1 kg/ha sethoxydim and evaluated for visual herbicide damage and shoot height. Based on visual rating of herbicide damage two weeks after treatment, selfed progeny of S-2 plants segregated approximately 1:2:1 for healthy, uninjured plants: to plants showing partial injury: to dead plants, respectively, at 0.44 and 1.1 kg/ha sethoxydim treatments. All control progeny of 2167-9/2160-154 control plants were killed by 0.1 kg/ha and greater levels of sethoxydim. These results demonstrate partially dominant expression of sethoxydim tolerance indicating that sethoxydim tolerance in S-2 plants is a heritable trait. Similar tests were conducted on progeny of S-2 plants crossed to the other inbreds. In all cases, these test cross progeny treated with 0.44 kg/ha sethoxydim segregated 1:1 for growing shoots versus dead shoots whether S-2 plants were used as male or female parents. These results confirm that sethoxydim tolerance is controlled by a single partially dominant nuclear gene. In all cases, control plants crossed to the other inbreds were killed and therefore sethoxydim-sensitive.

E. Method for Obtaining Uniform Herbicide-Tolerant Seed

Progeny of S-2 plants surviving sethoxydim treatments of 0.44 and 1.1 kg/ha and showing no herbicide injury were transferred to the greenhouse and grown to maturity. These plants may be selfed and their progeny evaluated for sethoxydim and haloxyfop tolerance to identify pure breeding herbicide-tolerant maize lines.

Progeny of S-2 plants crossed to inbred lines and exhibiting sethoxydim tolerance may be recurrently backcrossed to the same inbreds. Progeny of each cross may be screened for sethoxydim-tolerance, and tolerant plants grown to maturity and again crossed to the recurrent parent. After six or seven cycles of backcrossing, sethoxydim-tolerant plants may be selfed and progeny screened for tolerance to produce homozygous sethoxydim tolerant maize inbreds.

EXAMPLE IV
Selection of Additional Herbicide-Tolerant Maize Cell Lines

One primarily sethoxydim-tolerant maize cell line, 2167-9/2160-154 S-1, and two haloxyfop-tolerant maize cell lines, 2167-9/2160-154 H-1 and 2167-9/2160-154 H-2, were selected and characterized as follows:

A. Selection of Maize Cell Line 2167-9/2160-154 S-1

Maize cell line 2167-9/2160-154 S-1 was selected from maize cell culture using the protocol described in detail above for the selection of Line 2167-9/2160-154 S-2. Approximately 70 plants were regenerated from Line 2167-9/2160-154 S-1, and either self-pollinated or cross-pollinated to the inbred maize lines A188, A619, A641, A661, A665, B37, B73, R806, and W153R.

B. Selection of Maize Cell Line 2167-9/2160-154 H-1

Line 2167-9/2160-154 H-1 was selected from maize cell culture using a similar protocol described in detail above except maize callus tissue was selected using the herbicide haloxyfop. Maize callus tissue was initially plated on 0.01 µM haloxyfop. At two-week intervals, surviving tissue was subcultured onto 0.05, 0.10 and 0.20 µM haloxyfop. Approximately 50 plants were regenerated from Line 2167-9/2160-154 H-1, and were self-pollinated.

C. Selection of Maize Cell Line 2167-9/2160-154 H-2

Line 2167-9/2160-154 H-2 was selected from maize cell culture using a similar protocol described in detail for line 2167-9/2160-154 H-1. No plants have been successfully regenerated from this line.

D. Characterization of Lines 2167-9/2160-154 S-1, H-1 and H-2

The tolerant callus cultures were characterized to determine the magnitude of sethoxydim and haloxyfop tolerance. Callus tissue from these lines was evaluated in experiments as described above in the characterization of line 2167-9/2160-154 S-2. Table II summarizes the results of these studies. Line 2167-9/2160-154 S-1 and Line 2167-9/2160-154 H-2 showed a four-fold increase in haloxyfop tolerance, while Line 2167-9/2160-154 H-1 exhibited approximately a 60-fold increase in haloxyfop tolerance. Neither haloxyfop selected line showed a significant degree of sethoxydim tolerance, while the sethoxydim selected line S-1 exhibited approximately a 100-fold increase in sethoxydim tolerance.

TABLE II

Herbicide Tolerance of Cell Lines S-1, H-1 and H-2

| Cell Line | Herbicide | |
|---|---|---|
| | Haloxyfop | Sethoxydim |
| 2167-9/2160-154 S-1 | 4[1] | 100 |
| 2167-9/2160-154 H-1 | 61 | 0 |
| 2167-9/2160-154 H-2 | 4 | 0 |

[1]The numbers represent the fold increase in herbicide concentration that results in a 50% reduction in growth of the selected cell lines compared to the unselected control cell line 2167-9/2160-154.

E. Herbicide Inhibition of Acetyl Coenzyme A Carboxylase of Maize Cell Lines S-1, H-1 and H-2

Acetyl Coenzyme A Carboxylase (ACCase) was extracted from cell lines S-1, H-1 and H-2 and assayed as described in detail for maize cell line S-2, above. Table III below summarizes the results of these studies. The ACCase from line S-1 was more tolerant of both sethoxydim and haloxyfop, while the ACCase from line H-1 was more tolerant of haloxyfop, but not of sethoxydim. The ACCase from line H-2 showed no difference from the unselected parent line 2167-9/2160-154 in sensitivity to either herbicide.

However, cell line H-2 exhibited approximately a five-fold higher level of ACCase activity as compared to the unselected parent line 2167-9/2160-154. Thus, selection for sethoxydim or haloxyfop tolerance resulted in a less sensitive ACCase in cell line S-1 and H-1, as well as a higher level of ACCase activity in cell line H-2.

TABLE III

Herbicide Inhibition of ACCase of Maize Cell Lines S-1, H-1, H-2

| Cell Line | Herbicide | |
|---|---|---|
| | Haloxyfop | Sethoxydim |
| 2167-9/2160-154 S-1 | 3 | 4 |
| 2167-9/2160-154 H-1 | 7 | 0 |
| 2167-9/2160-154 H-2 | 0 | 0 |

[1]The numbers represent the fold increase in herbicide concentration that inhibits ACCase activity of the selected cell lines by 50% compared to the unselected parent cell line 2167-9/2160-154.

F. Plant Regeneration and Production of Seed

Cell lines derived by the procedures described above which exhibit herbicide tolerance are put through a plant regeneration protocol to obtain mature plants and seed expressing the resistance trait. The plant regeneration protocol allows the development of somatic embryos and the subsequent growth of roots and shoots.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

G. Deposit of Seeds

Seeds from representative S-2 plants (Ex. III (B)) and H-1 plants (Ex. IV(B)) have been deposited with the American Type Culture Collection, 10801 University Boulevard, Manassas, Va. 20110-2209 USA on Oct. 25, 1988 and assigned accession numbers ATCC 40507, and ATCC 40508, respectively.

EXAMPLE V

Allelic Analysis of Herbicide Tolerant Maize Lines

To determine whether the mutations in herbicide tolerant maize plants derived from herbicide tolerant cell lines were allelic, plants derived from the resistant cell lines were crossed. The results, reported in Marshall et al. (*Theor. Appl. Genet.*, 83 435 (1992)), show that of the five mutations tested, all were allelic.

Materials and Methods

Foliar applications of the herbicides were made to greenhouse- or field-grown seedlings at the three- to five-leaf stage. Herbicides were applied in a spray volume of 187 l/ha that includes 2.3 l/ha crop oil concentrate to enhance uptake. Sethoxydim and haloxyfop were applied using commercial formulations (Poast from BASF Corp and Verdict from Dow Elanco, respectively). Visual observations were recorded 14–21 days after herbicide treatments.

For each mutant, two homozygous tolerant $R_4$ families were derived from two different regenerated plants and two heterozygous $F_1$ families were obtained from crosses of $R_3$ homozygous tolerant lines with the susceptible inbreds A188 and A619. Sethoxydim and haloxyfop each were applied at rates ranging from 0.0034 to 7.0 kg/ha. For each genotype a five-rate doubling series was used to determine herbicide lethality. Because of the large differences between wildtype and mutants in herbicide susceptibility, the ranges of herbicide application rates were varied. Two five plant/pot replicates of each family were evaluated for each rate. Herbicide injury symptoms were scored visually 21 days after herbicide treatment. The lethal rate was considered to be the lowest application rate resulting in death of all seedlings in the four replications of each homozygous tolerant genotype or in the eight replications of the heterozygous combinations.

All $F_1$ combinations (no reciprocals) between S1, S2, S3, H1 and H2 homozygotes were made, and these $F_1$s were test crossed to susceptible inbred lines. The testcross progeny were grown in the greenhouse and treated with the herbicides. In Experiment 1, progeny from testcrosses with each of the ten $F_1$ combinations were treated with 0.05 kg/ha sethoxydim for combinations involving only S lines or with 0.009 kg/ha haloxyfop for combinations involving either of the H lines. In Experiment 2, a selected subset of the $F_1$ combinations was tested that used testcross families that were separately derived from those used in Experiment 1. Testcross progeny of S lines were treated with 0.03 kg/ha sethoxydim, and H1 and H2 progeny were treated with 0.009 kg/ha haloxyfop. In each experiment, known susceptible and heterozygous plants were included as controls.

For each mutant, homozygous tolerant and homozygous susceptible families derived from $R_0$ (heterozygous) plants were classified by evaluating plant responses to the herbicides. Enzyme extracts from these families were assayed for ACCase activity (% of no herbicide control) at herbicide concentrations near or greater than the susceptible wildtype $I_{50}$ value. Activities in tolerant and susceptible extracts included in the same experiments were compared. ACCase activity was considered tolerant if when assayed in the presence of herbicide, it was at least 20% greater than the inhibited wildtype ACCase activity. For each of the mutant lines, tolerant lines tracing back to at least two different $R_0$ plants were evaluated.

Results

Homozygous seedlings of S2 and S3 exhibited only slightly bleached leaves and a slight reduction in plant height, but were not killed at 7 kg/ha sethoxydim, which is at least a 127-fold increase over the lethal rate for wildtype plants (Table IV). S2 and S3 lines also exhibited cross tolerance to haloxyfop. Homozygous S1 seedlings exhibited herbicide tolerance similar to that of S2 and S3. Heterozygotes derived from crosses of the S lines with the wildtype exhibited a tolerance to both herbicides that was intermediate between wildtype and homozygous tolerant seedlings.

In contrast to the S lines, a second distinctive phenotype was represented by H1 homozygous seedlings that exhibited little or no sethoxydim tolerance but significant haloxyfop tolerance. Heterozygotes with the H1 lines exhibited haloxyfop tolerance that was similar to that of the homozygous H1 seedlings. H2 seedlings represented the third phenotype, which exhibited about 16-fold increases in tolerance to sethoxydim and haloxyfop compared to the wildtype. The H2 heterozygotes exhibited a tolerance to both herbicides that was intermediate between wildtype and homozygous tolerant seedlings.

TABLE IV

| Genotype | Lethal rates (kg/ha) | |
| --- | --- | --- |
| | Sethoxydim | Haloxyfop |
| Wildtype[a] | 0.055 | 0.014 |
| Homozygous tolerant[b] | | |
| S2 | >7.0 | 0.22 |
| S3 | >7.0 | 0.22 |
| H1 | 0.055 | 0.11 |
| H2 | 0.88 | 0.22 |
| Heterozygous tolerant[c] | | |
| Inbred × S2 | ≧1.8 | 0.11 |
| Inbred × S3 | ≧1.8 | 0.11 |
| Inbred × H1 | 0.055 | 0.11 |
| Inbred × H2 | 0.22 | 0.11 |

[a]Average response of A188 and A619
[b]Average response of two families per mutant line
[c]Average response of A188- and A619-derived $F_1$ families The two families of each mutant, derived from different $R_0$ plants and representing independent derivations from the parental A188×B73 cross, had similar responses to the herbicides. Herbicide lethality of heterozygotes of each mutant from the A188 cross was similar to that of the A619 cross. This suggested that background effects did not play a large role in modifying herbicide tolerance.

To determine allelic relationships among the mutations, $F_1$s made between the different homozygous mutants were crossed to herbicide-susceptible inbreds. The testcross progeny were treated with rates of herbicides intended to kill wildtype plants but allow heterozygous plants to survive. If the mutant alleles from the different mutant lines were at the same locus, then all testcross progeny would have had one or the other mutant allele contributed by the $F_1$ parent and would have been tolerant to the herbicide rates used. No susceptible plants were found in a total of 260 testcross progeny from crosses among S1, S2 and S3. Interpretation of these results was straightforward because all S line heterozygous plants included as controls in these tests survived the herbicide treatments as expected, and all inbred wildtype plants died when treated with sethoxydim. Additionally, no haloxyfop-susceptible plants were found in a total of 190 testcross progeny from H1 combinations with S1, S2 or S3, indicating that the H1 mutation is allelic to S1, S2 and S3 mutations.

Testcrosses involving H1 and H2 alleles were more difficult to interpret. The heterozygous controls for H1 and H2 were injured, and some were killed with the haloxyfop rate (0.009 kg/ha) that killed most, but not all, wildtype control plants. Four susceptible plants were found in a total of 310 testcross progeny from combinations of H2 and the S lines. This frequency was clearly different from the 77 susceptible progeny expected if the H2 allele was at an independent locus. It seems most likely that these deaths occurred due to variability in response of the H2 heterozygous plants, but the possibility that the haloxyfop-susceptible plants represented recombination between two closely linked loci cannot be ruled out.

The 5 haloxyfop-susceptible plants among 102 testcross progeny from the H1 and H2 combination also represented a clear difference from the 25 susceptible expected for independent loci, and again may be explained by a variable response of H2 or H1 heterozygous plants. In the testcrosses involving H2, all of the plants that died were from crosses to the inbred A188. A188 was slightly more susceptible than other inbreds, which may have resulted in a slightly lower tolerance in heterozygotes derived from A188. The cause of rare deaths cannot be conclusively interpreted. However, the most likely interpretation is that the S1, S2, S3 and H1 mutations are allelic and that H2 either is allelic or linked (≦4.4 map units, if all 9 plants that died were due to recombination).

Summary

Herbicide tolerance for five maize (Zea mays L.) mutants regenerated from tissue cultures selected for tolerance to the ACCase-inhibiting herbicides, sethoxydim and haloxyfop was determined. Herbicide tolerance in each mutant was inherited as a partially dominant, nuclear mutation. Allelism tests indicated that the five mutations were allelic. Three distinguishable herbicide tolerance phenotypes were differentiated among the five mutants. Seedling tolerance to herbicide treatments cosegregated with reduced inhibition of seedling leaf ACCase activity by sethoxydim and haloxyfop demonstrating that alterations of ACCase conferred herbicide tolerance. Five putative new alleles of the maize ACCase structural gene (Acc1) were identified based on their differential response to sethoxydim and haloxyfop. The group represented by Acc1-S1, Acc1-S2 and Acc1-S3 alleles, which had similar phenotypes, exhibited tolerance to high rates of sethoxydim and haloxyfop. The Acc1-H1 allele lacked sethoxydim tolerance but was tolerant to haloxyfop, whereas the Acc1-H2 allele had intermediate tolerance to sethoxydim but was tolerant to haloxyfop. Differences in tolerance to the two herbicides among mutants homozygous for different Acc1 alleles suggested that sites on ACCase that interact with the different herbicides do not completely overlap.

EXAMPLE VI

Identification and Cloning of Maize cDNA and Genomic Clones Encoding ACCase

Maize cDNA clones encoding a portion of the ACCase gene were identified by screening a DNA library generated from maize. The cDNA clones were used to identify the sequence of the ACCase gene and to identify the genomic DNA fragments encoding the gene or genes for ACCase.

A λ gt11 cDNA library from maize inbred A188 seedlings was prepared by standard method for oligo-dT priming, as described for pea cDNA. (Gantt and Key, Eur. J. Biochem., 166:119–125 (1987). Plaque lifts of the maize cDNA library were screened with maize ACCase antiserum (Egli et al., Plant Physiol., 101, 499 (1993)) to identify plaques expressing ACCase-like proteins, as described by Sambrook et al., cited supra. (1989). The initial screen of 800,000 plaques yielded 120 positives. Rescreening and plaque purification reduced the number of positives to 14. All 14 clones bound ACCase antibodies that, when eluted from plaque lifts (J. Hammarback et al., J. Biol. Chem., 265:12763 (1990)), recognized a 227-kD biotinylated polypeptide on SDS-PAGE western blots of embryo and leaf crude extracts. The strongest western blot reaction was obtained with cDNA clone #15-14. The six best clones were digested with EcoRI to excise maize cDNA inserts. Total insert sizes ranged from 1.2 to 5.1 kb indicating the clones most likely did not contain the full coding sequences for the mature 219-kD and 227-kD ACCase polypeptides (minimum estimates of 6.1 and 6.3 kb, respectively).

Clone #15-14 contained three EcoRI fragments of 2.0, 1.2 and 0.23 kb Southern blots showed that the 1.2 and 2.0-kb fragments of clone #15-14 each hybridized to different fragments in the other five clones, with the exception of clone #4-4 which only contained a 1.2-kb fragment. The six maize cDNA clones contained EcoRI fragments that hybridized to a large transcript (ca. 8.3 kb) on Northern blots of total RNA from maize leaves, embryos and endosperm. BMS cell culture RNA also contained a 7.8 kb transcript. The relative abundance of the 7.8-kb transcript in embryos was higher than the other sources which is consistent with their ACCase activity.

The three EcoRI fragments were subcloned from cDNA clone #15-14 into BlueScript vector and sequenced by the dideoxy chain termination method (Sequenase 2.0 USB) initially using T3 and T7 primers and then oligonucleotide primers based on insert sequence. A clone #16-6 was also sequenced in a similar manner. Clone #16-6 included three EcoRI fragments of 3.1 kb, 1.2 kb, and 0.23 kb and had additional sequence located upstream from that of clone #15-14. After comparing the sequence and determining that the sequence was the same, the additional 1.2 kb sequence at the 5' end was sequenced.

Clone #18-5 was sequenced in a similar manner. Clone #18-5 included 3.9 kb, 1.2 kb, and 0.23 kb EcoRI fragments and contains an additional 1.9 kb 5' sequence upstream from clone #15-14. Subclone #18-5I (3.9 kb EcoRI fragment) has been deposited with the American Type Culture Collection and given Accession No. 69236.

GenBank, PIR-29, and Swiss-Prot 19 data banks have been searched for amino acid homology with the corresponding amino acid sequences of the three subclones of clone #18-5. Peptide sequences corresponding to the maize cDNA subclones had higher similarity to chicken, rat, yeast and other plant and animal ACCases than to any other peptide sequence in the data banks. A comparison of the relative organization of the 3.9, 1.2 and 0.23-kb EcoRI fragments of clone #18-5, their co-linearity and extent of amino acid identity with chicken ACCase cDNA sequence shows that the maize clone #18-5 has a large region near the 3' end with high amino acid identity (40 to 61%) to chicken ACCase, a longer region with 23% identity in the middle of the 3.9-kb sequence, and a short region with 52% identify near the 5' of the 3.9 kb sequence.

Portions of the sequence of the #18-5I subclone have been identified as encoding domains of the ACCase enzyme of functional significance. Those functional regions include a fragment that spans the presumed transcarboxylase active site in the enzyme having the following presumed sequence SEQ ID NO: 1:

This functional domain is contained in the sequence 1112 to 856 base pair from the 3' stop codon or carboxy terminus region of the ACCase coding sequence of maize. This transcarboxylase active sequence is also present in clone #15-14.

Another functional region that has been identified spans the 12 base pair sequence encoding the biotin binding site having the following peptide sequence SEQ ID NO: 2:

```
5'        GTT ATG AAG ATG           3'
          Val Met Lys Met
```

The biotin binding site is encoded approximately 30% in from the 5' (N-terminus) end of rat, chicken and yeast ACCase genes. These functional domains are useful in mapping and fisher identifying other cDNA and/or genomic fragments encoding ACCase genes.

The cDNA clones encoding portions of the acetyl CoA carboxylase genes are useful to identify the sequence of the gene or genes and are useful as probes to locate the genomic copies of the gene or genes. Because the ACCase antibodies used to screen the λ gt11 library recognize both the 219 and 227 kD ACCase polypeptides, it has not been determined which polypeptide is encoded by these less than full length clones. It is likely that the majority of the clones encode the 227 kD polypeptide since that polypeptide is more abundant in the leaf tissue source of the DNA library and the antibodies have a higher affinity for the 227 kD ACCase polypeptide.

The maize genome was analyzed to identify copy number and location of the genomic copies of ACCase gene or genes. Four distinct types of maize ACCase genomic clones have been identified, termed A1, A2, B1 and B2 (see below).

To obtain genomic copies of ACCase genes, a maize B73 genomic library (Clontech, Palo Alto, Calif.) was screened with the 2 kb subclone from #15-14 and several clones of about 15 kb were identified as having homology to the ACCase cDNA. Restriction mapping and partial sequence analysis revealed two types of genomic clones (Type A and Type B) that differed in restriction sites and in their position relative to the ACCase partial cDNA sequence.

The 2.5 kb EcoRI-SalI fragment (#16) from the Type A genomic clone and the 3.0 kb EcoRI-EcoRI fragment (#34) from the Type B genomic clone were shown to hybridize to the 3.9 kb probe from #18-5 and were subcloned into the Bluescript vector and sequenced. Approximately 1.5 kb of DNA sequence from the genomic Type A 2.5 kb fragment were 100% identical to coding sequence from the 3.9 kb cDNA subclone #18-5I described hereinabove; the remaining sequence exhibited no identity with the cDNA clone and presumably represents a noncoding intron sequence. A 350 nucleotide sequence derived from the genomic Type B 3.0 kb fragment was about 95% identical to the cDNA clone

```
1112-856

GTT CCT GCA AAC ATT GGT GGA CCT CTT CCT ATT ACC AAA CCT CTG GAC

CCT CCA GAC AGA CCT GTT GCT TAC ATC CCT GAG AAC ACA TGC GAT CCA

CGT GCA GCT ATC TGT GGT GTA GAT GAC AGC CAA GGG AAA TGG TTG GGT

GGT ATG TTT GAC AAA GAC AGC TTT GTG GAG ACA TTT GAA GGA TGG GCA

AAA ACA GTG GTT ACT GGC AGA GCA AAG CTT GGA GGA ATT CCT GTG GGC

GTC ATA GCT GTG GAG ACA
``` indicating that its coding sequence differs from that of genomic Type A. These results also indicate that the maize genome encodes at least two different genes encoding a polypeptide having acetyl CoA carboxylase activity.

To identify and clone the remainder of the gene representing the amino-terminus of maize ACCase, additional regions from the Type A genomic clone have been subcloned and sequenced. To synthesize the remaining coding region between the end of the cDNA clone #18-5 and the start of transcription, two oligonucleotide primers were synthesized. Primer 1 is complementary to the DNA sequence: (SEQ ID NO:3)

5' GCCAGATTCC ACCAAAGCAT ATATCC 3' near the 5' end of cDNA subclone #18-5I and was be used as a primer for synthesis of cDNA molecules from maize seedling, leaf or embryo RNA. Several independent clones were sequenced and their sequences compared to the known sequence of the Type A genomic clone to determine the exact coding sequence corresponding to that maize gene for ACCase. A similar strategy can be used to obtain the complete coding sequence for genomic Type B ACCase.

The remaining cDNA sequence was obtained by three successive rounds of RT-PCR using oligonucleotide primers based on genomic apparent exon (5') and known cDNA (3') sequences. The primers used to amplify nucleotides 1–240 of the cDNA were 28sst-a5+ (SEQ ID NO:4) and 28sst-6at3+ (SEQ ID NO:5), nucleotides 217–610 of the cDNA were 28sst-5+ (SEQ ID NO:6) and 28-2t3+ (SEQ ID NO:7), and nucleotides 537–2094 of the cDNA were ACCPCR5' (SEQ ID NO:8) and I55$^-$ (SEQ ID NO:3) (Table V). PCR products corresponding to nucleotides 1–240, 217–610, and 537–2094 of the final sequence were cloned into PCR-script (Stratagene).

analysis of this region suggested that the in frame stop codon was also present in the cDNA. The 3' end of the coding sequence was defined by two stop codons present in the large open reading frame after nucleotide 7011. The translated coding sequence predicted a polypeptide of 2325 amino acids (257 kD; SEQ ID NO:10) which was 79 to 81% identical to the multifunctional (MF) ACCases from alfalfa (Shorrosh et al., Proc. Nat'l. Acad. Sci., 91, 4323 (1994)) and wheat (Gornicki et al., Proc. Nat'l Acad. Sci., 91, 6860 (1994)), and to a 118-amino acid predicted polypeptide of a rice expressed sequence tag (Genbank accession #D39099, T. Sasaki), but only 53 to 55% identical to ACCase from other eukaryotes.

In a pileup alignment of plant ACCases (Genetics Computer Group, Madison, Wis.), Met 1 of both maize and *Brassica napus* ACCases was located about 130 amino acids upstream of the conserved sequence VDEFCKALGG, compared to only 25 amino acids upstream for other plant ACCases. The predicted 2325 amino acids of maize ACCase contains a biotinylation site at position 806, within the conserved VMKM motif (Ton et al., Eur. J. Biochem., 215, 687 (1993)). The arrangement and amino acid sequence of binding sites (Shorrosh et al., Proc. Nat'l. Acad. Sci., 91, 4323 (1994)) for ATP (amino acids 318–333), biotin (amino acids 799–811; biotin at 806), acetyl-CoA (amino acids 1952–1961), and carboxybiotin (amino acids 1662–1711) were highly conserved among all MF ACCases.

EXAMPLE VII
Characterization of Maize ACCase Genomic Clones

The initial restriction fragment length polymorphism (RFLP) analysis of EcoRI-digested total DNA from three maize inbred lines showed one band when probed with the 2 kb subclone from #15-14 (internal to gene) and two bands when probed with the 1.2 kb subclone (near the 3' end of the gene). Fragments homologous to the 2 kb probe were

TABLE V

| cDNA Position | 5' primer designation | 5' primer sequence | 3' primer designation | 3' primer sequence |
|---|---|---|---|---|
| nt-1-240 | 28sst-a5+ | GGTCTTCAATTGTGCTGTCTGG (SEQ ID NO:4) | 28sst-6at3+ | CCTTGACGAACAGACTGGCTGTGC (SEQ ID NO:5) |
| nt 217-610 | 28sst-5+ | CACAGCCAGTCTGTTCGTCAAGG (SEQ ID NO:6) | 28-2t3+ | CCTCTACGTAATTGGTCAGC (SEQ ID NO:7) |
| nt 537-2094 | ACCPCR5' | CATAGCTATGGCAACTCCGG (SEQ ID NO:8) | I55 | GGATATATGCTTTGGTGGAATCTGGC (SEQ ID NO:3) |

The original 5.4-kb cDNA clone #18-5 and PCR products from at least three individual PCR per oligonucleotide pair were sequenced in both directions by the dideoxy chain-termination method, using either Sequenase II (U.S. Biochemicals) or ABI 373 (Applied Biosystems, Inc.) protocols. No sequence differences were found in regions of clone overlaps. The complete sequence of the cDNA of maize ACCase (nucleotides 1–7470; SEQ ID NO:9) and its corresponding amino acid sequence (amino acids 1–2325; SEQ ID NO:10) are shown in FIGS. 3 and 4. The 7470 bp cDNA includes a 459 nucleotide 3' untranslated region and 36 nucleotides of 5' untranslated sequences.

The first Met codon in the cDNA (nucleotides 37–39) was identified as the start codon based on its similarity to consensus initiation sequences (Kozak, J. Cell. Biol., 108, 229 (1989); Lutcke et al., Embo. J., 6, 43 (1987)). An in-frame stop was found in the genomic sequence 6 nucleotides upstream of the sequenced cDNA, and RT-PCR monomorphic and the more intense of the two bands hybridizing with the 1.2 kb probe was dimorphic. As discussed above, these results support the view that maize contains at least two distinguishable ACCase genes and that they may be quite similar for much of the coding region. Additional genomic Southern blots of a set of recombinant inbred lines were used to map polymorphisms for the ACCase probes to maize chromosomes. One polymorphism was mapped to the short arm of chromosome 2; other polymorphisms were not evident in these initial tests to identify a chromosomal location for other maize ACCase genes.

The isolation and restriction mapping of additional genomic clones from a B73 genomic library (Clontech) resulted in the identification of four different types of clones termed A1, A2, B1 and B2 which had 96% nucleotide sequence identity. Types A and B correspond to previously published pA3 and pA4 cDNAs (Ashton et al., Plant Mol. Biol., 24, 35 (1994)) and differ from pA3 and pA4 by ~4% in their coding sequences.

Type A and B genomic clones have linear sequence homology except for an insertion in an intron of the Type B genes about 1400 bp 3' of the A1(SEQ ID NO:9) translation start site. Analysis of the insert boundaries revealed a 3-bp target site duplication and a 6-bp direct repeat, and further sequence analysis showed the presence of two new and unique LINE elements (Long Interspersed Nuclear Elements) in B1 and B2. Mammalian LINE elements are highly abundant ($10^4$ to $10^5$ copies), 6 to 7 kb long, and have frequent 5'-end deletions and an A-rich 3' terminus. They are flanked by short direct repeats, and contain two ORFs, one encoding a reverse transcriptase. Three LINE elements (Cin4, 50–100 copies in maize; del2, 250,000 copies in lily; BNR1, 2–5% of genome in sugarbeet) have been described in plants (Leeton et al., *Mol. Gen. Geneti.*, 237, 97 (1993); Schmidt et al., *Chromo. Res.*, 3, 335 (1995); Schwarz-Sommer et al., *EMBO J.*, 6, 3873 (1987)). Maize ACCase B1 has one unique LINE element and B2 has two. The two B2 LINE elements were characterized by differences in their reverse transcriptase sequence. The B genomic clone inserts have characteristic LINE features including cysteine motifs and a possible polyA tail, and high abundance. The LINE insert also has been found in an intron of the maize Shrunken-2 gene (Hannah et al., *Plant Physiol.*, 98, 1214 (1992)).

The nucleotide sequence (3544 nucleotides) of a Type A1 ACCase genomic clone is shown in FIG. 5 (SEQ ID NO:11).

The nucleotide sequence of another Type A clone is shown in FIG. 6 (SEQ ID NO: 12). The sequence is all 5' untranslated sequence and contains two non-identical 7 nucleotide inserts, a CTP (i.e., it can be amplified with primers 28sst-97F and 28sst-6t3+) and at least the first ⅓ of an ACCase coding sequence. The CTP of SEQ ID NO. 12 is identical to the CTP of A1 clones.

The partial nucleotide sequence of five Type A2 clones is shown in FIG. 7 (SEQ ID NOs 13, 14, 15, 16 and 17 respectively).

A limited sequence comparison of SEQ ID NO:12 and A2 clones showed that SEQ ID NO:12 and A2 clones were more closely related than SEQ ID NO:12 and A1 clones.

The partial nucleotide sequence (231, 207 and 180 nucleotides) of three Type B clones is shown in FIG. 8 (SEQ ID NOs 18, 19 and 20, respectively).

The cDNAs corresponding to genomic clones A2, B1 and B2 are cloned and sequenced in a manner similar to that described above. The derived amino acid sequences are aligned with known ACCase sequences. If putative CTP sequences are identified, functionality is tested as described below. Also if the tissue specificity and developmental timing of expression differ for different ACCase genes, the sequences of the promoter regions of the corresponding genomic clones are compared. Gene-specific probes for specific ACCase genes can provide more information on their roles in lipid synthesis (plastid and cytoplasmic isoforms), secondary metabolism (cytoplasmic isoforms), and herbicide resistance (likely plastid isoforms).

Only one plastidic ACCase polypeptide was identified by SDS-PAGE of maize leaf extracts, although 2-D gel analyses might provide evidence for a second, highly similar isoform. Of the two ACCase isoforms, only ACCase I shows altered herbicide inhibition in Acc1-S2 mutants, and most of the ACCase activity in leaves and developing embryos is herbicide-resistant and thus attributed to the Acc1-S2 gene product.

Although a 3' ACCase probe has been mapped both to chromosome 10 near Acc2-S5 and to chromosome 2, the conserved sequence of ACCase genes and lack of polymorphism in multiple bands complicates identification of genes encoded at these loci. The Type A1 ACCase gene is probably located on chromosome 2, since (I) 5' untranslated and chloroplast transit peptide probes from Type A1 hybridize to two bands (dark and light) in maize inbreds, and (ii) analysis of maize-oat addition lines carrying maize chromosomes 2 through 9 indicates the dark band is on chromosome 2 and the light band is on chromosome 1 or 10.

Type B ACCase genes are likely to encode cytosolic isoforms. Given that cytosolic malonyl-CoA is a precursor in the synthesis of many secondary metabolites including flavonoids (e.g. maysin, a corn silk component associated with corn earworm resistance), these cytosolic ACCases can have agronomic utility.

Northern blot analysis of total maize RNA with an ACCase probe (nucleotides 3400–5932) showed a single 8.3 kilobase band. To determine whether the expression of ACCase RNAs was developmentally regulated, blots of total RNA from 16 to 42 DAP (days after pollination) embryos were probed with an ACCase cDNA fragment. Transcript abundance peaked about 23 DAP and the steady state pattern was similar to in vitro ACCase enzyme activities and protein measured from developing embryos. Type A- and B-specific $^{32}$P-CTP-labeled antisense transcripts were 780 nt long (662 nt of ACCase sequence+118 nt of vector/promoter sequence) and were identical except for 15 base mismatches scattered along their length. Each antisense transcript was hybridized to total RNA from embryos at 16, 20, 23, and 42 DAP and digested with RNAse A/TI mixture to yield a 662-base fragment specific to the probe used. The results showed that the Type A transcript was more abundant than Type B at all tested stages, and that only Type A remained high in older embryos. Types A and B had similar expression patterns and peaked around 20–23 DAP. The ratio of Type A:B mRNA in leaves was about 2:1, similar to its relative abundance in cDNA expression libraries.

EXAMPLE VIII

Identification of a Second Herbicide Resistance Locus on Chromosome 10

To determine if sethoxydim and haloxyfop mutations segregated, all possible pairwise combinations of crosses were made between the sethoxydim (designated S1, S2, S3, S4, S5) or haloxyfop (designated H1, H2) tolerant mutant lines. The resulting F1 plants were test-crossed to wild-type susceptible plants. The testcross progeny were grown in the greenhouse and sprayed with Poast at a rate of 0.4 pounds/acre. If the two parents of the original cross had tolerance mutations in the same gene, then all testcross plants were expected to be heterozygous for a tolerance gene and would not segregate for wild-type susceptible plants. If the two parents had tolerance mutations in two different genes, then the testcross plants were expected to segregate for wild-type susceptible plants. Table VI below summarizes the results from these testcross progeny.

TABLE VI

| | PARENT 1 | | | | | |
|---|---|---|---|---|---|---|
| PARENT 2 | S2 | S3 | S4 | S5 | H1 | H2 |
| S1 | Res | Res | Res | Seg | Res | Res |
| S2 | | Res | Res | Seg | Res | Res |
| S3 | | | Res | Seg | Res | Res |
| S4 | | | | Seg | Res | Res |
| S5 | | | | | | Seg |
| H1 | | | | | | Res |

RES = all resistant testcross progeny
SEG = segregation for wildtype susceptible progeny at an approximate frequency of 25%

Subsequent to these analyses, another Acc resistance allele, S6, was identified. S6 is allelic to S5. S5 is a mutant Acc allele, which maps to chromosome 10, identified by Van Dee (an allele referred to as "M" in Van Dee, M.S. Thesis, University of Minnesota, 1994)).

These testcross progeny data clearly showed that the mutant line designated S5 was not allelic to any of the other sethoxydim-tolerant mutants. The tolerance gene, Acc2, was mapped to chromosome 10, flanked by umc155 and umc146 by a distance of 5.9 and 4.1 centimorgans (cM), respectively, by analyzing standard RFLP markers in an F2 population segregating for tolerance and susceptibility (VanDee, M.S. Thesis, University of Minnesota (1994)). The Acc2 locus is about 10 map units from gl, which is a "golden plant" phenotypic marker on the long arm of chromosome 10. The Acc2 mutant is designated Acc2-S5.

The testcross data also showed that all the mutant lines other than S5 have mutations in the same gene (Acc1) because their testcross progeny did not segregate. Thus, tissue culture selection for sethoxydim or haloxyfop resistance resulted in 7 independently isolated mutations representing 2 different, unlinked genes.

As described above, genomic clones representing at least 4 different ACCase genes have been isolated from a genomic library of the inbred line B73. The complete coding sequence for one gene (A1) was determined and, where determined, the coding sequences for the other clones were highly identical to that of A1. A1 has a functional chloroplast transit peptide sequence as expected for an ACCase that is localized in plastids. Another genomic clone (designated 5A) from the 5' end of the gene also contained a transit peptide sequence and other 5' sequences that differed slightly from A1. These results indicated that corn has at least 2 genes for plastidic ACCase. The 5' sequence differences between A1 and 5A (Type A2) genomic clones are useful in designing PCR primers that would be specific for either A1 or 5A (Type A2) genes. Restriction site differences in the upstream 5' regions for Type A1 and A2 genes may also be useful for RFLP mapping with gene-specific ACCase probes.

A 3' Type A1 ACCase cDNA probe mapped to chromosome 2 (Egli et al., *Maize Genetics Newsletter*, 68, 92 (1994)) and to chromosome 10 (Caffrey et al., *Maize Gen. Coop.*, 69, 3 (1995)). Two 5' Type A1 cDNA probes which span the transit peptide mapped to chromosome 2 in the same location as the 3' probe (see maize genetic map, 1996 version, Maize Genomic Database). Similar results were observed when the 5' or 3' probe was used to analyze total genomic DNA from some inbred lines relative to oat-corn additional lines. Both probes hybridized to two different fragments in total maize DNA but to only one fragment in oat-corn lines containing maize chromosome 2 and chromosome 3, 4, 5, 6, 7, 8 or 9 (Rines et al., In: *Modification of Gene Expression and NonMendelian Inheritance*, pp. 235–251 (1995)). Thus, A1 and A2, described hereinabove, appear to encode plastic ACCases that correspond to the Acc1 and Acc2 loci, respectively.

To identify segregating Acc1-S3 tolerance genes, a pair of PCR primers (28sst-97F,CCTTTTTATGGCACTGTGCG, SEQ ID NO:21) and 28sst-6t3+, CATCGTAGCCTATATGAGGACG, SEQ ID NO:22) were identified that amplify the 5' end of the A1 gene sequence from B73, which segregates with the resistance trait, but not from A188 or A641. These PCR primers are located in non-coding regions of A1 that span the chloroplast transit peptide. A control reaction employed a nearby 5' primer (28sst-a5+, SEQ ID NO:4) and 28sst-6t3+. The amplification reactions comprised 1 µl sense primer (from a 2.5 µM 10× stock solution), 1 µl anti-sense primer (from a 2.5 µM stock solution), 0.5–1.0 µl genomic DNA (1 µg/µl), 2.5 µl 10× Taq buffer (Promega), 2.5 µl MgCl$_2$ (Promega, stock solution is 25 mM), 0.5 µl of a dNTP stock solution (Promega, 10 mM stock solution), 0.25 µl Taq polymerase, and 24.75 µl water. DMSO at 5% can be added to the amplification reaction to improve specificity.

The following cycling parameters were used: 94° C. for 2 minutes for 1 cycle; 94° C. for 1 minute for 35 cycles; 54° for 1 minute and 74° C. for 70 seconds and then 4° C. Amplified products were analyzed by gel electrophoresis.

A nearby 5' primer (28sst-a5+, SEQ ID NO:4), when employed with 28sst-6t3+, amplified all genotypes and functioned as a positive control. In an F2 family segregating for the S3 source of sethoxydim tolerance, amplification of the A1 PCR product (528 bp which includes nucleotides corresponding to nucleotides 1–238 of SEQ ID NO:11, 29 bp of noncoding 5' sequence and 261 bp of 3' intronic sequence) was always associated with sethoxydim tolerance (29 tolerant plants were PCR+). The B73 PCR product was not detected in DNA from 15 of 17 susceptible plants (died after spraying), but was in 2 susceptible plants. If these plants died only from herbicide exposure and not from an unrelated cause, then the results indicate that the A1 PCR marker maps approximately 12 cM from the resistance locus. These results showed that the B73 chromosome was the donor of the Acc1-S3 tolerance gene in the selected tissue cultures and suggests that the Acc1 gene is at least closely linked to the A1 genomic clone.

EXAMPLE IX

Methods to Prepare a Two-Gene Heterozygous Herbicide Tolerant Hybrid

A preferred embodiment of the invention is an herbicide resistant inbred double homozygous maize plant (e.g., Inbred A (Acc1-S3/Acc1-S3;Acc2-S5/Acc2-S5)) that can be crossed to any normal susceptible inbred line. The resulting F1 contains one dominant allele for herbicide tolerance from each tolerance gene. The F1, which is grown by farmers, has herbicide tolerance equivalent to that given by single homozygous hybrids.

One method to prepare a two-gene heterozygous herbicide tolerant hybrid is to incorporate both tolerance genes at the end of inbred parent development. For example, cross Inbred A separately to S2 and to S5 homozygous mutant lines as shown:

| Inbred A x S2 | Inbred A x S5 |
|---|---|
| +/+; +/+ x Acc1-S2/Acc1-S2 | +/+; +/+ x Acc2-S5/Acc2-S5 |

This results in two genotypes each heterozygous for a different herbicide tolerance allele.

| Acc1-S2/+; +/+ | +/+; Acc2-S5/+ |
|---|---|

These genotypes are then backcrossed to Inbred A for the desired number of generations to recover the Inbred A parent. The susceptible plants segregating in each backcross generation can be eliminated by spraying with Poast. Segregating backcross progeny include:

| Inbred A x Acc1-S2/+; +/+ | Inbred A x +/+, Acc2-S5/+ |
|---|---|
| +/+; +/+ x Acc1-S2/+; +/+ | +/+, +/+ x +/+; Acc2-S5/+ |

Progeny

| | |
|---|---|
| +/+; +/+ (discard) | +/+; +/+ (discard) |
| Acc1-S2/+; +/+ (repeat cross) | +/+; Acc2-S5/+ (repeat cross) |

At end of backcrossing process, self pollinate to recover Inbred A with the homozygous mutant gene.

| | |
|---|---|
| Inbred A (Acc1-S2/Acc1-S2; +/+) | Inbred A (+/+; Acc2-SS/Acc2-S5) |

The two mutant versions of Inbred A are then crossed to produce double heterozygous mutant version of Inbred A: Inbred A (Acc1-S2/+; Acc2-S5/+)

Self pollinate to produce F2 generation segregating for the following genotypes:

| | |
|---|---|
| 1/16 | Acc1-S2/Acc1-S2; Acc2-S5/Acc2-S5 identify homozygote |
| 2/16 | Acc1-S2/Acc1-S2; Acc2-S5/+ |
| 1/16 | Acc1-S2/Acc1-S2; +/+; +/+ |
| 2/16 | Acc1-S2/+; Acc2-S5/Acc2-S5 |
| 4/16 | Acc1-S2/+; Acc2-S5/+ |
| 2/16 | Acc1-S2/+; +/+, +/+ |
| 1/16 | +/+; +/+; Acc2-S5/Acc2-S5 |
| 2/16 | +/+; +/+; Acc2-S5/+ |
| 1/16 | +/+; +/+; +/+; +/+ |

One sixteenth of the P2 plants are double homozygotes in Inbred A background. These F2 plants can be identified by:

a) Crossing F2 plants to susceptible plants and testing the progeny for sethoxydim tolerance. Plants homozygous for both genes produce nonsegregating double heterozygous testcross progeny that do not exhibit herbicide damage symptoms typical of single heterozygous mutant testcross genotypes.

b) Using RFLP molecular markers to identify chromosome regions that flank the Acc1 and Acc2 loci. Preferred RFLP markers flank and are tightly linked to, the ACCase coding sequences of Acc1 or Acc2. For instance, RFLP markers umc131 and umc2, or umc131 and uox, for the Acc1 region on chromosome 2 and umc155 and umc146, or umc155 and ncsu2, for the Acc2 region on chromosome 10 can be used to identify F2 plants homozygous for both sets of flanking polymorphisms from the tolerant mutant donor parents. It is also envisioned that other more closely, or distantly, linked flanking RFLP markers or genotype-specific ACCase probes can be used to identify the desired progeny.

c) Using PCR amplification which employs genotype-specific primers to detect the presence of a particular allele of either Acc1 or Acc2. For example, a primer that hybridizes to a region in the 5' untranslated portion of Acc1 and another primer that hybridizes to a region in the first intron of Acc1 are useful in an amplification reaction to detect the presence or absence of the fragment in progeny plants.

Another method to prepare a two-gene heterozygous herbicide tolerant hybrid is to incorporate both tolerance genes at the start of inbred parent development. For example, the two sources of tolerance (i.e., S2 and S5) are crossed to produce a double heterozygous mutant F1 genotype. This genotype is the equivalent of the Inbred A genotype indicated above (Acc1-S2/+;Accs-S5/+) except that the tolerance genes are not yet in the Inbred A background. The double heterozygous mutant F1 genotype is crossed to Inbred A and the resulting progeny plants analyzed for presence of the RFLP flanking markers for both Acc1 and Acc2 tolerance genes. Plants containing both sets of markers are used for the next cycle of backcrossing to Inbred A. The backcrossing and RFLP analysis are repeated for appropriate number of cycles to recover the Inbred A genotype. The final steps in developing the double homozygous mutant Inbred A genotype are the same as the final two steps in the incorporation of both tolerance genes at the end of inbred parent development (see above). The crossing of the inbred plant to a wild-type (susceptible) plant then results in a plant which is a hybrid double heterozygote.

A third method to prepare a two-gene heterozygous herbicide tolerant hybrid is to incorporate one tolerance gene into one inbred line (e.g., (Inbred A (Acc1-S3/Acc1-S3;+/+) and incorporate another tolerance gene into another inbred line (e.g., Inbred B (+/+;Acc2-S5/Acc2-S5). These two inbred lines are then crossed to produce a two-gene heterozygous herbicide tolerant hybrid.

EXAMPLE X

Field Tests of Herbicide Tolerant Double Heterozygotes

A double heterozygous hybrid was produced by crossing the following parent lines each homozygous for one of the sethoxydim tolerance mutations: Acc1-S2/Acc1-S2; +/+×+/+; Acc2-S5/Acc2-S5, where + represents the normal alleles for sethoxydim susceptibility. The resultant F1 (Acc1-S2/+; Acc2-S5/+) contained one copy of each sethoxydim-tolerant allele. Similar F1's were produced between S3 and S5 mutant lines.

Several double heterozygous F1 hybrids were tested for tolerance to sethoxydim (Poast) applications in the field in 1996. Poast was applied at the 6 to 8 leaf stage at a rate of 0.8 pounds/acre. Six days after application, visual ratings of the double heterozygous F1 hybrids unexpectedly indicated either no herbicide injury symptoms or slight symptoms on a few plants (<10%) as evidenced by transitory yellowing of leaves emerging from the whorl of the main stalk or from side tillers. These symptoms disappeared thirteen days after herbicide application. Similar results were obtained with the single mutant homozygous parent lines S2, S3 and S5. In contrast, single heterozygous F1 hybrids, obtained by crossing S2, S3 and S5 homozygous parent lines with normal susceptible lines, exhibited herbicide injury symptoms in most of the plants. These symptoms, especially yellowing of the tillers, persisted through flowering. Plants of normal susceptible lines were killed by this application.

Twenty-three days after the first application of herbicide, when tassels were emerging from most plants, another application of herbicide was performed (1.6 pounds Poast/acre). The double heterozygous F1 plants and the single homozygous parent lines showed little visible herbicide injury after the second treatment of the same plants. These herbicide applications showed that the herbicide tolerance of the double heterozygous F1 hybrids was equivalent to that of the single mutant homozygous parent lines. The response to herbicide treatment of hybrids with one mutant allele from each of the chromosome 2 and the chromosome 10 genes (i.e., Acc1-S2/+; Acc2-S5/+) was indistinguishable from the response of plants containing two mutant alleles from either gene (i.e., Acc1-S2/Acc1-S2; +/+ or +/+; Acc2-S5/Acc2-S5).

EXAMPLE XI

Greenhouse Trials of Herbicide Tolerant Double Heterozygotes

Two greenhouse trials were conducted to assess relative heterozygous sethoxydim resistant corn safety to $\frac{1}{8}x$, $\frac{1}{4}x$, ½×, 1×, 2×, and 4× use rates of POAST PLUS® in comparison to homozygous sethoxydim resistant corn and to sethoxydim susceptible corn (commercial Pioneer hybrid). Tolerance to sethoxydim was compared between double heterozygotes that contained the chromosome 2 resistance gene plus the chromosome 10 resistance gene, e.g., (Acc1-S3/+; Acc2-S5/+) to heterozygotes with only the chromosome 2 gene, e.g., (Acc1-S3/+; +/+) or the chromosome 10 gene (+/+; Acc2-S5/+).

The following plant genotypes and growth stages were employed in the greenhouse trials: 1) commercial homozygous sethoxydim resistant corn hybrid (*Zea mays*, var. DK 592$_{SR}$), growth stage-14 (4 leaves expanded); 2) commercial non-sethoxydim resistant corn hybrid (*Zea mays*, var. PI 3140), growth stage-14, 3) heterozygous sethoxydim resistant corn (*Zea mays*), growth stage-14. Sethoxydim (POAST PLUS, 120 g/l) was applied at 0.02 (⅛×), 0.04 ¼×), 0.09 (½×), 0.18 (1×), 0.36 (2×), and 0.71 (4×) lb aI/A (active ingredient per acre). The spray volume was 20 GPA (gallons per acre) and an adjuvant, ATPLUS® 411 F, was added at 1.2% v/v COC (crop oil concentrate).

Metro 360 soilless potting media was used. Osmocote 14-14-14 was applied at planting. STEM (Soluble Trace Element Mixture) and Peters 20-20-20 was applied within 3 days of germination and again 1 day after treatment at normal greenhouse use rates. Plants were watered overtop prior to application then subirrigated as needed. Plants were not exposed to UV light after application to maximize sethoxydim activity and potential injury. Corn plants were evaluated for percent injury at 7–8 and 14–15 days after treatment (DAT).

Results
GH Trial 067/96

Germination rates for the heterozygous sethoxydim resistant corn hybrids varied from 3 to 94 percent. Heterozygotes with the following line designations had germination rates of 80% or better and were included in GH trial 067/96: 4163/4142-2, 4142-2/4163, 4142-8/4158, 4158/4142-20, 4143-3/4160, 4143-1/4160. Heterozygotes with the following line designations did not have sufficient germination to test, most likely due to seed age (the seed was several years old): 4145-19/4160, 4144-12/4160, and 4142-7/4163. The heterozygotes in this trial all contained both chromosome 2 plus chromosome 10 resistance genes (homozygous chromosome 2 plants were crossed with homozygous chromosome 10 plants resulting in the same heterozygous genotype as results from a two gene homozygote crossed to a wild type). Homozygous mutant sources used in the crosses were S2 and S3 for the chromosome 2 gene location, and S5 for the chromosome 10 gene location.

Four of the six 2+10 double heterozygotes tested demonstrated less then 5% injury to the 2× rate (0.367 lb aI/A) of POAST PLUS (see Table VIII). Only 9% initial injury 7 DAT was observed to the 4× rate of POAST PLUS with one of the 2+10 heterozygotes (4163/4142-2). This degree of tolerance was almost as high as the chromosome 2 homozygous commercial hybrid DK 592sr. The susceptible Pioneer Hybrid 3140 was severely injured (22%) at the ⅛× use rate (0.02 lb ai/A) of POAST PLUS.

GH Trial 126/96

Chromosome 2 and chromosome 10 single heterozygotes were employed in a second comparative trial testing the best 2+10 double heterozygotes from trial 067/96 plus three new double heterozygotes produced in 1995, to these single heterozygotes. The chromosome 10 single heterozygotes demonstrated slight tolerance to sethoxydim in comparison to the susceptible Pioneer hybrid, through the plants were still injured 15 to 19% at 0.02 lb aI/A, 8 DAT (see Table IX). The chromosome 2 single heterozygotes demonstrated more tolerance than the chromosome 10 single heterozygotes but still demonstrated a range of 17 to 48% injury at 0.09 to 0.18 lb aI/A. All of the 2+10 double heterozygotes demonstrated excellent tolerance (0% injury) at 0.36 lb aI/A (2× rate) of POAST PLUS. Five of the seven double heterozygotes demonstrated less than 10% injury to POAST PLUS at 0.76 lb aI/A. This was better tolerance than was observed with the chromosome 10 single homozygous line, and almost equivalent to the tolerance observed with the chromosome 2 single homozygous commercial hybrid, DK 592sr.

Thus, double chromosome 2 plus chromosome 10 heterozygous resistant corn demonstrated greatly improved tolerance to sethoxydim as compared to chromosome 2 heterozygous material.

TABLE VIII

GH Trial 067/96 (Spray Volume = 20 GPA)

| Growth Stage | | % CORN INJURY GS 14 (4 Leaves Expanded at Application) | | | | | | | |
|---|---|---|---|---|---|---|---|---|---|
| Hybrids | | 2 + 10 4163/4142-2 | | 2 + 10 4142-2/4163 | | 2 + 10 4142-8/4158 | | 2 + 10 4158/4142-20 | |
| Treatment in lb aI/A | | 7 DAT | 14 DAT | 7 DAT | 14 DAT | 7 DAT | 14 DAT | 7 DAT | 14 DAT |
| ATPLUS 411 F 1.25% v/v + POAST PLUS | 0.02 | 0 | 0 | 0 | 0 | 0 | 0 | 2 | 0 |
| | 0.04 | 0 | 0 | 0 | 0 | 3 | 1 | 0 | 0 |
| | 0.09 | 0 | 0 | 0 | 0 | 3 | 0 | 3 | 0 |
| | 0.18 | 0 | 3 | 3 | 0 | 5 | 2 | 0 | 0 |
| | 0.36 | 0 | 2 | 3 | 2 | 3 | 2 | 0 | 0 |
| | 0.71 | 9 | 4 | 15 | 9 | 15 | 5 | 13 | 7 |
| Hybrids | | 2 homo DK 592$_{SR}$ | | Susceptible PI 3140 | | 2 + 10 4143-3/4160 | | 2 + 10 4143-1/4160 | |
| | | 7 DAT | 14 DAT | 7 DAT | 14 DAT | 7 DAT | 14 DAT | 7 DAT | 14 DAT |
| ATPLUS 411 F 1.25% v/v + POAST PLUS | 0.02 | 0 | 0 | 22 | 14 | 0 | 0 | 0 | 0 |
| | 0.04 | 0 | 0 | 30 | 78 | 0 | 0 | 2 | 0 |
| | 0.09 | 0 | 0 | 43 | 88 | 10 | 8 | 18 | 7 |

TABLE VIII-continued

GH Trial 067/96 (Spray Volume = 20 GPA)

| Growth Stage | | | | % CORN INJURY<br>GS 14 (4 Leaves Expanded at Application) | | | | | |
|---|---|---|---|---|---|---|---|---|---|
| | 0.18 | 0 | 0 | 85 | 99 | 45 | 60 | 20 | 23 |
| | 0.36 | 0 | 0 | 83 | 100 | | | | |
| | 0.71 | 4 | 0 | 93 | 100 | | | | |

TABLE IX

GH Trial 126/96

| Growth Stage | | | | | | | % CORN INJURY<br>GS 14 (4 Leaves Expanded at Application) | | | | | | | | |
|---|---|---|---|---|---|---|---|---|---|---|---|---|---|---|---|
| Hybrids | | 2 (single het)<br>A 156/6200-6 | | 10 (single het)<br>A 188/6202-7 | | 10 (single het)<br>A 188/6202-g | | 2 (single het)<br>A 188/6202-1 | | 2 + 10 het<br>4142-5/4158 | | 2 + 10 het<br>4158/4142-20 | | 2 + 10 het<br>4163/4142-2 | |
| Treatment in lb aI/A | | 8 DAT | 15 DAT | 8 DAT | 15 DAT | 8 DAT | 15 DAT | 8 DAT | 15 DAT | 8 DAT | 15 DAT | 8 DAT | 15 DAT | 8 DAT | 15 DAT |
| ATPLUS 411 F 1.25% v/v + | 0.02 | 3 | 0 | 19 | 13 | 15 | 9 | 0 | 0 | 0 | 0 | 0 | 0 | 0 | 0 |
| POAST PLUS | 0.04 | 18 | 9 | 43 | 45 | 33 | 38 | 3 | 3 | 0 | 0 | 0 | 0 | 0 | 0 |
| | 0.09 | 48 | 38 | 58 | 60 | 50 | 60 | 18 | 15 | 0 | 0 | 5 | 0 | 5 | 0 |
| | 0.18 | 28 | 17 | 68 | 58 | 63 | 58 | 17 | 8 | 0 | 0 | 0 | 0 | 0 | 0 |
| | 0.36 | 50 | 45 | 73 | 78 | 73 | 80 | 48 | 28 | 0 | 0 | 0 | 0 | 0 | 0 |
| | 0.71 | 63 | 53 | 78 | 95 | 78 | 100 | 65 | 40 | 7 | 7 | 0 | 3 | 5 | 4 |
| Hybrids | | 2 + 10 het<br>4142-2/4165 | | 2 + 10 het<br>6245 | | 2 + 10 het<br>6224 | | 2 + 10 het<br>6223 | | 10 hom0<br>6202-9 | | 2 hom0<br>DK 592$_{SR}$ | | Susceptible<br>PI 3140 | |
| | | 8 DAT | 15 DAT | 8 DAT | 15 DAT | 8 DAT | 15 DAT | 8 DAT | 15 DAT | 8 DAT | 15 DAT | 8 DAT | 15 DAT | 8 DAT | 15 DAT |
| ATPLUS 411 F 1.25% v/v + | 0.02 | 0 | 0 | 0 | 0 | 0 | 0 | 0 | 0 | 0 | 0 | 0 | 0 | 73 | 45 |
| POAST PLUS | 0.04 | 0 | 0 | 0 | 0 | 0 | 0 | 0 | 0 | 5 | 3 | 0 | 0 | 65 | 70 |
| | 0.09 | 0 | 0 | 5 | 0 | 0 | 0 | 0 | 0 | 9 | 4 | 0 | 0 | 78 | 93 |
| | 0.18 | 0 | 0 | 0 | 0 | 0 | 0 | 0 | 0 | 5 | 0 | 0 | 0 | 88 | 100 |
| | 0.36 | 0 | 0 | 0 | 0 | 0 | 0 | 0 | 0 | 13 | 7 | 0 | 0 | 99 | 100 |
| | 0.71 | 17 | 5 | 10 | 7 | 7 | 2 | 5 | 3 | 45 | 40 | 0 | 0 | 100 | 100 |

Spray Volume = 20 GPA

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed is:

1. A method to identify a plant which is a double heterozygote for a herbicide-tolerant allele of Acc1 and Acc2, the tolerance of which is at least twice that of a plant which is a single heterozygote for a herbicide-tolerant allele of Acc1 or Acc2 comprising: (a) crossing a first corn plant with a second corn plant so an to yield a progeny plant, wherein the fist plant is homozygous for an allele of Acc1 which imparts cyclohexanedione or aryloxyphenoxypropanoic acid herbicide tolerance, wherein the second plant is homozygous for an allele of Acc2 which imparts cyclohexanedione or aryloxyphenoxypropanoic acid herbicide tolerance, wherein the progeny plant is heterozygous as for the Acc1 allele which imparts cyclohexanodione or aryloxyphenoxypropanoic acid herbicide tolerance and heterozygous for the Acc2 allele which imparts cyclohexanedione or aryloxyphenoxypropanoic acid herbicide tolerance; and (b) identifying a progeny plant the tolerance of which is at least twice that of a corresponding corn plant that is heterozygous for the herbicide-tolerant allele of Acc1 or of a corresponding corn plant that is heterozygous for the herbicide-tolerant allele of Acc2.

2. The method of claim 1 wherein the first and second plant are substantially isogenic.

3. The method of claim 1 further comprising crossing the progeny plant to an inbred plant so as to yield a further progeny plant.

4. The method of claim 3, wherein the further progeny plant is crossed to an inbred for several generations until a progeny plant that is substantially isogenic with the inbred plant is obtained.

5. The method of claim 1 wherein the Acc1 alleles of the progeny plant are identified by an amplification reaction employing a polymerase chain reaction.

6. The method of claim 1 wherein the progeny plant is tolerant to levels of a cyclohexanedione or an aryloxyphenoxypyropanoic acid herbicide which inhibit a corresponding susceptible plant.

7. The method of claim 1 wherein the herbicide is selected from the group consisting of sethoxydim, haloxyfop, and mixtures thereof.

8. The method of claim 1 wherein the Acc1 allele imparts cyclohexanedione herbicide tolerance.

9. The method of claim 8, wherein th Acc1 allele is selected from the group consisting of Acc1-S1, Acc1-S2, Acc1-S3 and Acc1-S4.

10. The method of claim 1 wherein the Acc2 allele imparts cyclohexanadione herbicide tolerance.

11. The method of claim 10 wherein the Acc2 allele is selected from the group consisting of Acc2-S5 and Acc2-S6.

12. The method of claim 1 comprising obtaining seed from said progeny and obtaining further progeny plants.

13. The method of claim 12 wherein the progeny obtained are crossed back to a parent corn plant, to obtain further progeny.

14. The method of claim 13 wherein seeds are obtained from said further progeny plants and plants are recovered from said seed.

15. The method of claim 12 wherein said further progeny are crossed back to a parent corn plant, and progeny are obtained.

16. A progeny plant identified by the method of claim 1.

17. A seed the plant of claim 16.

18. A method to identify a hybrid plant which is a double heterozygote for a herbicide-tolerant allele of Acc1 and Acc2, the tolerance of which is at least twice that of a plant which is a single heterozygote for a herbicide-tolerant allele of Acc1 or Acc2 comprising: (a) crossing a first inbred corn plant with a second inbred corn plant so as to yield a progeny hybrid plant, wherein the first plant is homozygous for an allele of Acc1 which imparts cyclohexanedione or aryloxyphenoxypropanoic acid herbicide tolerance, wherein the second plant is homozygous for an allele of Acc2 which imparts cyclohexanedione or aryloxyphenoxypropanoic acid herbicide tolerance, wherein the progeny plant is heterozygous for the Acc1 allele which imparts cyclohexanedione or aryloxyphenoxypropanoic acid herbicide tolerance and heterozygous for the Acc2 allele which imparts cyclohexanedione or aryloxyphenoxypropanoic acid herbicide tolerance; and (b) identifying a progeny hybrid plant the tolerance of which is at least twice that of a corresponding corn plant that is heterozygous for the herbicide-tolerant allele of Acc1 or of a corresponding corn plant that is heterozygous for an herbicide-tolerant allele of Acc2.

19. The method of claim 18 wherein the progeny plant is tolerant to levels of a cyclohexanedione or an aryloxyphenoxypropanoic acid herbicide which inhibit a corresponding susceptible plant.

20. The method of claim 18 wherein the herbicide is selected from the group consisting of sethoxydim, haloxyfop, and mixtures thereof.

21. The method of claim 18 wherein the Acc1 allele imparts cyclohexanedione herbicide tolerance.

22. A method to identify a plant which is a double heterozygote for a herbicide-tolerant allele of Acc1 and Acc2, the tolerance of which is at least twice that of a plant which is a single heterozygote for a herbicide-tolerant allele of Acc1 or Acc2, comprising: (a) crossing a first corn plant with a second corn plant so as to yield a progeny plant, wherein the first plant is homozygous for an allele of Acc1 which imparts tolerance to an agent, wherein the second plant is homozygous for an allele of Acc2 which imparts tolerance to an agent, wherein the progeny plant is heterozygous for the Acc1 allele which imparts tolerance to an agent and heterozygous for the Acc2 allele which imparts tolerance to an agent, and wherein the agent is selected from the group consisting of 3-(2,4-dichlorophenyl)-perhydroindolizine-2,4-dione, 3-isopropyl-6-N-acetamido-1,3,5-triazine-2,4-(1H,3H)dione, soraphen A, and functional analogs thereof; and (b) identifying a progeny plant the tolerance of which is at least twice that of a corresponding corn plant that is heterozygous for the herbicide-tolerant allele of Acc1 or of a corresponding corn plant that is heterozygous for the herbicide-tolerant allele of Acc2.

23. The method of claim 21 or 22 wherein the Acc1 allele is selected from the group consisting of Acc1-S1, Acc1-S2, Acc1-S3, and Acc1-S4.

24. The method of claim 18 wherein the Acc2 allele imparts cyclohexanedione herbicide tolerance.

25. The method of claim 24 or 22 wherein the Acc2 allele is selected from the group consisting of Acc2-S5 and Acc2-S6.

26. A cyclohexanedione or aryloxyphenoxypropanoic acid herbicide tolerant *Zea mays* plant, the genome of which is heterozygous for an allele of Acc1 which imparts cyclohexanedione or aryloxyphenoxypropanoic acid herbicide tolerance, and is heterozygous for an allele of Acc2 which imparts cyclohexanedione or aryloxyphenoxypropanoic acid herbicide tolerance, and wherein the tolerance of the plant is at least twice that of a corresponding corn plant that is heterozygous for an herbicide-tolerant allele of Acc1 or of a corresponding corn plant that is heterozygous for an herbicide-tolerant allele of Acc2.

27. The plant of claim 26 wherein the plant is resistant or tolerant to an amount of herbicide that is toxic to a corresponding susceptible *Zea mays* plant.

28. The plant of claim 26 which is resistant or tolerant to an herbicide selected from the group consisting of sethoxydim, haloxyfop, and mixtures thereof.

29. The plant of claim 26 wherein the Acc1 allele is selected from the group consisting of Acc1-S1, Acc1-S2, Acc1-S3 and Acc1-S4.

30. The plant of claim 26 wherein the Acc2 allele is selected from the group consisting of Acc2-S5 and Acc2-S6.

31. The plant of claim 26 which is a hybrid plant.

* * * * *

UNITED STATES PATENT AND TRADEMARK OFFICE
CERTIFICATE OF CORRECTION

PATENT NO.    : 6,414,222 B1                                                      Page 1 of 1
DATED         : July 2, 2002
INVENTOR(S)   : Burle G. Gengenbach et al.

It is certified that error appears in the above-identified patent and that said Letters Patent is hereby corrected as shown below:

<u>Title page,</u>
Item [56], FOREIGN PATENT DOCUMENTS, delete "WO98/07647" and insert
-- WO89/07647 --, therefor.
Delete "92/11243" and insert -- 93/11243 --, therefor <u>Column 65,</u>
Line 62, delete "an" after "so" and insert -- as --, therefor.

<u>Column 67,</u>
Line 12, delete "aryloxyphenoxpyropanoic" and insert -- aryloxyphenoxypropanoic --, therefor.
Line 24, delete "cyclohexanadione" and insert -- cyclohexanedione --, therefor.
Line 39, insert -- of -- after "seed".

Signed and Sealed this

First Day of April, 2003

JAMES E. ROGAN
*Director of the United States Patent and Trademark Office*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 258 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GTTCCTGCAA ACATTGGTGG ACCTCTTCCT ATTACCAAAC CTCTGGACCC TCCAGACAGA      60

CCTGTTGCTT ACATCCCTGA GAACACATGC GATCCACGTG CAGCTATCTG TGGTGTAGAT     120
```

```
GACAGCCAAG GGAAATGGTT GGGTGGTATG TTTGACAAAG ACAGCTTTGT GGAGACATTT    180

GAAGGATGGG CAAAAACAGT GGTTACTGGC AGAGCAAAGC TTGGAGGAAT CCTGTGGGC     240

GTCATAGCTG TGGAGACA                                                  258
```

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:2:

```
Val Met Lys Met
 1
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGATATATGC TTTGGTGGAA TCTGGC                                         26
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GGTCTTCAAT TGTGCTGTCT GG                                             22
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CCTTGACGAA CAGACTGGCT GTGC                                           24
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CACAGCCAGT CTGTTCGTCA AGG                                              23

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

CCTCTACGTA ATTGGTCAGC                                                  20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

CATAGCTATG GCAACTCCGG                                                  20

(2) INFORMATION FOR SEQ ID NO:9:

(i) SEQUENCE CHARACTERISTICS:
            (A) LENGTH: 7470 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

GGTCTTCAAT TGTGCTGTCT GGGCCACGGA ACGACAATGT CACAGCTTGG ATTAGCCGCA       60

GCTGCCTCAA AGGCCTTGCC ACTACTCCCT AATCGCCAGA GAAGTTCAGC TGGGACTACA      120

TTCTCATCAT CTTCATTATC GAGGCCCTTA AACAGAAGGA AAAGCCATAC TCGTTCACTC      180

CGTGATGGCG GAGATGGGGT ATCAGATGCC AAAAAGCACA GCCAGTCTGT TCGTCAAGGT      240

CTTGCTGGCA TTATCGACCT CCCAAGTGAG GCACCTTCCG AAGTGGATAT TTCACATGGA      300

TCTGAGGATC CTAGGGGGCC AACAGATTCT TATCAAATGA ATGGGATTAT CAATGAAACA      360

CATAATGGAA GACATGCCTC AGTGTCCAAG GTTGTTGAAT TTTGTGCGGC ACTAGGTGGC      420

AAAACACCAA TTCACAGTAT ATTAGTGGCC AACAATGGAA TGGCAGCAGC AAAATTTATG      480

AGGAGTGTCC GGACATGGGC TAATGATACT TTTGGATCTG AGAAGGCAAT TCAACTCATA      540

GCTATGGCAA CTCCGGAAGA CATGAGGATA AATGCAGAAC ACATTAGAAT TGCTGACCAA      600

TTCGTAGAGG TGCCTGGTGG AACAAACAAT AATAACTACG CCAATGTTCA ACTCATAGTG      660

GGGATGGCAC AAAAACTAGG TGTTTCTGCT GTTTGGCCTG GTTGGGGTCA TGCTTCTGAG      720

AATCCTGAAC TGCCAGATGC ATTGACCGCA AAAGGGATCG TTTTTCTTGG CCCACCTGCA      780

TCATCAATGA ATGCTTTGGG AGATAAGGTC GGCTCAGCTC TCATTGCTCA AGCAGCCGGG      840

GTCCCAACTC TTGCTTGGAG TGGATCACAT GTTGAAGTTC CATTAGAGTG CTGCTTAGAC      900

```
GCGATACCTG AGGAGATGTA TAGAAAAGCT TGCGTTACTA CCACAGAGGA AGCAGTTGCA    960

AGTTGTCAAG TGGTTGGTTA TCCTGCCATG ATTAAGGCAT CCTGGGGAGG TGGTGGTAAA   1020

GGAATAAGAA AGGTTCATAA TGATGATGAG GTTAGAGCGC TGTTTAAGCA AGTACAAGGT   1080

GAAGTCCCTG GCTCCCCAAT ATTTGTCATG AGGCTTGCAT CCCAGAGTCG GCATCTTGAA   1140

GTTCAGTTGC TTTGTGATCA ATATGGTAAT GTAGCAGCAC TTCACAGTCG TGATTGCAGT   1200

GTGCAACGGC GACACCAGAA GATTATTGAA GAAGGTCCAG TTACTGTTGC TCCTCGTGAG   1260

ACAGTTAAAG CACTTGAGCA GGCAGCAAGG AGGCTTGCTA AGGCTGTGGG TTATGTTGGT   1320

GCTGCTACTG TTGAGTATCT TTACAGCATG GAAACTGGAG ACTACTATTT TCTGGAACTT   1380

AATCCCCGAC TACAGGTTGA GCATCCAGTC ACTGAGTGGA TAGCTGAAGT GAATCTGCCT   1440

GCAGCTCAAG TTGCTGTTGG AATGGGCATA CCTCTTTGGC AGATTCCAGA AATCAGACGT   1500

TTCTATGGAA TGGACTATGG AGGAGGGTAT GACATTTGGA GGAAAACAGC AGCTCTTGCT   1560

ACACCATTTA ATTTTGATGA AGTAGATTCT CAATGGCCAA AGGGCCATTG TGTAGCAGTT   1620

AGAATTACTA GTGAGGACCC AGATGATGGT TTCAAACCTA CTGGTGGGAA AGTGAAGGAG   1680

ATAAGTTTTA AAAGCAAGCC TAATGTTTGG GCCTACTTCT CAGTAAAGTC TGGTGGAGGC   1740

ATTCATGAAT TTGCTGATTC TCAGTTTGGA CATGCTTTTG CATATGGACT CTCTAGACCA   1800

GCAGCTATAA CAAACATGTC TCTTGCATTA AAAGAGATTC AGATTCGTGG AGAAATTCAT   1860

TCAAATGTTG ATTACACAGT TGACCTCTTA AACGCTTCAG ACTTCAGAGA AACAAGATC   1920

CACACTGGTT GGCTGGATAC AAGAATAGCT ATGCGTGTTC AAGCTGAGAG GCCCCCATGG   1980

TATATCTCAG TGGTTGGAGG TGCTTTATAT AAAACAGTAA CCACCAATGC AGCCACTGTT   2040

TCTGAATATG TTAGTTATCT CACCAAGGGC CATATTCCAC CAAAGCATAT ATCCCTTGTC   2100

AATTCTACAG TTAATTTGAA TATAGAAGGG AGCAAATACA CAATTGAAAC TGTAAGGACT   2160

GGACATGGTA GCTACAGGTT GAGAATGAAT GATTCAACAG TTGAAGCGAA TGTACAATCT   2220

TTATGTGATG GTGGCCTCTT AATGCAGTTG GATGGAAACA GCCATGTAAT TTATGCAGAA   2280

GAAGAAGCTG GTGGTACACG GCTTCAGATT GATGGAAAGA CATGTTTATT GCAGAATGAC   2340

CATGATCCAT CGAAGTTATT AGCTGAGACA CCCTGCAAAC TTCTTCGTTT CTTGGTTGCT   2400

GATGGTGCTC ATGTTGATGC GGATGTACCA TACGCGGAAG TTGAGGTTAT GAAGATGTGC   2460

ATGCCTCTCT TGTCACCTGC TTCTGGTGTC ATTCATTGTA TGATGTCTGA GGGCCAGGCA   2520

TTGCAGGCTG GTGATCTTAT AGCAAGGTTG GATCTTGATG ACCCTTCTGC TGTGAAAAGA   2580

GCTGAGCCAT TTGATGGAAT ATTTCCACAA ATGGAGCTCC CTGTTGCTGT CTCTAGTCAA   2640

GTACACAAAA GATATGCTGC AAGTTTGAAT GCTGCTCGAA TGGTCCTTGC AGGATATGAG   2700

CACAATATTA ATGAAGTCGT TCAAGATTTG GTATGCTGCC TGGACAACCC TGAGCTTCCT   2760

TTCCTACAGT GGGATGAACT TATGTCTGTT CTAGCAACGA GGCTTCCAAG AAATCTCAAG   2820

AGTGAGTTAG AGGATAAATA CAAGGAATAC AAGTTGAATT TTTACCATGG AAAAAACGAG   2880

GACTTTCCAT CCAAGTTGCT AAGAGACATC ATTGAGGAAA ATCTTTCTTA TGGTTCAGAG   2940

AAGGAAAAGG CTACAAATGA GAGGCTTGTT GAGCCTCTTA TGAACCTACT GAAGTCATAT   3000

GAGGGTGGGA GAGAGAGCCA TGCACATTTT GTTGTCAAGT CTCTTTTCGA GGAGTATCTT   3060

ACAGTGGAAG AACTTTTTAG TGATGGCATT CAGTCTGACG TGATTGAAAC ATTGCGGCAT   3120

CAGCACAGTA AAGACCTGCA GAAGGTTGTA GACATTGTGT TGTCTCACCA GGGTGTGAGG   3180

AACAAAGCTA AGCTTGTAAC GGCACTTATG GAAAAGCTGG TTTATCCAAA TCCTGGTGGT   3240

TACAGGGATC TGTTAGTTCG CTTTTCTTCC CTCAATCATA AAAGATATTA TAAGTTGGCC   3300
```

```
CTTAAAGCAA GTGAACTTCT TGAACAAACC AAACTAAGTG AACTCCGTGC AAGCGTTGCA    3360

AGAAGCCTTT CGGATCTGGG GATGCATAAG GGAGAAATGA GTATTAAGGA TAACATGGAA    3420

GATTTAGTCT CTGCCCCATT ACCTGTTGAA GATGCTCTGA TTTCTTTGTT TGATTACAGT    3480

GATCGAACTG TTCAGCAGAA AGTGATTGAG ACATACATAT CACGATTGTA CCAGCCTCAT    3540

CTTGTAAAGG ATAGCATCCA AATGAAATTC AAGGAATCTG GTGCTATTAC TTTTTGGGAA    3600

TTTTATGAAG GCATGTTGA TACTAGAAAT GGACATGGGG CTATTATTGG TGGGAAGCGA    3660

TGGGGTGCCA TGGTCGTTCT CAAATCACTT GAATCTGCGT CAACAGCCAT TGTGGCTGCA    3720

TTAAAGGATT CGGCACAGTT CAACAGCTCT GAGGGCAACA TGATGCACAT TGCATTATTG    3780

AGTGCTGAAA ATGAAAGTAA TATAAGTGGA ATAAGCAGTG ATGATCAAGC TCAACATAAG    3840

ATGGAAAAGC TTAGCAAGAT ACTGAAGGAT ACTAGCGTTG CAAGTGATCT CCAAGCTGCT    3900

GGTTTGAAGG TTATAAGTTG CATTGTTCAA AGAGATGAAG CTCGCATGCC AATGCGCCAC    3960

ACATTCCTCT GGTTGGATGA CAAGAGTTGT TATGAAGAAG AGCAGATTCT CCGGCATGTG    4020

GAGCCTCCCC TCTCTACACT TCTTGAATTG GATAAGTTGA AGGTGAAAGG ATACAATGAA    4080

ATGAAGTATA CTCCTTCGCG TGACCGCCAA TGGCATATCT ACACACTAAG AAATACTGAA    4140

AACCCCAAAA TGTTGCATAG GGTGTTTTTC CGAACTATTG TCAGGCAACC CAATGCAGGC    4200

AACAAGTTTA GATCGGCTCA GATCAGCGAC GCTGAGGTAG GATGTCCCGA AGAATCTCTT    4260

TCATTTACAT CAAATAGCAT CTTAAGATCA TTGATGACTG CTATTGAAGA ATTAGAGCTT    4320

CATGCAATTA GGACAGGTGA TTCTCACATG TATTTGTGCA TACTGAAAGA GCAAAAGCTT    4380

CTTGACCTCA TTCCATTTTC AGGGAGTACA ATTGTTGATG TTGGCCAAGA TGAAGCTACC    4440

GCTTGTTCAC TTTTAAAATC AATGGCTTTG AAGATACATG AGCTTGTTGG TGCAAGGATG    4500

CATCATCTGT CTGTATGCCA GTGGGAGGTG AAACTCAAGT TGGACTGTGA TGGCCCTGCA    4560

AGTGGTACCT GGAGAGTTGT AACTACAAAT GTTACTGGTC ACACCTGCAC CATTGATATA    4620

TACCGAGAAG TGGAGGAAAT AGAATCACAG AAGTTAGTGT ACCATTCAGC CAGTTCGTCA    4680

GCTGGACCAT TGCATGGTGT TGCACTGAAT AATCCATATC AACCTTTGAG TGTGATTGAT    4740

CTAAAGCGCT GCTCTGCTAG GAACAACAGA ACAACATATT GCTATGATTT TCCGCTGGCC    4800

TTTGAAACTG CACTGCAGAA GTCATGGCAG TCCAATGGCT CTACTGTTTC TGAAGGCAAT    4860

GAAAATAGTA AATCCTACGT GAAGGCAACT GAGCTAGTGT TTGCTGAAAA ACATGGGTCC    4920

TGGGGCACTC CTATAATTCC GATGGAACGC CCTGCTGGGC TCAACGCACT TGGTATGGTC    4980

GCTTGGATCA TGGAGATGTC AACACCTGAA TTTCCCAATG GCAGGCAGAT TATTGTTGTA    5040

GCAAATGATA TCACTTTCAG AGCTGGATCA TTTGGCCCAA GGGAAGATGC ATTTTTTGAA    5100

ACTGTCACTA ACCTGGCTTG CGAAAGGAAA CTTCCTCTTA TATACTTGGC AGCAAACTCT    5160

GGTGCTAGGA TTGGCATAGC TGATGAAGTA AAATCTTGCT TCCGTGTTGG ATGGTCTGAC    5220

GAAGGCAGTC CTGAACGAGG GTTTCAGTAC ATCTATCTGA CTGAAGAAGA CTATGCTCGC    5280

ATTAGCTCTT CTGTTATAGC ACATAAGCTG GAGCTAGATA GTGGTGAAAT TAGGTGGATT    5340

ATTGACTCTG TTGTGGGCAA GGAGGATGGG CTTGGTGTCG AGAACATACA TGGAAGTGCT    5400

GCTATTGCCA GTGCTTATTC TAGGGCATAT GAGGAGACAT TTACACTTAC ATTTGTGACT    5460

GGGCGGACTG TAGGAATAGG AGCTTATCTT GCTCGACTTG GTATACGGTG CATACAGCGT    5520

CTTGACCAGC CTATTATTTT AACAGGGTTT TCTGCCCTGA ACAAGCTCCT TGGGCGGGAA    5580

GTGTACAGCT CCCACATGCA GCTTGGTGGT CCTAAGATCA TGGCGACCAA TGGTGTTGTC    5640

CACCTCACTG TTCCAGATGT CCTTGAAGGT GTTTCCAATA TATTGAGGTG GCTCAGCTAT    5700
```

```
GTTCCTGCAA ACATTGGTGG ACCTCTTCCT ATTACCAAAC CTCTGGACCC TCCAGACAGA    5760

CCTGTTGCTT ACATCCCTGA GAACACATGC GATCCACGTG CAGCTATCTG TGGTGTAGAT    5820

GACAGCCAAG GGAAATGGTT GGGTGGTATG TTTGACAAAG ACAGCTTTGT GGAGACATTT    5880

GAAGGATGGG CAAAAACAGT GGTTACTGGC AGAGCAAAGC TTGGAGGAAT TCCTGTGGGC    5940

GTCATAGCTG TGGAGACACA GACCATGATG CAGATCATCC CTGCTGATCA AGGTCAGCTT    6000

GATTCCCATG AGCGATCTGT CCCTCGTGCT GGACAAGTGT GGTTCCCAGA TTCTGCAACC    6060

AAGACCGCTC AGGCATTATT AGACTTCAAC CGTGAAGGAT GCCTCTGTT CATCCTGGCT      6120

AATTGGAGAG GCTTCTCTGG TGGACAAAGA GATCTCTTTG AAGGAATTCT TCAGGCTGGG    6180

TCAACAATTG TCGAGAACCT TAGGACATAT AATCAGCCTG CTTTTGTGTA CATTCCTATG    6240

GCTGGAGAGC TTCGTGGAGG AGCTTGGGTT GTGGTCGATA GCAAAATAAA TCCAGACCGC    6300

ATTGAGTGTT ATGCTGAAAG GACTGCCAAA GGTAATGTTC TCGAACCTCA AGGGTTAATT    6360

GAAATCAAGT TCAGGTCAGA GGAACTCCAA GACTGTATGG GTAGGCTTGA CCCAGAGTTG    6420

ATAAATCTGA AAGCAAAACT CCAAGATGTA AATCATGGAA ATGGAAGTCT ACCAGACATA    6480

GAAGGGATTC GGAAGAGTAT AGAAGCACGT ACGAAACAGT TGCTGCCTTT ATATACCCAG    6540

ATTGCAATAC GGTTTGCTGA ATTGCATGAT ACTTCCCTAA GAATGGCAGC TAAAGGTGTG    6600

ATTAAGAAAG TTGTAGACTG GGAAGAATCA CGCTCGTTCT TCTATAAAAG GCTACGGAGG    6660

AGGATCGCAG AAGATGTTCT TGCAAAAGAA ATAAGGCAGA TAGTCGGTGA TAAATTTACG    6720

CACCAATTAG CAATGGAGCT CATCAAGGAA TGGTACCTTG CTTCTCAGGC CACAACAGGA    6780

AGCACTGGAT GGGATGACGA TGATGCTTTT GTTGCCTGGA AGGACAGTCC TGAAAACTAC    6840

AAGGGGCATA TCCAAAAGCT TAGGGCTCAA AAAGTGTCTC ATTCGCTCTC TGATCTTGCT    6900

GACTCCAGTT CAGATCTGCA AGCATTCTCG CAGGGTCTTT CTACGCTATT AGATAAGATG    6960

GATCCCTCTC AGAGAGCGAA GTTTGTTCAG GAAGTCAAGA AGGTCCTTGA TTGATGATAC    7020

CAACACATCC AACACAATGT GTGCATGTCA CATCTTTTTG TTCTAGTACA TACATAGAAG    7080

GATATTGCTT GGTCTTGATT GATCATGTCT GATTTAAGTC GACTATTATT CTTGGAATT     7140

TTCTTTTGGA CCTGGTGCTA TGGTTGATGG ATGTATATTG GATATGTGCG TTCTGCCAGG    7200

TGTAAGCACA AAGGTTTAGA CARAMMRARA RCAAGAGCGA GTGAACCTGT TCTGGTTTTG    7260

CAGTGGTTCA GTAAGGCAGA AAGTTGTTAA ACCGTAGTTC TGAGATGTAT TACCAGTGNC    7320

GCCATGCTGT ACTTTTAGGG TGTATAATGC GGATACAAAT AAACAATTTA GCGGTTCATT    7380

AAAGTTTGAA CTCAAATAAC ATGTTCTTTG TAAGCATATG TACCGTACCT CTACGTGAAA    7440

TAAAGTTGTT GAATTAGCAT TCGAAAAAA                                      7470
```

(2) INFORMATION FOR SEQ ID NO:10:

(i) SEQUENCE CHARACTERISTICS:
        (A) LENGTH: 2325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Ser Gln Leu Gly Leu Ala Ala Ala Ser Lys Ala Leu Pro Leu
 1               5                  10                  15

Leu Pro Asn Arg Gln Arg Ser Ser Ala Gly Thr Thr Phe Ser Ser Ser
            20                  25                  30
```

-continued

```
Ser Leu Ser Arg Pro Leu Asn Arg Arg Lys Ser His Thr Arg Ser Leu
         35                  40                  45

Arg Asp Gly Gly Asp Gly Val Ser Asp Ala Lys Lys His Ser Gln Ser
     50                  55                  60

Val Arg Gln Gly Leu Ala Gly Ile Ile Asp Leu Pro Ser Glu Ala Pro
 65                  70                  75                  80

Ser Glu Val Asp Ile Ser His Gly Ser Glu Asp Pro Arg Gly Pro Thr
                 85                  90                  95

Asp Ser Tyr Gln Met Asn Gly Ile Ile Asn Glu Thr His Asn Gly Arg
             100                 105                 110

His Ala Ser Val Ser Lys Val Val Glu Phe Cys Ala Ala Leu Gly Gly
         115                 120                 125

Lys Thr Pro Ile His Ser Ile Leu Val Ala Asn Asn Gly Met Ala Ala
 130                 135                 140

Ala Lys Phe Met Arg Ser Val Arg Thr Trp Ala Asn Asp Thr Phe Gly
 145                 150                 155                 160

Ser Glu Lys Ala Ile Gln Leu Ile Ala Met Ala Thr Pro Glu Asp Met
                 165                 170                 175

Arg Ile Asn Ala Glu His Ile Arg Ile Ala Asp Gln Phe Val Glu Val
             180                 185                 190

Pro Gly Gly Thr Asn Asn Asn Tyr Ala Asn Val Gln Leu Ile Val
         195                 200                 205

Gly Met Ala Gln Lys Leu Gly Val Ser Ala Val Trp Pro Gly Trp Gly
 210                 215                 220

His Ala Ser Glu Asn Pro Glu Leu Pro Asp Ala Leu Thr Ala Lys Gly
 225                 230                 235                 240

Ile Val Phe Leu Gly Pro Pro Ala Ser Ser Met Asn Ala Leu Gly Asp
                 245                 250                 255

Lys Val Gly Ser Ala Leu Ile Ala Gln Ala Ala Gly Val Pro Thr Leu
             260                 265                 270

Ala Trp Ser Gly Ser His Val Glu Val Pro Leu Glu Cys Cys Leu Asp
         275                 280                 285

Ala Ile Pro Glu Glu Met Tyr Arg Lys Ala Cys Val Thr Thr Thr Glu
 290                 295                 300

Glu Ala Val Ala Ser Cys Gln Val Val Gly Tyr Pro Ala Met Ile Lys
 305                 310                 315                 320

Ala Ser Trp Gly Gly Gly Gly Lys Gly Ile Arg Lys Val His Asn Asp
                 325                 330                 335

Asp Glu Val Arg Ala Leu Phe Lys Gln Val Gln Gly Glu Val Pro Gly
             340                 345                 350

Ser Pro Ile Phe Val Met Arg Leu Ala Ser Gln Ser Arg His Leu Glu
         355                 360                 365

Val Gln Leu Leu Cys Asp Gln Tyr Gly Asn Val Ala Ala Leu His Ser
 370                 375                 380

Arg Asp Cys Ser Val Gln Arg Arg His Gln Lys Ile Ile Glu Glu Gly
 385                 390                 395                 400

Pro Val Thr Val Ala Pro Arg Glu Thr Val Lys Ala Leu Glu Gln Ala
                 405                 410                 415

Ala Arg Arg Leu Ala Lys Ala Val Gly Tyr Val Gly Ala Ala Thr Val
             420                 425                 430

Glu Tyr Leu Tyr Ser Met Glu Thr Gly Asp Tyr Tyr Phe Leu Glu Leu
         435                 440                 445
```

-continued

```
Asn Pro Arg Leu Gln Val Glu His Pro Val Thr Glu Trp Ile Ala Glu
        450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
                500                 505                 510

Phe Asp Glu Val Asp Ser Gln Trp Pro Lys Gly His Cys Val Ala Val
            515                 520                 525

Arg Ile Thr Ser Glu Asp Pro Asp Gly Phe Lys Pro Thr Gly Gly
530                 535                 540

Lys Val Lys Glu Ile Ser Phe Lys Ser Lys Pro Asn Val Trp Ala Tyr
545                 550                 555                 560

Phe Ser Val Lys Ser Gly Gly Ile His Glu Phe Ala Asp Ser Gln
                565                 570                 575

Phe Gly His Ala Phe Ala Tyr Gly Leu Ser Arg Pro Ala Ala Ile Thr
            580                 585                 590

Asn Met Ser Leu Ala Leu Lys Glu Ile Gln Ile Arg Gly Glu Ile His
                595                 600                 605

Ser Asn Val Asp Tyr Thr Val Asp Leu Leu Asn Ala Ser Asp Phe Arg
610                 615                 620

Glu Asn Lys Ile His Thr Gly Trp Leu Asp Thr Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Val Thr Thr Asn Ala Ala Thr Val Ser Glu Tyr Val
                660                 665                 670

Ser Tyr Leu Thr Lys Gly His Ile Pro Pro Lys His Ile Ser Leu Val
            675                 680                 685

Asn Ser Thr Val Asn Leu Asn Ile Glu Gly Ser Lys Tyr Thr Ile Glu
690                 695                 700

Thr Val Arg Thr Gly His Gly Ser Tyr Arg Leu Arg Met Asn Asp Ser
705                 710                 715                 720

Thr Val Glu Ala Asn Val Gln Ser Leu Cys Asp Gly Gly Leu Leu Met
                725                 730                 735

Gln Leu Asp Gly Asn Ser His Val Ile Tyr Ala Glu Glu Ala Gly
            740                 745                 750

Gly Thr Arg Leu Gln Ile Asp Gly Lys Thr Cys Leu Leu Gln Asn Asp
            755                 760                 765

His Asp Pro Ser Lys Leu Leu Ala Glu Thr Pro Cys Lys Leu Leu Arg
770                 775                 780

Phe Leu Val Ala Asp Gly Ala His Val Asp Ala Asp Val Pro Tyr Ala
785                 790                 795                 800

Glu Val Glu Val Met Lys Met Cys Met Pro Leu Leu Ser Pro Ala Ser
                805                 810                 815

Gly Val Ile His Cys Met Met Ser Glu Gly Gln Ala Leu Gln Ala Gly
                820                 825                 830

Asp Leu Ile Ala Arg Leu Asp Leu Asp Asp Pro Ser Ala Val Lys Arg
            835                 840                 845

Ala Glu Pro Phe Asp Gly Ile Phe Pro Gln Met Glu Leu Pro Val Ala
850                 855                 860
```

-continued

```
Val Ser Ser Gln Val His Lys Arg Tyr Ala Ser Leu Asn Ala Ala
865                 870                 875                 880

Arg Met Val Leu Ala Gly Tyr Glu His Asn Ile Asn Glu Val Val Gln
                885                 890                 895

Asp Leu Val Cys Cys Leu Asp Asn Pro Glu Leu Pro Phe Leu Gln Trp
                900                 905                 910

Asp Glu Leu Met Ser Val Leu Ala Thr Arg Leu Pro Arg Asn Leu Lys
            915                 920                 925

Ser Glu Leu Glu Asp Lys Tyr Lys Glu Tyr Lys Leu Asn Phe Tyr His
    930                 935                 940

Gly Lys Asn Glu Asp Phe Pro Ser Lys Leu Leu Arg Asp Ile Ile Glu
945                 950                 955                 960

Glu Asn Leu Ser Tyr Gly Ser Glu Lys Glu Lys Ala Thr Asn Glu Arg
                965                 970                 975

Leu Val Glu Pro Leu Met Asn Leu Leu Lys Ser Tyr Glu Gly Gly Arg
                980                 985                 990

Glu Ser His Ala His Phe Val Val Lys Ser Leu Phe Glu Glu Tyr Leu
            995                 1000                1005

Thr Val Glu Glu Leu Phe Ser Asp Gly Ile Gln Ser Asp Val Ile Glu
    1010                1015                1020

Thr Leu Arg His Gln His Ser Lys Asp Leu Gln Lys Val Val Asp Ile
025                 1030                1035                1040

Val Leu Ser His Gln Gly Val Arg Asn Lys Ala Lys Leu Val Thr Ala
                1045                1050                1055

Leu Met Glu Lys Leu Val Tyr Pro Asn Pro Gly Gly Tyr Arg Asp Leu
                1060                1065                1070

Leu Val Arg Phe Ser Ser Leu Asn His Lys Arg Tyr Tyr Lys Leu Ala
            1075                1080                1085

Leu Lys Ala Ser Glu Leu Leu Glu Gln Thr Lys Leu Ser Glu Leu Arg
    1090                1095                1100

Ala Ser Val Ala Arg Ser Leu Ser Asp Leu Gly Met His Lys Gly Glu
105                 1110                1115                1120

Met Ser Ile Lys Asp Asn Met Glu Asp Leu Val Ser Ala Pro Leu Pro
                1125                1130                1135

Val Glu Asp Ala Leu Ile Ser Leu Phe Asp Tyr Ser Asp Arg Thr Val
            1140                1145                1150

Gln Gln Lys Val Ile Glu Thr Tyr Ile Ser Arg Leu Tyr Gln Pro His
    1155                1160                1165

Leu Val Lys Asp Ser Ile Gln Met Lys Phe Lys Glu Ser Gly Ala Ile
    1170                1175                1180

Thr Phe Trp Glu Phe Tyr Glu Gly His Val Asp Thr Arg Asn Gly His
185                 1190                1195                1200

Gly Ala Ile Ile Gly Gly Lys Arg Trp Gly Ala Met Val Val Leu Lys
                1205                1210                1215

Ser Leu Glu Ser Ala Ser Thr Ala Ile Val Ala Ala Leu Lys Asp Ser
                1220                1225                1230

Ala Gln Phe Asn Ser Ser Glu Gly Asn Met Met His Ile Ala Leu Leu
            1235                1240                1245

Ser Ala Glu Asn Glu Ser Asn Ile Ser Gly Ile Ser Ser Asp Asp Gln
    1250                1255                1260

Ala Gln His Lys Met Glu Lys Leu Ser Lys Ile Leu Lys Asp Thr Ser
265                 1270                1275                1280
```

-continued

```
Val Ala Ser Asp Leu Gln Ala Ala Gly Leu Lys Val Ile Ser Cys Ile
            1285                1290                1295

Val Gln Arg Asp Glu Ala Arg Met Pro Met Arg His Thr Phe Leu Trp
        1300                1305                1310

Leu Asp Asp Lys Ser Cys Tyr Glu Glu Gln Ile Leu Arg His Val
    1315                1320                1325

Glu Pro Pro Leu Ser Thr Leu Leu Glu Leu Asp Lys Leu Lys Val Lys
    1330                1335                1340

Gly Tyr Asn Glu Met Lys Tyr Thr Pro Ser Arg Asp Arg Gln Trp His
345                1350                1355                1360

Ile Tyr Thr Leu Arg Asn Thr Glu Asn Pro Lys Met Leu His Arg Val
            1365                1370                1375

Phe Phe Arg Thr Ile Val Arg Gln Pro Asn Ala Gly Asn Lys Phe Arg
        1380                1385                1390

Ser Ala Gln Ile Ser Asp Ala Glu Val Gly Cys Pro Glu Glu Ser Leu
        1395                1400                1405

Ser Phe Thr Ser Asn Ser Ile Leu Arg Ser Leu Met Thr Ala Ile Glu
    1410                1415                1420

Glu Leu Glu Leu His Ala Ile Arg Thr Gly His Ser His Met Tyr Leu
425                1430                1435                1440

Cys Ile Leu Lys Glu Gln Lys Leu Leu Asp Leu Ile Pro Phe Ser Gly
        1445                1450                1455

Ser Thr Ile Val Asp Val Gly Gln Asp Glu Ala Thr Ala Cys Ser Leu
    1460                1465                1470

Leu Ser Lys Met Ala Leu Lys Ile His Glu Leu Val Gly Ala Arg Met
        1475                1480                1485

His His Leu Ser Val Cys Gln Trp Glu Val Lys Leu Lys Leu Asp Cys
    1490                1495                1500

Asp Gly Pro Ala Ser Gly Thr Trp Arg Val Val Thr Thr Asn Val Thr
505                1510                1515                1520

Gly His Thr Cys Thr Ile Asp Ile Tyr Arg Glu Val Glu Glu Ile Glu
            1525                1530                1535

Ser Gln Lys Leu Val Tyr His Ser Ala Ser Ser Ala Gly Pro Leu
        1540                1545                1550

His Gly Val Ala Leu Asn Asn Pro Tyr Gln Pro Leu Ser Val Ile Asp
    1555                1560                1565

Leu Lys Arg Cys Ser Ala Arg Asn Asn Arg Thr Thr Tyr Cys Tyr Asp
    1570                1575                1580

Phe Pro Leu Ala Phe Glu Thr Ala Leu Gln Lys Ser Trp Gln Ser Asn
585                1590                1595                1600

Gly Ser Thr Val Ser Glu Gly Asn Glu Asn Ser Lys Ser Tyr Val Lys
            1605                1610                1615

Ala Thr Glu Leu Val Phe Ala Glu Lys His Gly Ser Trp Gly Thr Pro
        1620                1625                1630

Ile Ile Pro Met Glu Arg Pro Ala Gly Leu Asn Asp Ile Gly Met Val
    1635                1640                1645

Ala Trp Ile Met Glu Met Ser Thr Pro Glu Phe Pro Asn Gly Arg Gln
        1650                1655                1660

Ile Ile Val Val Ala Asn Asp Ile Thr Phe Arg Ala Gly Ser Phe Gly
665                1670                1675                1680

Pro Arg Glu Asp Ala Phe Phe Glu Thr Val Thr Asn Leu Ala Cys Glu
        1685                1690                1695
```

-continued

Arg Lys Leu Pro Leu Ile Tyr Leu Ala Ala Asn Ser Gly Ala Arg Ile
            1700                1705                1710

Gly Ile Ala Asp Glu Val Lys Ser Cys Phe Arg Val Gly Trp Ser Asp
        1715                1720                1725

Glu Gly Ser Pro Glu Arg Gly Phe Gln Tyr Ile Tyr Leu Thr Glu Glu
        1730                1735                1740

Asp Tyr Ala Arg Ile Ser Ser Val Ile Ala His Lys Leu Glu Leu
745                 1750                1755                1760

Asp Ser Gly Glu Ile Arg Trp Ile Ile Asp Ser Val Val Gly Lys Glu
            1765                1770                1775

Asp Gly Leu Gly Val Glu Asn Ile His Gly Ser Ala Ala Ile Ala Ser
            1780                1785                1790

Ala Tyr Ser Arg Ala Tyr Glu Glu Thr Phe Thr Leu Thr Phe Val Thr
            1795                1800                1805

Gly Arg Thr Val Gly Ile Gly Ala Tyr Leu Ala Arg Leu Gly Ile Arg
            1810                1815                1820

Cys Ile Gln Arg Leu Asp Gln Pro Ile Ile Leu Thr Gly Phe Ser Ala
825                 1830                1835                1840

Leu Asn Lys Leu Leu Gly Arg Glu Val Tyr Ser Ser His Met Gln Leu
            1845                1850                1855

Gly Gly Pro Lys Ile Met Ala Thr Asn Gly Val Val His Leu Thr Val
            1860                1865                1870

Pro Asp Val Leu Glu Gly Val Ser Asn Ile Leu Arg Trp Leu Ser Tyr
            1875                1880                1885

Val Pro Ala Asn Ile Gly Gly Pro Leu Pro Ile Thr Lys Pro Leu Asp
            1890                1895                1900

Pro Pro Asp Arg Pro Val Ala Tyr Ile Pro Glu Asn Thr Cys Asp Pro
905                 1910                1915                1920

Arg Ala Ala Ile Cys Gly Val Asp Asp Ser Gln Gly Lys Trp Leu Gly
            1925                1930                1935

Gly Met Phe Asp Lys Asp Ser Phe Val Glu Thr Phe Glu Gly Trp Ala
            1940                1945                1950

Lys Thr Val Val Thr Gly Arg Ala Lys Leu Gly Gly Ile Pro Val Gly
            1955                1960                1965

Val Ile Ala Val Glu Thr Gln Thr Met Met Gln Ile Ile Pro Ala Asp
            1970                1975                1980

Pro Gly Gln Leu Asp Ser His Glu Arg Ser Val Pro Arg Ala Gly Gln
985                 1990                1995                2000

Val Trp Phe Pro Asp Ser Ala Thr Lys Thr Ala Gln Ala Leu Leu Asp
            2005                2010                2015

Phe Asn Arg Glu Gly Leu Pro Leu Phe Ile Leu Ala Asn Trp Arg Gly
            2020                2025                2030

Phe Ser Gly Gly Gln Arg Asp Leu Phe Glu Gly Ile Leu Gln Ala Gly
            2035                2040                2045

Ser Thr Ile Val Glu Asn Leu Arg Thr Tyr Asn Gln Pro Ala Phe Val
            2050                2055                2060

Tyr Ile Pro Met Ala Gly Glu Leu Arg Gly Gly Ala Trp Val Val Val
065                 2070                2075                2080

Asp Ser Lys Ile Asn Pro Asp Arg Ile Glu Cys Tyr Ala Glu Arg Thr
            2085                2090                2095

Ala Lys Gly Asn Val Leu Glu Pro Gln Gly Leu Ile Glu Ile Lys Phe
            2100                2105                2110

```
Arg Ser Glu Glu Leu Gln Asp Cys Met Gly Arg Leu Asp Pro Glu Leu
    2115                2120                2125

Ile Asn Leu Lys Ala Lys Leu Gln Asp Val Asn His Gly Asn Gly Ser
        2130                2135                2140

Leu Pro Asp Ile Glu Gly Ile Arg Lys Ser Ile Glu Ala Arg Thr Lys
145                 2150                2155                2160

Gln Leu Leu Pro Leu Tyr Thr Gln Ile Ala Ile Arg Phe Ala Glu Leu
            2165                2170                2175

His Asp Thr Ser Leu Arg Met Ala Ala Lys Gly Val Ile Lys Lys Val
        2180                2185                2190

Val Asp Trp Glu Glu Ser Arg Ser Phe Phe Tyr Lys Arg Leu Arg Arg
    2195                2200                2205

Arg Ile Ala Glu Asp Val Leu Ala Lys Glu Ile Arg Gln Ile Val Gly
    2210                2215                2220

Asp Lys Phe Thr His Gln Leu Ala Met Glu Leu Ile Lys Glu Trp Tyr
225                 2230                2235                2240

Leu Ala Ser Gln Ala Thr Thr Gly Ser Thr Gly Trp Asp Asp Asp
            2245                2250                2255

Ala Phe Val Ala Trp Lys Asp Ser Pro Glu Asn Tyr Lys Gly His Ile
        2260                2265                2270

Gln Lys Leu Arg Ala Gln Lys Val Ser His Ser Leu Ser Asp Leu Ala
    2275                2280                2285

Asp Ser Ser Ser Asp Leu Gln Ala Phe Ser Gln Gly Leu Ser Thr Leu
    2290                2295                2300

Leu Asp Lys Met Asp Pro Ser Gln Arg Ala Lys Phe Val Gln Glu Val
305                 2310                2315                2320

Lys Lys Val Leu Asp
            2325
```

(2) INFORMATION FOR SEQ ID NO:11:

(i) SEQUENCE CHARACTERISTICS:
        (A) LENGTH: 3544 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

```
AAGCTTGGTA TGGATTCGTC AGCGCCAAGC CGGGGTTTTG CATGCGCCCG ACTGGAARCS     60

GAATTCCGTG AGCCCTGTAC RRCAATGGCA ACCCCASGGT TACTGGGGTG GCTGAATGGT    120

CTCSGCTTAC GCAATTGTTT GTGGCAGCWG CGTGGGCTAA ATGTARGTTG TCTCTTGTTG    180

CACTGCARGA TGGATGGGTA GCCTCTGGGC CGCCTCTGCT ARTGTCTARC GTTTGCTGAC    240

TGTGGTTTAN TCAGGGATGC CCATGCCCAT GCTAGATTGA TAGGTGCCAT TCTAATGGTA    300

GGTGGCGGTA AGGTTTATTA AGCTGTAGTA TCAGTAGGTA ACCTCATGAA TCAGGGTTTA    360

AGCACACCTT TTCCTTTGTG TGGGTGCATA AGGAATGCAC TTGGCTTCGT TCCCTGATAG    420

TCTTTGCTCA TGTGTCATTC TACCAAGTGG GTTACTGTAA CATTGCACTC TATGATGGTT    480

GGTGGTTGTG CATCTTTTTG CTTCCCCTGG TTGTCTAATA CCTGCATGTA ACTGATGACC    540

TTCTTTTATG TATCATATAG ATTACATCCT TTTGTTGTAC ATCTCAATTC TGAAAAAACA    600

ATGTTTTGCA TTCTTAGCGC TCTGTGCACA AGGAAAAGGA GGTTTTACCT GCAACTTTTT    660

TTTTCGAGAA AAAACAAACC TTTCTGAAAG GCAGTGATCA TTTAGTATAA AGAAAATTTG    720
```

```
ATTTACTTTC TTCAGAGAGA ATATKCCAAR CAAACAATTT TCTTACTGTC TGAGCCACGA   780

AATTTGATCT TGATCTTACT TTCACAAGCC ACATGAAGCC TTATCATCGC TCTGATAAAA   840

AAGCCAAATA GGTGATTCAT AGAATGAGAG AAAGAACCTG TTGCCATTTG GGGRCCTTGT   900

TGTGTACTCA TTATCCCCCC TGCTCAGGTT GAGGTTTTCC TTGCCACTGC CACCCCTTGG   960

CCCCTTCTTA TACAACCATC TCCATTGAAA AAGATTTTGC ACTACATTTG GGCTCGTATG  1020

ACAAAAAAGG AAAATAAAAC TAAACAGCAG AAACATAGTA TAATTATAGG TAAAAGGTTC  1080

TGGCAAGTTT GAGTGGAAGA GACCTTTGTA TATTTGGACA TATTTCACTA GTAAATAGTT  1140

TTCTAAAATC TTCATGAATG GTGGCCAATA AACTTGATAA GATCTCAACA TGGCAGGTTC  1200

CTTCMAAATG AGAGGAAAAC TGGAAACATC ACAAATATTT TTAGCGAGT GGCCTATAAA  1260

TTATAATGTT GCTTTCATTT CTTTGATATT CAAAACTTCC TAAGAGTATT CTGCTAGAGC  1320

TCTGATGGTG TCTTTTGCCT CTGTCAGATT TTCCAGGAGT TTTCTTCCCT TTTTATGGCA  1380

CTGTGCGTTT GAGAAGGTCT TCAATTGTGC TGTCTGGGCC ACGGAACGAC AATGTCACAG  1440

CTTGGATTAG CCGCAGCTGC CTCAAAGGCC TTGCCACTAC TCCCTAATCG CCAGAGAAGT  1500

TCAGCTGGGA CTACATTCTC ATCATCTTCA TTATCGAGGC CCTTAAACAG AAGGAAAAGC  1560

CATACTCGTT CACTCCGTGA TGGCGGAGAT GGGGTATCAG ATGCCAAAAA GCACAGCCAG  1620

TCTGTTCGTC AAGGTACTGT GAATATCTTT TGATACAAGC TAAAATTTTG CTACAGAATA  1680

TATATTAAAG AGTTCTTTCT TGGCTGGTGT TGTTTATTTN GTTTTAANCA TGCGAAAGGG  1740

CCTCTAGTTG AGTTGGTTAG GTGGCCTGAA TACCACTCCT TAAGGTCTTG AGTTTGNNAT  1800

TTTCCGTCGG AGCGAATTTT AGGCTAGGGT TACCCCCCCA CCCCCACCCG AATCTGCACA  1860

GTCCGGTCGT GGTCGTCCTC ATATAGGCTA CGATGTCATT GTGTATCGGC GGGCCAGGGG  1920

TTTAAGAGTT TTCTTGACCT TTGTTAGAAG ATCTTAATAA TACAATGTCC AAGGGCTGTC  1980

TTACCCTGTA GGTCGAGTTT TTAGTTGTTT TAACATGGTA ATGTTTGAAG CCTCATTCTA  2040

GGTACCAATA TAGATATGCT CACTGCTCAG TTTCAAATGT TTGTCTGCAT GTAGGTCTTG  2100

CTGGCATTAT CGACCTCCCA AGTGAGGCAC CTTCCGAAGT GGATATTTCA CAGTAAGGAC  2160

TACAATATTT TGCGTACGTT TGNTTTTGGA AAAAGAAAAT ATTCTCAGCT TATTTATACT  2220

AGCTTCGCTA ANTACTGAAA NNTGCTGTCT TAATGTCCTG GTNGCTGTAT GCTCAATCTT  2280

TCATAGTAAA TGCTGCAAAA TATGTGATGT AACTGTTGCA ACACAGCCAG GGACCTGTTA  2340

TTTAGAGCAT GGTGAATGCT CTGGTTCAGT TATATGATGT AGTTATAGCT CATGTTGAAG  2400

AATTAGTTGC AGTGTTTGCT GGACAATGGT CACTTATTAT AAATCATATC TGCATACACA  2460

TTTGTGACTT CTGTTGCTGT AAATGCCCGC ATTTTTTGAG AAAAATTTAA ATGCTTGGCC  2520

TAAATTGGAC ATATATGATA GACACCAAGC TGATTTGAAC TTTGTTTATT TTTGACATCC  2580

ATGCATATTG TCAGTGTTGT GAAAACAATA CTAATCCTTT TTTTTTGTCT TTTTCCAGTG  2640

GATCTGAGGA TCCTAGGGGG CCAACAGATT CTTATCAAAT GAATGGGATT ATCAATGAAA  2700

CACATAATGG AAGACATGCC TCAGTGTCCA AGGTTGTTGA ATTTGTGCG GCACTAGGTG  2760

GCAAAACACC AATTCACAGT ATATTAGTGG CCAACAATGG AATGGCAGCA GCAAAATTTA  2820

TGAGGAGTGT CCGGACATGG GCTAATGATA CTTTTGGATC TGAGAAGGCA ATTCAACTCA  2880

TAGCTATGGC AACTCCGGAA GACATGAGGA TAAATGCAGA ACACATTAGA ATTGCTGACC  2940

AATTNCGTAG AGGTGCCTGG TGGAACAAAC AATAATAACT ACGNCCAATG TTCAACTCAT  3000

AGTGGAGGTT AGCCTTGCTA ATCTGTTAGT TTACTACTGG TCTGCTGTTT CCTTTATTTG  3060

TTGTATAATG ATTGACATAT TTAAGTAGAG AAATTTATAT TTCTCCTCTG CTGTTGTGGA  3120
```

```
AGTCCAATTG TCATCATTAA CTGTGAAATA TTGCAGATGG CACAAAAACT AGGTGTTTCT    3180

GCTGTTTGGC CTGGTTGGGG TCATGCTTCT GAGAATCCTG AACTGCCAGA TGCATTGACC    3240

GCAAAAGGGA TCGTTTTTCT TGGCCCACCT GCATCATCAA TGAATGCTTT GGGAGATAAG    3300

GTCGGCTCAG CTCTCATTGC TCAAGCAGCC GGGGTCCCAA CTCTNTGCTT GGAGTGGATC    3360

ACATGTGAGT CTCACTCTTT GATTACTATC CGCCTGTCTC ATTGCTCTCT CTTTCATATT    3420

CTAATGACAC TAAATTTAGG TTGAAGTTCC ATTAGAGTGC TGCTTAGACG CGATACCTGA    3480

GGAGATGTAT AGAAAAGCTT ATCGATACCK TCGACCTCGA GGGGGGGCCC GGTACYAGCT    3540

GSTG                                                                3544
```

(2) INFORMATION FOR SEQ ID NO:12:

(i) SEQUENCE CHARACTERISTICS:
    (A) LENGTH: 2166 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO:12:

```
GAATTCCGTG AGCCCTGTAC GGCAATGGCA ACCCCAGGGT TACTGGGGTG GCTGAATGGT      60

CTCGGCTTAC GCAATTGTTT GTGGCAGCTG CGTGGGCTAA ATGTAGGTTG TCTCTTGTTG     120

CACTGCAGGA TGGATGGGTA GCCTCTGGGC CGCCTCTGCT AGTGTCTAGC GTTGCTGACT     180

GTGGTTTATT CAGGGATGCC ATGCCCATGC TAGATTGATA GGTCATAGGT GCCATTCTAA     240

TGGTAGGTGG CGGTAAGGTT TATTAAGCTG TCGTATCAGT AGGTAACCTC ATGAATCAGG     300

GTTTAAGCCC ACCTTCTCCT TTGTGTGGGT GCATAAGGAA TGCACTTGGC TTCGTTCCCT     360

GCTAGTCTTT GCTCATGTGT CATTCTACCA AGTGGGTTAC TGTAACATTG CACTCTATGA     420

TGGTTGGTGG TTGTGCATCT TTTTGCTTCC CCTGGTTGTC TAATACCTGC ATGTAACTGA     480

TGACCTTCTT TTATGTATCA TATAGATTAC ATCCTTTTGT TGTACATCTC AATTCTGAAA     540

AACAATGTTT TGCATTCTTA GCGCTCTGTG CACAAGGAAA AGGAGGTTTT ACCTGCAACT     600

TTTTTTTTCG AGAAAAAACA AACCTTTCTG AAAGGCAGTG ATCATTTAGT ATAAAGAAAA     660

TTTGATTTAC TTTCTTCAGA ARAGAATATT CCAAACAAAC AATTTTCTTA CAGTCTGAGC     720

CACGAAATTT GATCTTGATC TTACTTTCAC AAGCCACATG AAGCCTTATC ATCGCTCTGA     780

TAAAAAAACC AAATAGGTGA TTCATAGAAT GAGAAAAAGA ACCTGTTGCC ATTTGGGGAC     840

CTTGTTGTGT ACTCATTATC CCCCCTGCTC AGGTTGAGGT TTNCCTTGCC ACTGCCACCC     900

CTTGGCCCCT TCTTATACAA CCATCTCCAT TGAAAAAGAT TTTGCACTAC ATTTGGGCTT     960

CGTATAACAA AAAAGGAAAA TAAAACTAAA CAGCAGAAAC ATAGTATAAT TATAGGTAAA    1020

AGGTTCTGGC AAGTTTGAGT GGTAGAGACC TTTGTATATT TGGACATATT TCACTAGTAA    1080

ATAGTTTTCT AAAATGTTCA TGAATGGTGG CCAATAAACT TGATAAGATC TCAACATGGC    1140

AGGTTCCTTC AAAATGAGAG GAAAACTGGA ACATCACAA ATATTTTTA GCGAGTGGCC     1200

TATAAATTAT AATGTTGCTT TCATTTCTTT GATATTCAAA ACTTCCTAAG AGTATTCTGC    1260

TAGAGCTTCT GATGGTGTCT TTTGCCTCTG TCAGATTTTC CAGGAGNTTT TCTTCCCTTT    1320

TTATGGCACT GTGGTTTGAG AAGGTTTCAA TTGTGCTGTC TGGGCCACGG AACGACAATG    1380

TCACAGCTTG GATTAGCCGC AGCTGCCTCA AAGGCTTGC CACTACTCCC TAATCGCCAG     1440

AGAAGTTCAG CTGGGACTAC ATTCTCATCA TCTTCATTAT CGAGGCCCTT AAACAGAAGG    1500
```

```
AAAAGCCGTA CTCGTTCACT CCGTGATGGC GGAGATGGGG TATCAGATGC CAAAAAGCAC    1560

AGCCAGTCTG TTCGTCAAGG TACTGTGAAT ATCTTTTGAT ACAAGCTAAA ATTTTGCTAC    1620

AGAATATATA TTAAAGAGTT CTTTCTTGGC TGGTGTTGTT TATTTGTTTT AACATGCGAA    1680

AGGGCCTCTA GTTGAGTTGG TTAGGTGGCC TGAGTACCAC TCCTTAAGGT CTTGAGTTTG    1740

ATTTTCCGTC AGAGCGAATT TTAGGCTAGG GTTACCCCCC ACCCCCCAC CCCTACCCGA     1800

ATCTGCACAG TCCGGTCGTG GTCGTCCTCA TATAGGCTAC GATGTCATTG TGTATCGGCG    1860

GGCCAGGGGT TTAAGAGTTT CTTTGACCTT TGTGAGAAGA TCTTAATAAT ACAATGTCCA    1920

AGAGCTGTCT TACCCTGTAG GTCRAGTTTT TTAGTTGTTT AACATGGTT ATGTTTGAAG     1980

CCTCATTCTA GGTACCAATA TARATATGCT CACTGCTCAG TTTCMAATGT TTGTCTGCAT    2040

KTAGGTCTTG CTGGCATTAT CGACCTCCCA AGTGAGGCAC CTTCCGAAGT GGATATTTCA    2100

CAGTAAGGAN TACAGTATTT TGCGTACGTT TGTTTTGGAA AAAGAAATAT TCTCAGCTTA    2160

TTTAAT                                                                2166

(2) INFORMATION FOR SEQ ID NO:13:

(i) SEQUENCE CHARACTERISTICS:
        (A) LENGTH: 484 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

GAATTCCTGT GGGTGTCATA GCTGTGGAGA CACAGACCAT GATGCAGATC CTGTAATACT      60

TCAAAATCTT AAGCCACAAA ACTTGATTAA TTGTTAGCAC AGTAATTTGC CAAGTGGCTA     120

GAGAAGGATC TCAACACAAC ACAATAACCA AGAGATATCA ATCACAGAGA TGGCACGGTG     180

GTTATCCCGT GGTTCGGCCA AGACCAACGC TTGCCTACTC CACGTTGTGG CGTCCCAACG     240

GACGAGGGTT GCAATCAACC CCTCTCAAGC GGTCCAAAGA CCAACTTGAA TACCACGGTG     300

TTGCTTTGCT TTTCTTAATC CCACTTGCGA GGAATCTCCA CAGCTTGGAG CCTCTCGCCC     360

TTTCAAAAGA TTTCACAAAG AATCACGGAG CAAGGGAAGG ATCAACAACT CACACACGAC     420

ACAAAGATCA CAGTGAATAC GCACACATAA AACCAAGACT TGAGCTCAAG TGACTAGCAC     480

ACTT                                                                   484

(2) INFORMATION FOR SEQ ID NO:14:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

ATGGAAGTGT GTATTGCCAG TGCTTATTYT RGGGATATGA GGGAATTWAM ATTACATTTG       60

TGACTGGGCG GACTGTAGGA TAGGAGTTAT CTTGYTCGAT TGGTATACGG TGCATACAGS     120

KYTTGACCAG CTATTATTTT AACAGGGTTT TCTGCCCTGA ACAAGTCCTT GGGCGGGAAG     180

TGTACAGCTC CCACATGCAG CTTGGTGGTC CTAAGATCAT GGCGACCAAT GGTGTTGTCC     240

ACCTCACTGT TCCAGATGAC CTTGAAGGTG TTTCCAATAT ATTGAGGTGG CTCAGCTATG     300

TTCCTGCAAA CATTGGTGGA CCTCTTCCTA TTACCAAACC TCTGGACCCT CCAGACAGAC     360
```

```
CTGTTGCTTA CATCCCTGAG AACACATGCG ATCCACGTGC AGCTATCTGT GGTGTAGATG        420

ACAGCCAAGG GAAATGGTTG GGTGGTATGT TTGACAAAGA CAGCTTTGTG GAGACATTTG        480

AAGGATGGGC AAAAACAGTG GTTACTGGCA GAGCAAAGCT TGGAGGAATT C                531
```

(2) INFORMATION FOR SEQ ID NO:15:

(i) SEQUENCE CHARACTERISTICS:
        (A) LENGTH: 882 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:15:

```
CTCCCAATAT TGTCATGAGG CTTGCATCCC AGGTTAGTTT TTTTTCCTTT CTGAAATTTA         60

TATTCCATAC CTTTTCACCT TTAGTTATCC TTGTATTTTC TGGAAGCTTC ATCTGATGCA        120

TTATTGACAA ATGCACTAAT GGTCATCATA TTTGSAKAGW YAASATATKT MTCTTAATTG        180

ATGGKWACTM TTGAMWATGA SRATGSTKRA GCAKRTRRYK WAYASTTTTT TAATAAAAAA        240

ACATGCATTT CTAGGAGTTG GACTAAGCTT TTCTTAGTAT GAAGTGCCAT GTTTTACATG        300

GTCCATTTGT GTCAATTTAC AGTCGGTATC ATGGAAAGGT TGTCATAATG GCTGGAGAGA        360

AACAACACAT CTTGTTTCTC AACACTTGTG GGAGAAGATG TTTTACCTTT TTTCCTAAAA        420

TTACTTTTTG TACTAAATTG TATAAKTTTT CCAATATTCT CCATGATTAT TGAACTCTGC        480

TGTGTTCAAA CAGCCAAAAC ATGTTTCCAT ACTTTACACC TTTATTTTTT AGATGGAAGC        540

CTGGAATTGT GCTCTGTTAT CTGTAGTCAT GCATTATATT TGATCTTAAA TCYTATTCTC        600

TATTGTAGAR TCSGCATCTT GAAGTTCAGT TGCTTTGTGA TCAATATGGT AATGTAGCAG        660

CACTTCACAG TCGTGATTGC AGTGTGCAAC GGCGCACACCA GAAGGTCTGC CCCTCACCCA        720

CCCAGCCATA AACACGAAGT TTATAGAACC ATGTATTTTG TTATGCAATA TATTTCTCAA        780

TTGTAGCTCC ATTCACATTT TGCTACAACA GATTATTGAA GAAGGTCCAG TTACTGTTGC        840

TNCCTCGTGA GACAGTTAAA GCACTTGAGC AGCAGCAAGG AG                          882
```

(2) INFORMATION FOR SEQ ID NO:16:

(i) SEQUENCE CHARACTERISTICS:
        (A) LENGTH: 867 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:16:

```
GTCGACCTGC AGGTCAACGG ATCCTAGGGG GCCAACAGAT TCTTATCAAA TGAATGGGAT         60

TATCAATGAA ACACATAATG GAAGACATGC CTCAGTGTCC AAGGTTGTTG AATTTTGTGC        120

GGCACTAGGT GGCAAAACAC CAATTCACAG TATATTAGTG GCCAACAATG GAATGGCAGC        180

AGCAAAATTT ATGAGGAGTG TCCGGACATG GGCTAATGAT ACTTTTGGAT CTGAGAAGGC        240

AATTCAACTC ATAGCTATGG CAACTCCGGA AGACATGAGG ATAAATGCAG AACACATTAG        300

AATTGCTGAC CAATTCGTAG ARGTGCCTGG TGGAACAAAC AATAATAACT ACGCCAATGT        360

TCAACTCATA GTGGAGGTTA GCCTTGCTAA TCTGTTAGTT TACTACTGGT CTGCTGTTTC        420

CTTTATTTGT TGTATAATGA TTGACATATT TAAGTAGAGA AATTTATATT TCTCCTCTGC        480

TGTTGTGGAA GTCCAATTGT CACCATTAAC TGTGAAATAT TGCAGATGGC ACAAAAACTA       540
```

-continued

| | | |
|---|---|---|
| GGTGTTTCTG CTGTTTGGCC TGGTTGGGGT CATGCTTCTG AGAATCCTGA ACTGCCAGAT | 600 |
| GCATTGACCG CAAAAGGGAT CGTTTTTCTT GGCCCACCTG CATCATCAAT GAATGCTTTG | 660 |
| GGAGATAAGK TCGGCTCAGC TCTCATTGCT CAAGCAGCCG GGGTCCCAAC TCTTGCTTGG | 720 |
| AGTGGATCAC ATGTGAGTCT CACTCTTTGA TTACTATCCG CCTGTCTCAT TGCTCTCTCT | 780 |
| TTCATATTCT AATGACACTA AATTTAGGTT GAAGTTCCAT TAGAGTGCTG CTTAGACGCG | 840 |
| ATACCTGAGG AGATGTATAG AAAAGCT | 867 |

(2) INFORMATION FOR SEQ ID NO:17:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:17:

| | | |
|---|---|---|
| GAATAATCTG CCTGCAGCTC AAGTTGCTGT TGGAATGGGC ATACCTCTTT GGCAGATTCC | 60 |
| AGGTAATTAC CAATTTACCA ACTTATTTAG TTCCTTATTG TTTTATTCTC TAATTTTCTA | 120 |
| CTTATGTAGA AATCAGACGT TTCTATGGAA TGGACTATGG AGGAGGGTAT GACATTTGGA | 180 |
| GGAAAACAGC AGCTCTTGCT ACACCATTTA ATTTTGATGA AGTAGATTCT CAATGGCCAA | 240 |
| AGGGCCATTG TGTAGCAGTT AGAATTACTA GTGAGGACCC AGATGATGGT TTCAAACCTA | 300 |
| CTGGTGGGAA AGTGAAGGTA AGTTTTCTAG ATGACATGTA TTATATATCG TTCAAAGAGA | 360 |
| TTAAGTTTGG TTAAATGACT AGGTCTTGAT TTTTTATCTT TCAGGAGATA AGTTTTAAAA | 420 |
| GCAAGCCTAA TGTTTGGGCC TACTTCTCAG TAAAGGTAAC TTGTTAACTT TAGTACGCTG | 480 |
| TCACATTATT CTTCGTTGTG AAAATAATTT GAACGGTTCT CTTTGTATTT TAACCATCCA | 540 |
| TCGTCTCATT TAGCAGAGCA CACAAATATT TGCACTGACC CCCCTCCCCT TATCTGCTTT | 600 |
| CAGTCTGGTG GAGGCATTCA TGAATTTGCT GATTCTCAGT TCGGTATGTG TAAACCAAGA | 660 |
| GTATTCTTTG TAATTTATAT TGGTCCTCAA TTTTGAAATA TTGTCTTTCC GTTACAGGAC | 720 |
| ADG | 723 |

(2) INFORMATION FOR SEQ ID NO:18:

(i) SEQUENCE CHARACTERISTICS:
        (A) LENGTH: 231 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

| | | |
|---|---|---|
| AATTCCTGTG GGTGTTATAG CTGTGGAGAC ACAGACCATG ATGCAGCTCA TCCCTGCTGA | 60 |
| TCCAGGTCAA CTTGATTCCC ATGAGCGATG TGTTCCTCGG GCTGGACAAG TGTGGTTCCC | 120 |
| AGATNCTGCA ACCAAGACAG CTCAGGCATT ATTAGACTTC AACCGTGAAG GATTGCCTCT | 180 |
| GTTCATCCTG GCTAACTGGA GAGGCTTCTC TGGGGACAG AGAGATCTCT T | 231 |

(2) INFORMATION FOR SEQ ID NO:19:

(i) SEQUENCE CHARACTERISTICS:
        (A) LENGTH: 207 base pairs
        (B) TYPE: nucleic acid (C) STRANDEDNESS: single
            (D) TOPOLOGY: linear (ii) MOLECULE TYPE: Genomic DNA (xi) SEQUENCE DESCRIPTION: SEQ ID NO:19:

AATTCATGCA TCTTAATAAA CACAGTTGGC CCTTAAAGCA AGTGAACTTC TTGAACAAAC      60

CAAACTAAGT GAACTCTGTT CCAGCATTGC AAGAAGCCTT TCAGATCTGG GGATGCATAA     120

GGGAGAAATG ACTATTAAGG ATAGCATGGA AGATTTAGTC TCTGNCCCAT TGCCTGTTGA     180

AGATGCTCTT ATTTCTTTGT TTGATTA                                        207

(2) INFORMATION FOR SEQ ID NO:20:

(i) SEQUENCE CHARACTERISTICS:
            (A) LENGTH: 180 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:20:

ATAGACCTGT CGCATACATC CCTGAGAACA CATGCGATCC GCGTGCAGCC ATCCGTGGNG      60

TAGATGACAG CCAAGGGAAA TGGTTGGGTG GTATGTTTGA CAAAGACAGC TTTGTGGAGA     120

CATTTGAAGG ATGGGCAAAA ACAGTGGTTA CTGGTAGAGC AAAGCTTGGA GGAAGGAATT     180

(2) INFORMATION FOR SEQ ID NO:21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:21:

CCTTTTTATG GCACTGTGCG                                                 20

(2) INFORMATION FOR SEQ ID NO:22:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:22:

CATCGTAGCC TATATGAGGA CG                                              22